US012240897B2

(12) United States Patent
Koltsova

(10) Patent No.: US 12,240,897 B2
(45) Date of Patent: Mar. 4, 2025

(54) TREATMENT OF NON-ALCOHOLIC STEATOHEPATITIS (NASH) WITH IL-27 ANTIBODY

(71) Applicant: Institute For Cancer Research, Philadelphia, PA (US)

(72) Inventor: Ekaterina Koltsova, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 206 days.

(21) Appl. No.: 17/480,946

(22) Filed: Sep. 21, 2021

(65) Prior Publication Data

US 2022/0089714 A1 Mar. 24, 2022

Related U.S. Application Data

(60) Provisional application No. 63/093,847, filed on Oct. 20, 2020, provisional application No. 63/081,471, filed on Sep. 22, 2020.

(51) Int. Cl.
| | | |
|---|---|---|
| *C07K 16/24* | (2006.01) | |
| *A61K 39/00* | (2006.01) | |
| *A61K 39/395* | (2006.01) | |
| *A61K 45/06* | (2006.01) | |
| *A61P 35/00* | (2006.01) | |
| *C07K 16/28* | (2006.01) | |

(52) U.S. Cl.
CPC ........ *C07K 16/244* (2013.01); *A61K 39/3955* (2013.01); *A61K 45/06* (2013.01); *A61P 35/00* (2018.01); *C07K 16/2866* (2013.01); *A61K 2039/505* (2013.01)

(58) Field of Classification Search
None
See application file for complete search history.

(56) References Cited

U.S. PATENT DOCUMENTS

| 2012/0183548 A1* | 7/2012 | Wong | A61K 38/1793 |
| | | | 435/375 |
| 2015/0004133 A1* | 1/2015 | Kisseleva | A61K 38/20 |
| | | | 424/133.1 |
| 2015/0284459 A1* | 10/2015 | Kuchroo | A61K 39/46449 |
| | | | 424/278.1 |
| 2019/0365781 A1* | 12/2019 | Anderson | A61K 38/20 |

FOREIGN PATENT DOCUMENTS

| WO | WO-2004069173 A2 * | 8/2004 | | A61K 38/20 |
| WO | WO-2011133931 A1 * | 10/2011 | | A61P 37/00 |
| WO | WO-2019183499 A1 * | 9/2019 | | A61K 38/20 |
| WO | WO-2020123011 A1 * | 6/2020 | | A61P 35/00 |

OTHER PUBLICATIONS

Grohman et al. Obesity Drives STAT-1-Dependent NASH and STAT-3-Dependent HCC. Cell 175, 1289-1306 (Year: 2018).*
Dietrich et al. A Soluble Form of IL-27Rα Is a Natural IL-27 Antagonist. The Journal of Immunology. 192 (11): 5382-5389; Published: Jun. 1, 2014 (Year: 2014).*
Belle et al. Blood. 128(16): 2068-2082; Published: Aug. 3, 2016 (Year: 2016).*
Kong et al. Frontiers in Physiology. 3(69): 1-7; Published: Apr. 3, 2012 (Year: 2012).*
Mendez-Sanchez et al. Annals of Translational Medicine. 8(6): 400; Published: Mar. 31, 2020 (Year: 2020).*
Fahlbusch. Heinrich-Heine-Universität Düsseldorf Dissertation; Published: Jun. 13, 2019 (Year: 2019).*
Lytle et al. PLoS One. 12(4): e0173376; Published: Apr. 19, 2017 (Year: 2017).*
Farooq et al. Journal of Hepatology. 68: THU-475; Published: Apr. 2018 (Year: 2018).*
Dibra et al. Hepatology. 63(3): 1000-1012; Published: Mar. 2016 (Year: 2016).*
Villarino et al., "The IL-27R (WSX-1) Is Required to SuppressT Cell Hyperactivity during Infection", Immunity, 2003, 19, pp. 645-655.
Findlay et al., "Essential Role for IL-27 Receptor Signaling in Prevention of Th1-Mediated Immunopathology during Malaria Infection", J Immunol, 2010, 185(4), pp. 2482-2492.
Fitzgerald et al., "Suppressive Effect of IL-27 on Encephalitogenic Th17 Cells and the Effector Phase of Experimental Autoimmune Encephalomyelitis", J Immunol, 2007, 179(5), pp. 3268-3275.
Peshkova et al., "IL-27R signaling controls myeloid cells accumulation and antigen-presentation in atherosclerosis", Scientific Reports, 2017, 7(2255), pp. 1-14.
Peshkova et al., "IL-27 receptor-regulated stress myelopoiesis drives abdominal aortic aneurysm development", Nature Communications, 2019, 10(5046), pp. 1-15.
Ringelhan et al., "The immunology of hepatocellular carcinoma", Nat Immunol, 2018, 19(3), pp. 222-232.
Koltsova et al., "Interleukin-27 Receptor Limits Atherosclerosis in Ldlr−/− Mice", Circulation Research, 2012, 111, pp. 1274-1285.
Yoshida et al., "The immunobiology of interleukin-27", Annu Rev Immunol, 2015, 33, pp. 417-443.
Yoshida et al., "WSX-1 Is Required for the Initiation of Th1 Responses and Resistance to L. major Infection", Immunity, 2001, 15(4), pp. 569-578.
Greten et al., "Inflammation and Cancer: Triggers, Mechanisms, and Consequences", Immunity, 2019, 51(1), pp. 27-41.
Park et al., "Dietary and genetic obesity promote liver inflammation and tumorigenesis by enhancing IL-6 and TNF expression", Cell, 2010, 140(2), pp. 197-208.
Nakagawa et al., "ER stress cooperates with hypernutrition to trigger TNF-dependent spontaneous HCC development", Cancer Cell, 2014, 26(3), pp. 331-343.

(Continued)

*Primary Examiner* — Juliet C Switzer
*Assistant Examiner* — Katherine Ann Holtzman
(74) *Attorney, Agent, or Firm* — Armstrong Teasdale LLP

(57) ABSTRACT

The present disclosure provides methods of treating non-alcoholic steatohepatitis (NASH) in a subject by administering to the subject an inhibitor of IL-27 or IL-27R.

7 Claims, 59 Drawing Sheets

(56) References Cited

OTHER PUBLICATIONS

Wong et al., "High serum interleukin-6 level predicts future hepatocellular carcinoma development in patients with chronic hepatitis B†", Int J Cancer, 2009, 124, pp. 2766-2770.
Carl et al., "IL27: Its Roles in the Induction and Inhibition of Inflammation", Int J Clin Exp Pathol, 2008, 1(2), pp. 117-123.
Hirase et al., "Interleukin 27 inhibits atherosclerosis via immunoregulation of macrophages in mice", Am J Physiol Heart Circ Physiol, 2013, 305, pp. H420-H429.
Cai et al., "Functional impairment in circulating and intrahepatic NK cells and relative mechanism in hepatocellular carcinoma patients", Clin Immunol, 2008, 129(3), pp. 428-437.
Michelet et al., "Metabolic reprogramming of natural killer cells in obesity limits antitumor responses", Nature Immunology, 2018, 19, pp. 1330-1340.
Long et al., "Controlling natural killer cell responses: integration of signals for activation and inhibition", Annu Rev Immunol, 2013, 31, pp. 227-258.
Pflanz et al., "IL-27, a heterodimeric cytokine composed of EBI3 and p28 protein, induces proliferation of naive CD4+ T cells", Immunity, 2002, 16(6), pp. 779-790.
Kumar et al., "IL-27 promotes NK cell effector functions via Maf-Nrf2 pathway during influenza infection", Scientific Reports, 2019, 9(4984), pp. 1-15.
Raulet et al., "Regulation of ligands for the NKG2D activating receptor", Annu Rev Immunol, 2013, 31, pp. 413-441.
Shifrin et al., "NK cell self tolerance, responsiveness and missing self recognition", Semin Immunol, 2014, 26(2), pp. 138-144.

\* cited by examiner

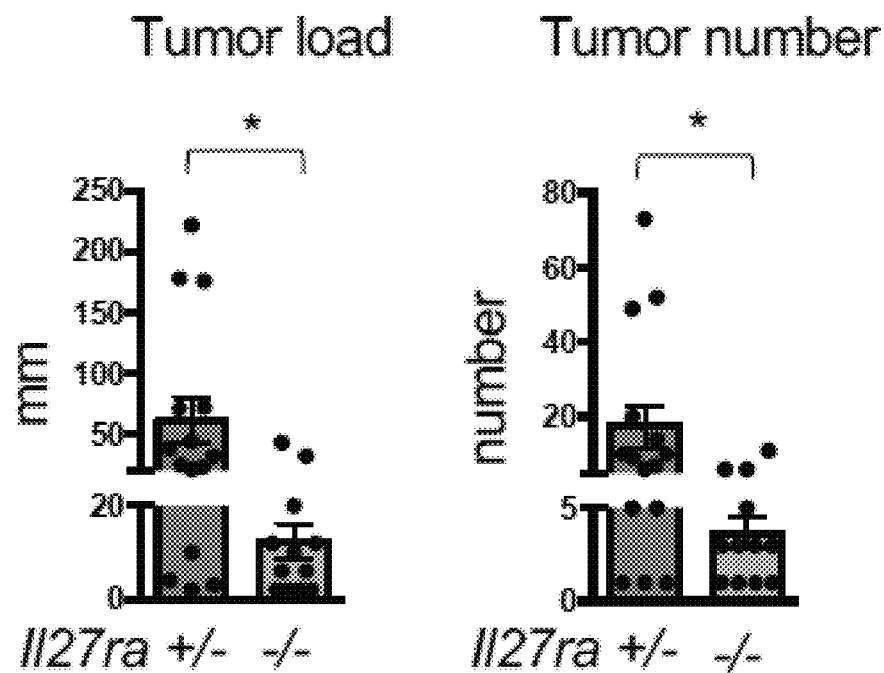
Figure 1E
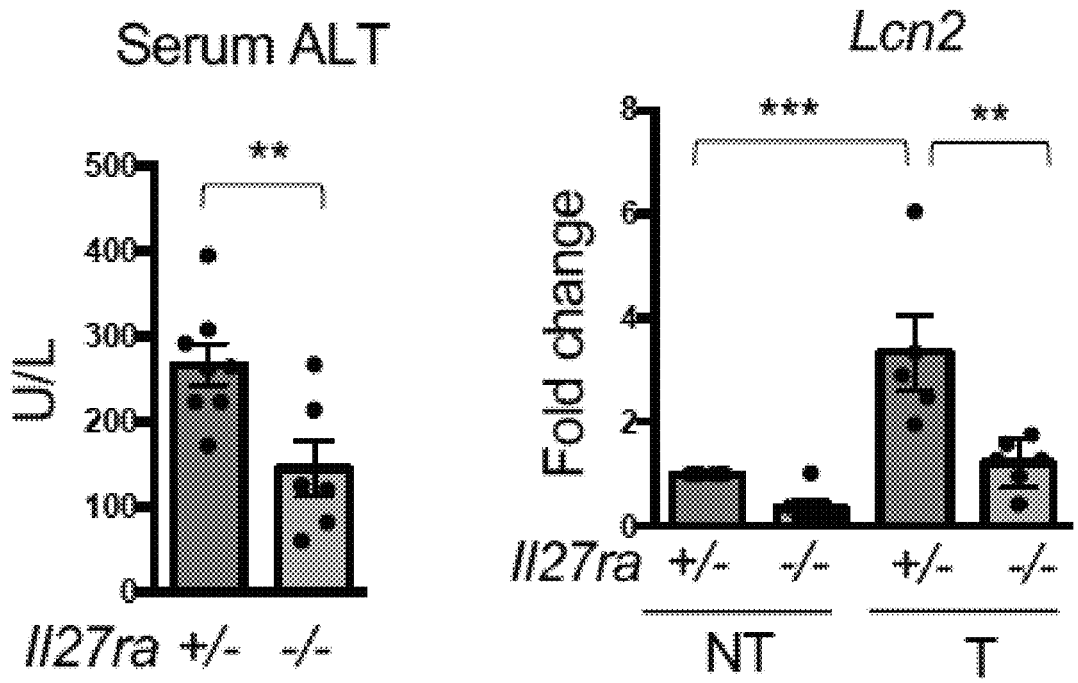
Figure 1F
Figure 1G

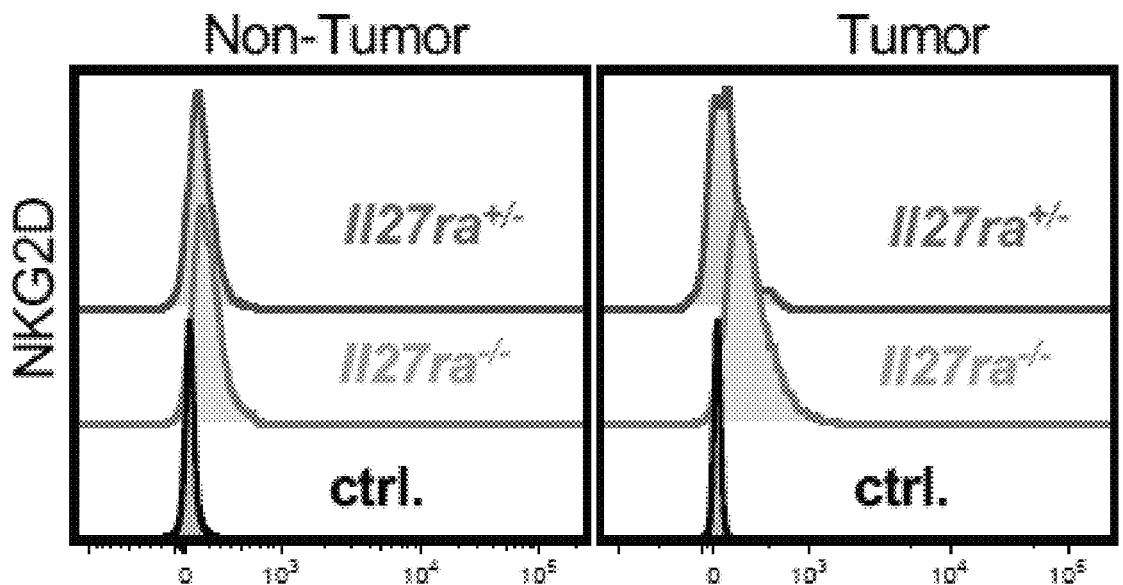
Figure 3A
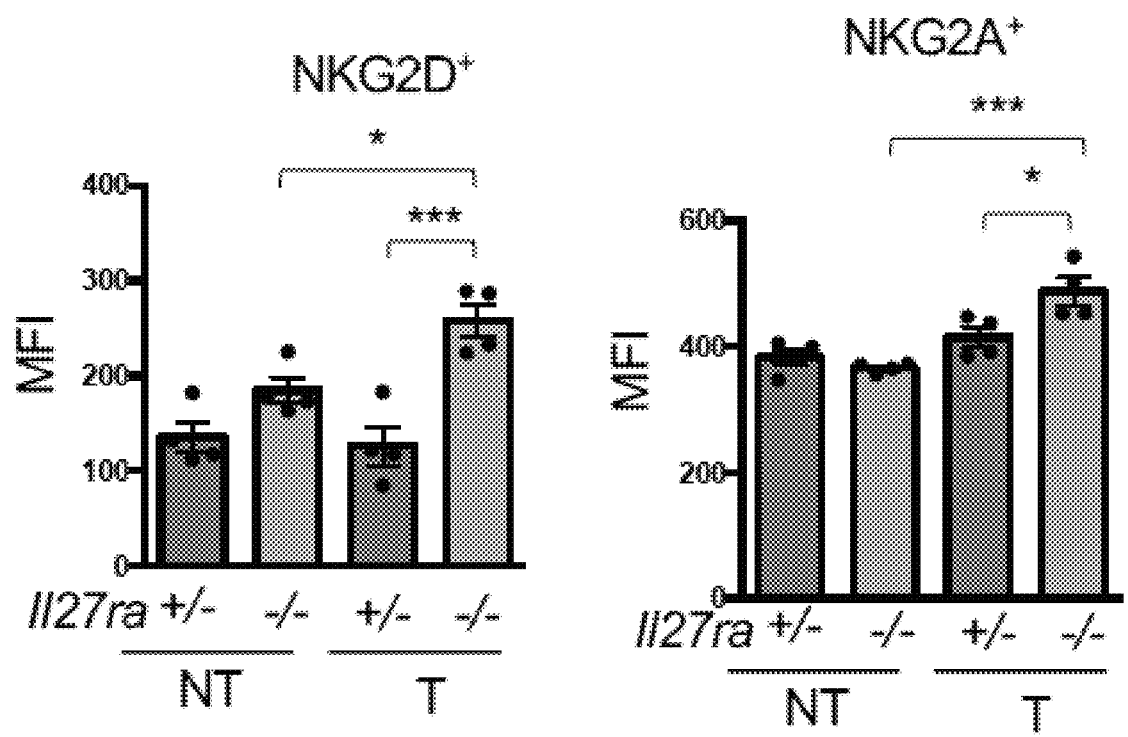
Figure 3B
Figure 3C

IgG @IL-27

H&E (4X)

TREATMENT OF NON-ALCOHOLIC STEATOHEPATITIS (NASH) WITH IL-27 ANTIBODY

FIELD

The present disclosure is directed, in part methods of treating non-alcoholic steatohepatitis (NASH) in a subject by administering to the subject an inhibitor of IL-27 or IL-27R.

BACKGROUND

Hepatocellular carcinoma (HCC) is the most common form of liver cancer with poor survival rate and limited treatment options (Balogh et al., J. Hepatocell. Carcinoma, 2016, 3, 41-53; and Yang et al., Nat. Rev. Gastroenterol. Hepatol., 2019, 16, 589-604). While innovative therapeutic strategies targeting tumor microenvironment and immune contexture provide hope to many cancer patients (Roma-Rodrigues et al., Int. J. Mol. Sci., 2019, 20; and Zhong et al., Transl. Oncol., 2020, 13, 57-69), liver cancers remain poorly responsive to immunotherapy and continue to be highly lethal disease (Yang et al., Nat. Rev. Gastroenterol. Hepatol., 2019, 16, 589-604; and Mahipal et al., Cancers (Basel), 2019, 11). For example, despite wide clinical use of T cell activation-based immunotherapies in several cancer types (Wang et al., Immunotherapy, 2014, 6, 1265-78), only recently checkpoint inhibitors demonstrated potentially promising results in HCC (Shalapour et al., Nature, 2017, 551, 340-345). Preventive approaches aimed at hepatitis B vaccination and hepatitis C eradication could potentially curb new HCC cases, however liver cancers caused by environmental toxins and fatty liver disease are clearly on the rise (El-Serag, Gastroenterology, 2012, 142, 1264-73; and Wallace et al., Expert Rev. Gastroenterol. Hepatol., 2015, 9, 765-79).

Chronic liver inflammation induced by infections, alcohol or obesity drives chronic injury and promotes compensatory proliferation of transformed hepatocytes leading to enhanced HCC onset (Park et al., Cell, 2010, 140, 197-208). While anti-cancer immune responses play an important tumor-restrictive role, it remains to be determined how they are regulated by the inflammatory entities in HCC (Schreiber et al., Science, 2011, 331, 1565-1570).

Irrespective of its etiology, HCC development is accompanied by the accumulation of various immune cells, which could contribute to cancer progression via the production of pro-inflammatory cytokines such as IL-6, IL-1, TNF and IL-17 (Ringelhan et al., Nat. Immunol., 2018, 19, 222-32). Cytokine signaling can enable HCC growth by activating proto-oncogenic transcription factors such as NF-κ3 and STAT3 in transformed hepatocytes and HCC cells (Park et al., Cell, 2010, 140, 197-208; Ringelhan et al., Nat. Immunol., 2018, 19, 222-32; Lan et al., J. Autoimmunity, 2009, 32, 43-51; and Ma et al., Cancer Res., 2014, 74, 1969-82). On the other hand, the presence of cytotoxic or IFN-γ producing T cells could suppress tumor growth (Garnelo et al., Gut, 2017, 66, 342-351). Moreover, liver microenvironment is uniquely enriched in Natural Killer (NK) cells, capable of tissue immunosurveillance and anti-tumorigenic functions potentially impacting liver cancer development (Jenne et al., Nat. Immunol., 2013, 14, 996-1006; and Tian et al., Hepatology, 2013, 57, 1654-1662). During HCC development number and activation of liver NK cells gradually declines due to yet unidentified mechanism probably related to specific signals originating from tumor microenvironment and chronic exposure to cancer cells (Cai et al., Clin. Immunol., 2008, 129, 428-437). The mechanisms that drive functional suppression of NK cells and undermine such innate anti-cancer immune responses remains incompletely understood.

Interleukin (IL)-27 is a member of the IL-6/IL-12 cytokine superfamily and is an important regulator of immune responses (Yoshida et al., Immunological Reviews, 2008, 226, 234-247). The IL-27 receptor (IL-27R) is expressed by some non-hematopoietic cells and by multiple immune cell subsets, including NK cells (Yoshida et al., Annu. Rev. Immunol., 2015, 33, 417-443). IL-27R signals primarily via STAT1 and STAT3 (Yoshida et al., Immunological Reviews, 2008, 226, 234-247), amongst which STAT3 is hepatocyte-intrinsic driver of HCC (Gao et al., J. Hepatol., 2012, 57, 430-441). IL-27 was shown to have a broad anti-inflammatory role in infectious and chronic immune-mediated diseases (Stumhofer et al., Nat. Immunol., 2006, 7, 937-945; Koltsova et al., Circulation Res., 2012, 111, 1274-1285; and Hirase et al., Amer. J. Physiol., 2013, 305, H420-429). IL-27R ablation leads to elevated production of pro-inflammatory cytokines, including IL-17A and IL-6 (Koltsova et al., Circulation Res., 2012, 111, 1274-1285; and Sasaoka et al., Amer. J. Physiol. Gastrointest. Liver Physiol., 2011, 300, G568-576). In vitro and in vivo experiments revealed that IL-27 can directly control LAG-3, TIM-3, PD-1 and TIGIT inhibitory molecules expression in T cells (Chihara et al., Nature, 2018, 558, 454-459). While immunomodulatory effects by IL-27 were shown in various pathophysiological models (Diveu et al., J. Immunol., 2009, 182, 5748-5756; Huber et al., Int'l Immunol., 2008, 20, 223-234; Morishima et al., J. Biomed. Biotechnol., 2010, 605483; and Hunter et al., Immunity, 2012, 37, 960-969), the context-dependent and cell type specific underlying mechanisms remain incompletely understood. The protective role of IL-27 and its receptor signaling in cancer has been suggested based on its anti-inflammatory role in inflammatory diseases and studies using subcutaneous cell line transplants (Salcedo et al., J. Immunol., 2004, 173, 7170-7182; Salcedo et al., J. Immunol., 2009, 182, 4328-4338; and Natividad et al., PLoS One, 2013, 8, e57469), however the role of IL-27R signaling in cancer development in vivo has not been thoroughly addressed.

SUMMARY

The present disclosure provides methods of treating non-alcoholic steatohepatitis (NASH) in a subject, the methods comprising administering to the subject an inhibitor of IL-27 or IL-27R.

BRIEF DESCRIPTION OF THE DRAWINGS

FIGS. 1A, 1B, 1C, 1D, 1E, 1F, 1G, 1H, 1I, and 1J: IL-27R signaling is implicated in liver cancer development. (1A) Representative images of IL-27R expression in human HCC as determined by IHC staining. (1B) TCGA provisional data on disease-free Kaplan-Meier estimate (disease free status since initial treatment) relative to IL27RA expression. (1C) Correlation between IL27RA expression and HCC stage in patients based on TCGA data. (1D) Il27ra$^{+/-}$ and Il27ra$^{-/-}$ mice received DEN at postnatal day 15. Cancer development was analyzed at 10 months of age. Representative images of macroscopic and microscopic view of livers with developed tumors. (1E) Tumor load and tumor number in Il27ra$^{+/-}$ (n=15) and Il27ra$^{-/-}$ (n=12) mice. (1F) Concentration of ALT in sera from Il27ra$^{+/-}$ (n=8) and Il27ra$^{-/-}$ (n=6)

Figure 1A:
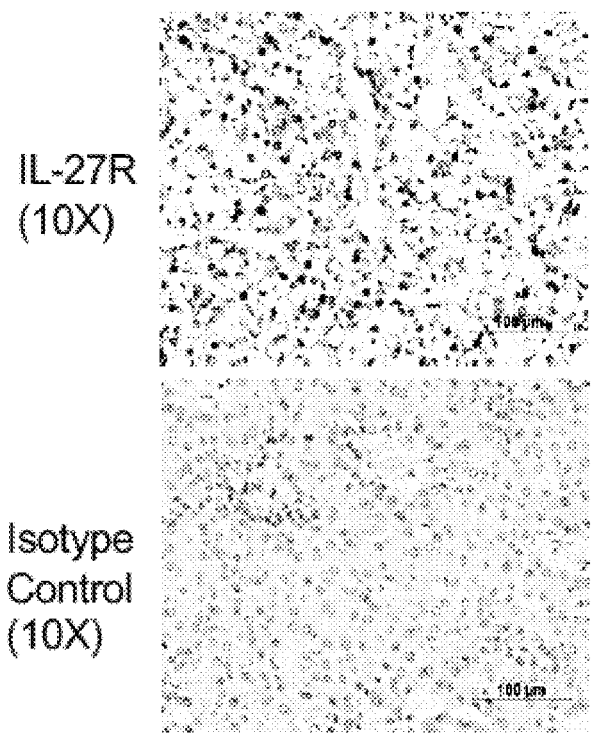

tumor-bearing 10-month-old mice. (1G) Relative gene expression of inflammatory marker Lcn2 in non-tumor and tumor tissues from Il27ra$^{+/-}$ (n=6) and Il27ra$^{-/-}$ (n=6) mice. Gene expression was first normalized to Rpl32 then to gene expression in non-tumor tissue from Il27ra$^{+/-}$ mice. (1H) Representative images and quantification of Ki67 staining of HCC sections from DEN-treated Il27ra$^{+/-}$ (n=4) and Il27ra$^{-/-}$ (n=4) mice. (1I) Relative gene expression of proliferation marker Cyclin D (Ccnd1) in tumors from Il27ra$^{+/-}$ (n=6) and Il27ra$^{-/-}$ (n=6) mice. Gene expression was first normalized to Rpl32 then to gene expression in tumors from Il27ra$^{+/-}$ mice. (1J) Representative images and quantification of pERK1/2 staining of HCC sections from DEN-received Il27ra$^{+/-}$ (n=4) and Il27ra$^{-/-}$ (n=4) mice. $p<0.01$, log-rank (Mantel-Cox) test (1B); *$p<0.001$, Chi-square test (1C). Data are mean±SEM from at least 3 independent experiments. *$p<0.05$, $p<0.01$, *$p<0.001$, unpaired Student's t-test (two-tailed) (1E, 1F, 1H-1J); $p<0.01$, *$p<0.001$, Tukey's multiple comparisons test (1G).

FIGS. 2A, 2B, 2C, 2D, 2E, 2F, and 2G: IL-27R signaling impairs NK cell accumulation and cytotoxicity. Heatmap (2A) and KEGG pathway analysis (2B) of differentially expressed genes in tumors from DEN-treated Il27ra$^{+/-}$ (n=6) and Il27ra$^{-/-}$ (n=6) mice as determined by NanoString ($p<0.05$). Single cell suspensions of non-tumor and tumor tissues from Il27ra$^{+/-}$ (n=8) and Il27ra$^{-/-}$ (n=8) DEN-injected 10-month-old mice were stained for Live/Dead, CD45, TCRβ, CD8α, CD4, NK1.1, CD11b, Ly6G, Ly6C, F4/80, Granzyme B and analyzed by FACS. (2C) Percentage of CD8α$^+$TCRβ$^+$ and CD4$^+$TCRβ$^+$ cells, and macrophages. (2D) Representative FACS plots of NK cells in non-tumor and tumor tissue. (2E) Percentage of NK cells and (2F) Granzyme NK cells as determined by intracellular staining of non-tumor and tumor tissue from Il27ra$^{+/-}$ (n=6) and Il27ra$^{-/-}$ (n=6) mice. (2G) Relative gene expression of Cxcr6 and Gzmb in NK cells sorted by FACS from non-tumor and tumor tissue from Il27ra$^{+/-}$ (n=6) and Il27ra$^{-/-}$ (n=6) mice. Gene expression was first normalized to Rpl32 then to gene expression of NK cells in non-tumor tissue from Il27ra$^{-/-}$ mice. Data are mean±SEM from at least 3 independent experiments. *$p<0.05$. $p<0.01$, *$p<0.001$, Tukey's multiple comparisons test.

FIGS. 3A, 3B, 3C, 3D, 3E, 3F, 3G, and 3H: IL-27R signaling augments NK cell activation and maturation. Single cell suspensions of non-tumor and tumor tissue from DEN-injected Il27ra$^{+/-}$ (n=4) and Il27ra$^{-/-}$ (n=4) 10-month-old mice were stained for Live/Dead, CD45, TCRβ, NK1.1, CD49a, CD49b, NKG2D and NKG2A. (3A) Representative histogram of NKG2D activating receptor expression. (3B) Mean fluorescence intensity and percentage of NKG2D$^+$CD49b$^+$ NK cells in non-tumor and tumor tissue. (3C) Mean fluorescence intensity and percentage of NKG2A$^+$CD49b$^+$ NK cells in non-tumor and tumor tissue. (3D) Representative histogram of Ly-49C inhibitory receptor expression. (3E) Mean fluorescence intensity and percentage of Ly-49C$^+$CD49b$^+$ NK cells in non-tumor and tumor tissue. Single cell suspensions of non-tumor and tumor tissue from DEN-injected Il27ra$^{+/-}$ (n=7) and Il27ra$^{-/-}$ (n=4) 10-month-old mice were stained for Live/Dead, CD45, TCRβ, NK1.1, CD11b, CD27 and analyzed by FACS. (3F) Representative FACS plots of NK-cell maturation based on CD11b and CD27 expression. (3G) Percentage of immature (CD11b$^-$CD27$^-$ and CD11b$^-$CD27$^+$) and mature (cytotoxic/cytokine secreting CD11b$^+$CD27$^+$ and terminally mature CD11b$^+$CD27$^-$) NK cells. (3H) Relative gene expression of Gzmb, Prf1, Ifng, Klrk1, Tnfsf10, Faslg and Cxcr6 in NK cells purified by MACS from spleens of WT mice (n=5) and stimulated in vitro with rIL-27. Gene expression was first normalized to Klrb1c then to gene expression in untreated condition. Data are mean±SEM from at least 3 independent experiments. *$p<0.05$, $p<0.01$, *$p<0.001$, Tukey's multiple comparisons test (3B, 3C, 3E, 3G); $p<0.01$, *$p<0.001$, ****$p<0.0001$, unpaired Student's t-test (two-tailed) (3H).

FIGS. 4A, 4B, 4C, and 4D: IL-27R signaling controls stress molecules and MHC I expression. (4A) Relative gene expression of stress molecules Raet1a and H60b in non-tumor and tumor tissue from DEN-injected Il27ra$^{+/-}$ (n=4) and Il27ra$^{-/-}$ (n=4) mice. Gene expression was first normalized to Rpl32 then to gene expression in non-tumor tissue from Il27ra$^{+/-}$ mice. (4B) Relative gene expression of Raet1a and H60b in DEN-derived HCC cells treated in vitro with rIL-27. Gene expression was first normalized to Rpl32 then to gene expression in untreated condition. Single cell suspensions of tumor tissue from DEN-injected Il27ra$^{+/-}$ and Il27ra$^{-/-}$ 10-month-old mice were stained for Live/Dead, CD45, CD11b, CD31, TER-119, H-2K$^b$ and analyzed by FACS. (4C) Representative histogram of MHC I expression on tumor cells from Il27ra$^{+/-}$ and Il27ra$^{-/-}$ mice. (4D) Relative gene expression of MHC I processing gene Tap1 in tumor tissue of Il27ra$^{+/-}$ (n=4) and R27ra$^{-/-}$ (n=4) mice. Gene expression was first normalized to Rpl32 then to that in tumor tissue of Il27ra$^{+/-}$ mice. Data are mean±SEM from at least 3 independent experiments. Tukey's multiple comparisons test (A); *$p<0.05$, $p<0.01$, *$p<0.001$, unpaired Student's t-test (two-tailed) (4B, 4D).

FIGS. 5A, 5B, 5C, 5D, 5E, 5F, 5G, 5H, 5I, 5J, and 5K: IL-27R signaling promotes HCC tumor growth in NASH model. 8-week-old MUP-uPA$^+$Il27ra$^{+/-}$ and MUP-uPA$^+$Il27ra$^{-/-}$ mice were fed a WD for 8 months. (5A) Representative images of macroscopic and microscopic view of livers with developed tumors. (5B) Tumor load and tumor number of MUP-uPA$^+$Il27ra$^{+/-}$ (n=7) and MUP-uPA$^+$Il27ra$^{-/-}$ (n=7) male mice. (5C) Relative gene expression of Ccnd1 in tumor tissue from MUP-uPA$^+$Il27ra$^{+/-}$ (n=6) and MUP-uPA$^+$Il27ra$^{-/-}$ (n=6) male mice. Gene expression was first normalized to Rpl32 then to gene expression in tumors from MUP-uPA$^+$Il27ra$^{+/-}$ mice. (5D) Representative images and quantification of collagen content (collagen-red, other tissues-yellow) determined by Van Gieson staining of liver sections from MUP-uPA$^+$Il27ra$^{+/-}$ (n=3) and MUP-uPA$^+$Il27ra$^{-/-}$ (n=3) male mice. (5E) Relative gene expression of Lcn2 in non-tumor and tumor tissue from MUP-uPA$^+$Il27ra$^{+/-}$ (n=6) and MUP-uPA$^+$Il27ra$^{-/-}$ (n=6) female and male mice. Gene expression was first normalized to Rpl32 then to gene expression in non-tumor tissue from MUP-uPA$^+$Il27ra$^{+/-}$ mice. Single cell suspensions of non-tumor and tumor tissue of MUP-uPA$^+$Il27ra$^{+/-}$ (n=6) and MUP-uPA$^+$Il27ra$^{-/-}$ (n=4) WD-fed 10-month-old female and male mice were stained for Live/Dead, CD45, TCRβ, CD8α, CD4, NK1.1 and analyzed by FACS. (5F) Percentage of CD8α$^+$TCRβ$^+$ and CD4$^+$TCRβ$^+$ cells. (5G) Percentage of NK cells. Relative gene expression of Cxcr6, Gzmb (5H) and Raet1a, H60b (5I) in non-tumor and tumor tissue from MUP-uPA$^+$Il27ra$^{+/-}$ (n=6) and MUP-uPA$^+$Il27ra$^{-/-}$ (n=6) female and male mice. Gene expression was first normalized to Rpl32 then to gene expression in non-tumor tissue from MUP-uPA$^+$Il27ra$^{+/-}$ mice. Single cell suspensions of tumor tissue from WD-fed MUP-uPA$^+$Il27ra$^{+/-}$ (n=4) and MUP-uPA$^+$Il27ra$^{-/-}$ (n=4) 10-month-old female and male mice were stained for Live/Dead, CD45, CD11b, CD31, TER-119, MHC I and analyzed by FACS. (5J) Representative histogram and mean fluorescent intensity of MHC I expression on tumor cells. (5K) Relative gene expression of Tap1 in tumors from MUP-uPA$^+$Il27ra$^{+/-}$ (n=6) and MUP-uPA$^+$ Il27ra$^{-/-}$ (n=6) female and male mice. Gene expression was first normalized to Rpl32 then to that in tumor tissue from MUP-uPA$^+$Il27ra$^{+/-}$ mice. Data are mean±SEM from at least 3 independent experiments. *p<0.05. p<0.01, *p<0.001, ****p<0.0001, unpaired Student's t-test (two-tailed) (5B-5D, 5J, 5K); Tukey's multiple comparisons test (5E, 5G-5I).

FIGS. 6A, 6B, 6C, 6D, 6E, and 6F: IL-27R signaling exerts its action via NK cells. DEN-treated Il27ra$^{+/-}$ and Il27ra$^{-/-}$ mice were administered with anti-NK1.1 and isotype control (IgG) for 5.5 months prior to tumor development analysis at 10 months. (6A) Representative images of macroscopic and microscopic view of livers with developed tumors. (6B) Tumor load and tumor number in IgG group: Il27ra$^{+/-}$ (n=4), Il27ra$^{-/-}$ (n=6) and @NK1.1 group: Il27ra$^{+/-}$ (n=5), Il27ra$^{-/-}$ (n=4) mice. (6C) Representative histogram and percentage of NKp46$^+$ NK cells from livers of Il27ra$^{+/-}$ (n=4) and Il27ra$^{-/-}$ (n=4) mice as determined by FACS. (6D) Relative gene expression of Nrc1 (NKp46) in NK cells purified by MACS from spleens of WT mice (n=5) and stimulated in vitro with rIL-27. Gene expression was first normalized to Klrb1c then to gene expression in untreated condition. (6E) Representative images of macroscopic and microscopic view of livers with developed tumors from Ncr1$^{+/gfp}$Il27ra$^{+/-}$ and Ncr1$^{+/gfp}$Il27ra$^{-/-}$ DEN-treated mice analyzed at 10 months of age. (6F) Tumor load and tumor number among Ncr1$^{+/gfp}$Il27ra$^{+/-}$ (n=7) and Ncr1$^{+/gfp}$Il27ra$^{-/-}$ (n=6) mice compared to Il27ra$^{+/-}$ (n=15) and Il27ra$^{-/-}$ (n=12) mice from the cohorts shown on FIG. 1E. Data are mean±SEM from at least 3 independent experiments. *p<0.05, p<0.01, **p<0.0001, unpaired Student's t-test (two-tailed).

Figure 7A:
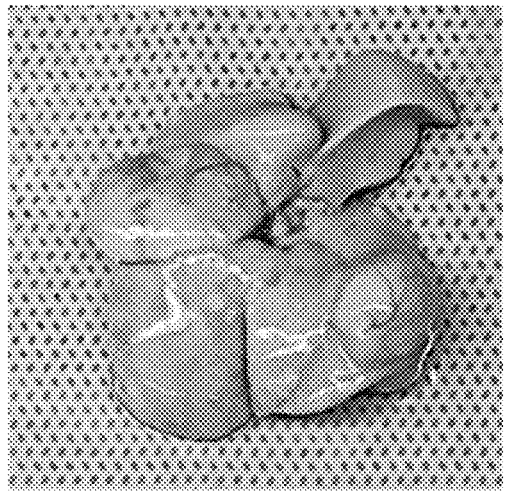
Figure 7A:
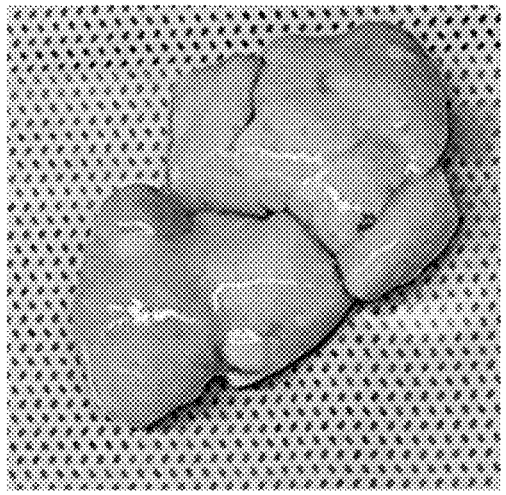
Figure 7A:
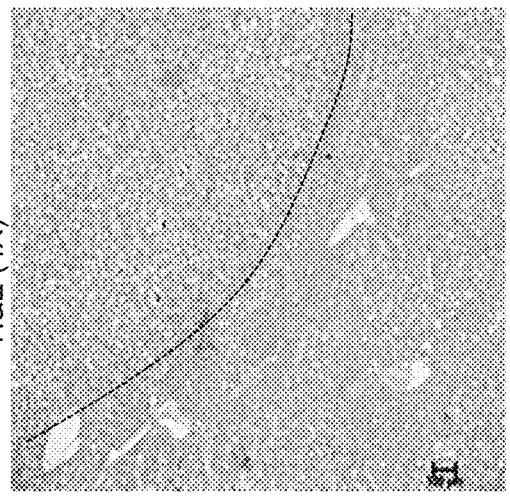
Figure 7A:
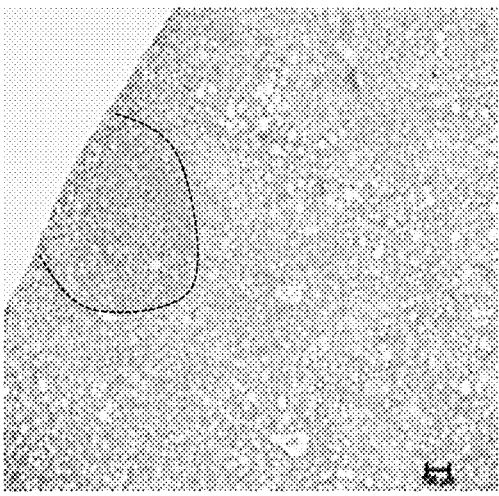
Figure 7B:
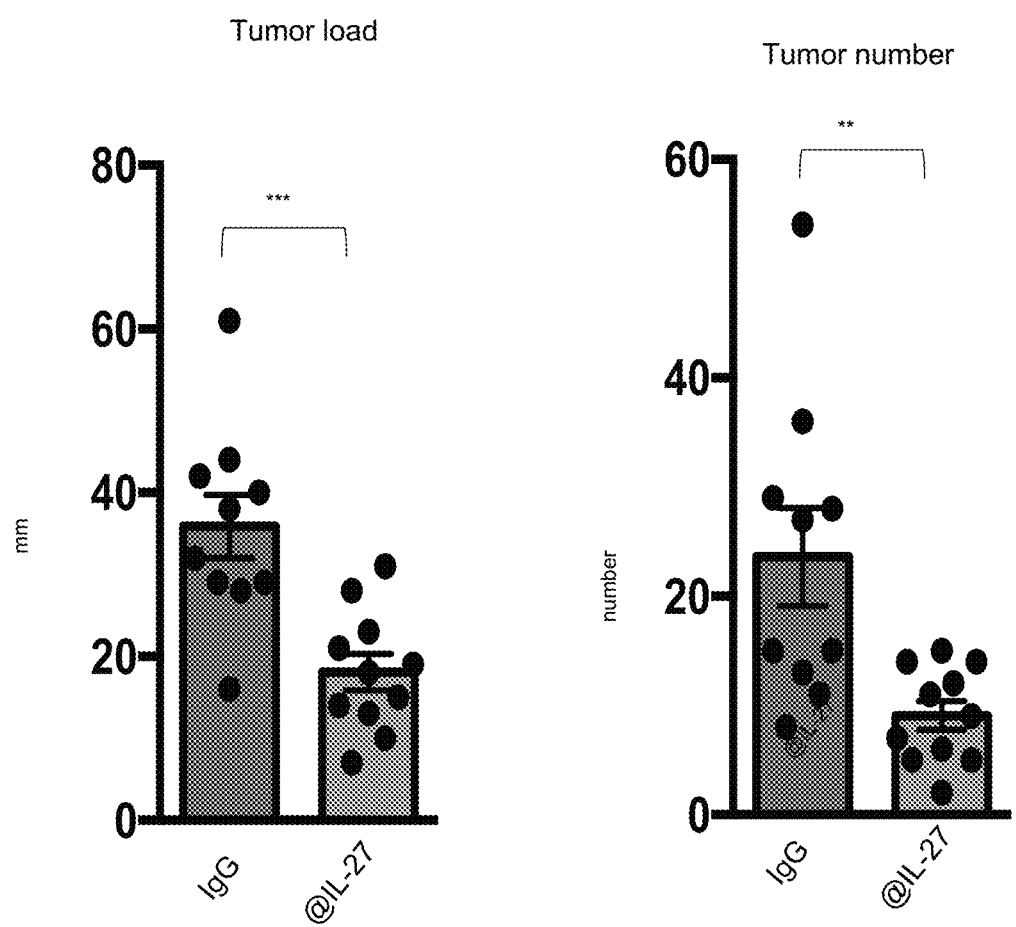
Figure 7C:
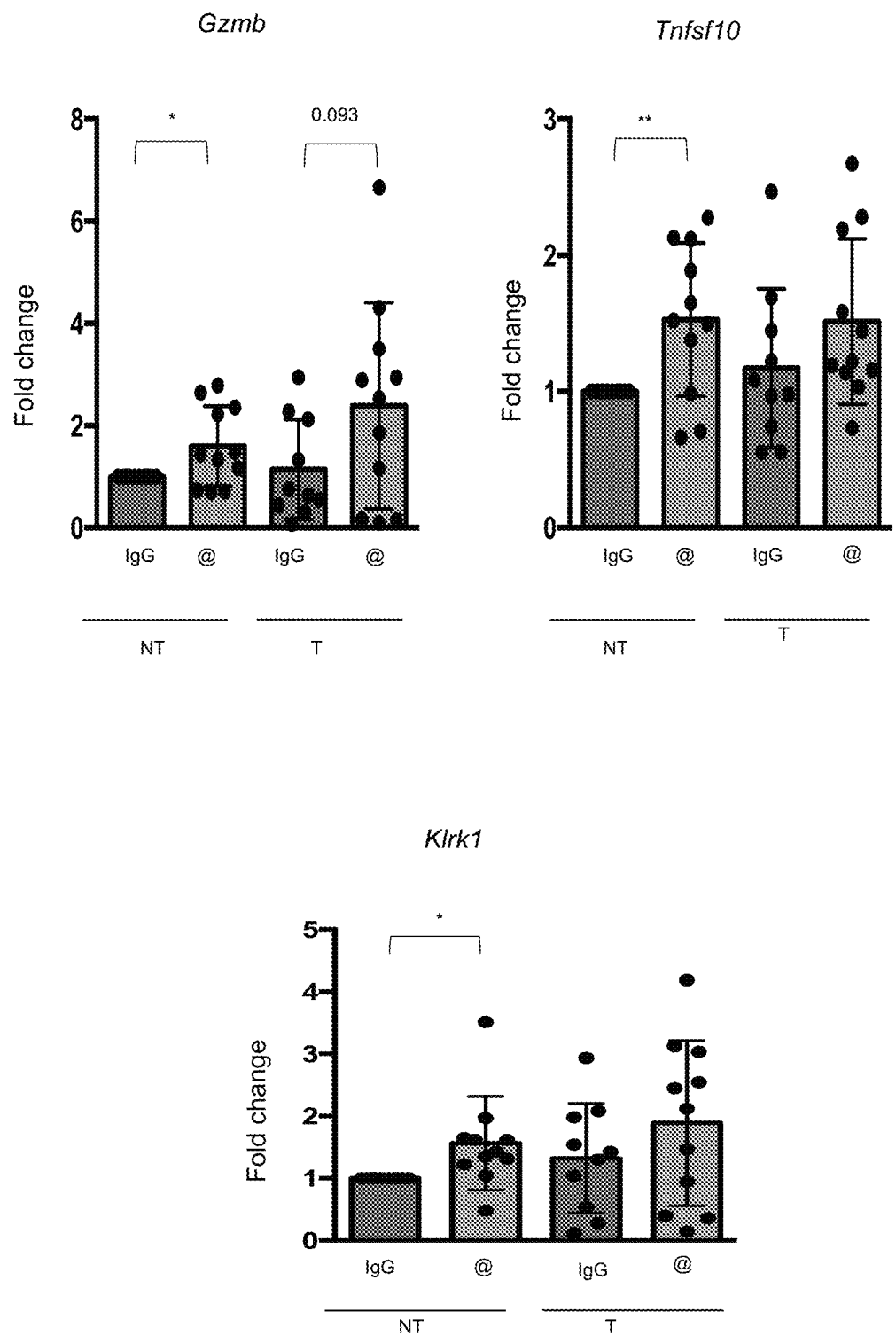

FIGS. 7A, 7B, and 7C: IL-27 neutralization suppresses NASH-driven liver cancer development. MUP-uPA$^+$ mice were fed a WD for 8 months and received either IgG isotype control or anti-IL-27 (SRF381) antibody for the last 15 weeks of WD feeding. Tumor development was analyzed at 10 months (7A) Representative images of macroscopic and microscopic view of livers with developed tumors. (7B) Tumor load and tumor number of IgG group (n=10) and anti-IL-27 (n=11) male and female mice. (7C) Relative gene expression of Gzmb, Tnfsf10 and Klrk1 in non-tumor and tumor tissue from IgG (n=10) and anti-IL-27 (n=11) female and male mice. Data are mean±SEM from 2 independent experiments. *p<0.05. p<0.01, *p<0.001, unpaired Student's t-test (two-tailed).

Figure 8A:
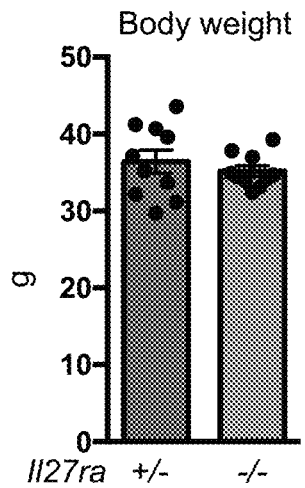
Figure 8B:
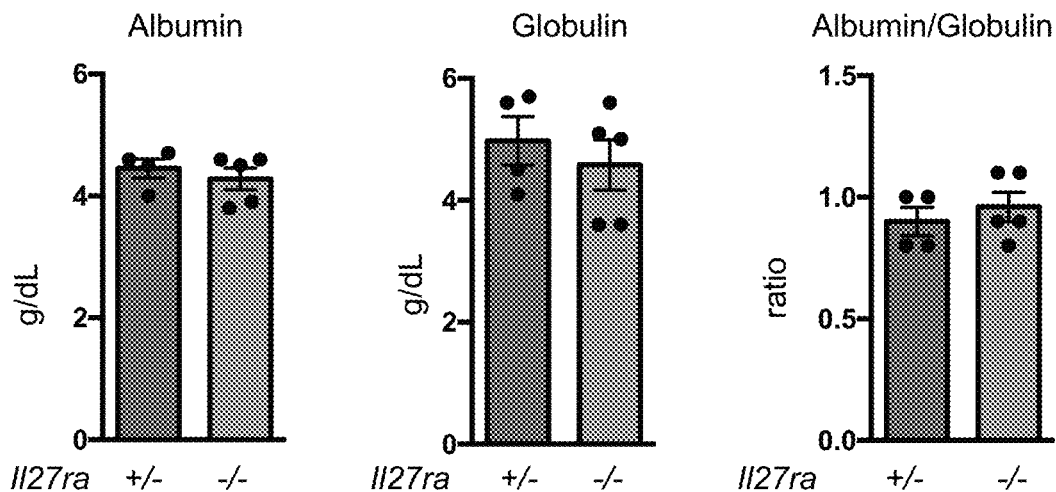
Figure 8B:
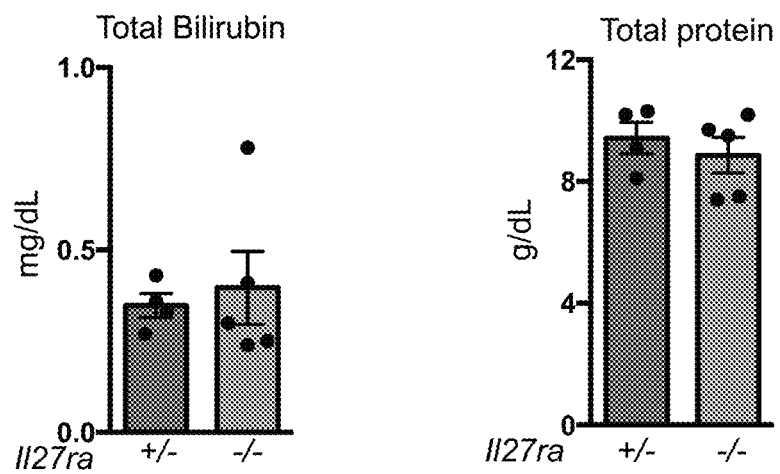

FIGS. 8A and 8B: IL-27R deficiency does not affect body weight and serum proteins (8A) Body weight of DEN-injected tumor-bearing Il27ra$^{+/-}$ (n=10) and Il27ra$^{-/-}$ (n=10) male mice. (8B) Serum analysis of DEN-injected tumor-bearing Il27ra$^{+/-}$ (n=4) and Il27ra$^{-/-}$ (n=5) male mice. Data are mean±SEM from at least 3 independent experiments from 10-month-old mice.

Figure 9A:
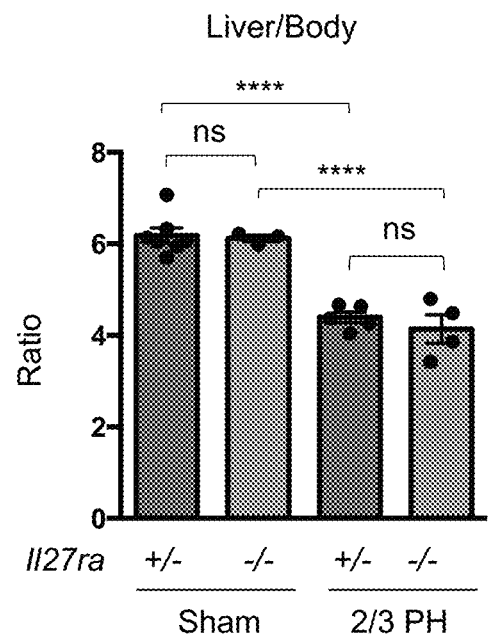
Figure 9B:
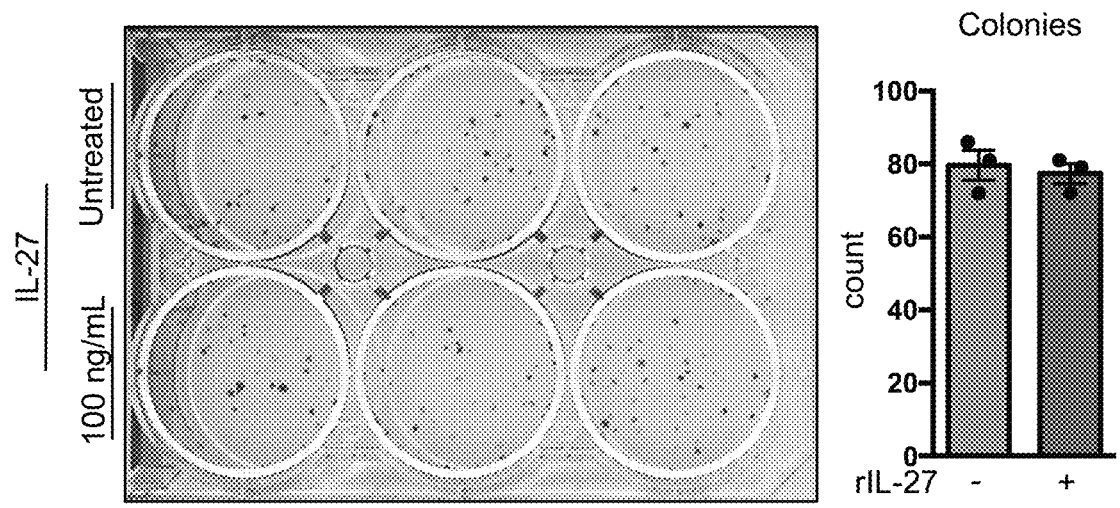
Figure 9C:
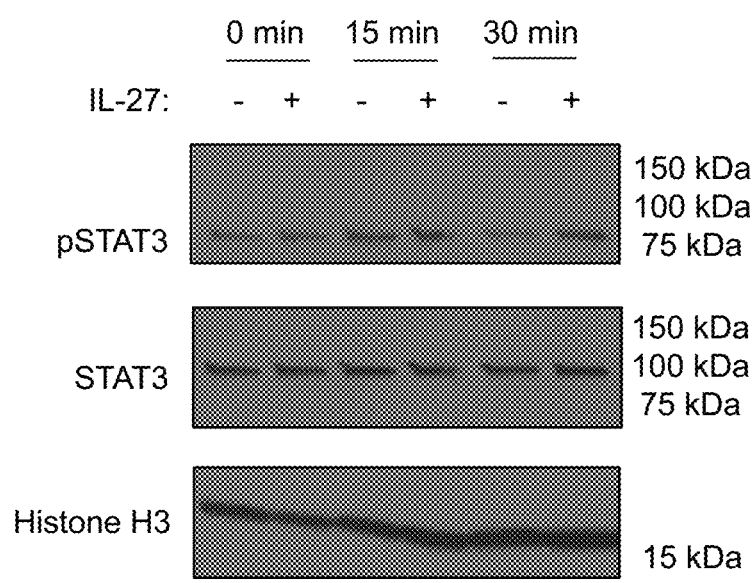
Figure 10A:
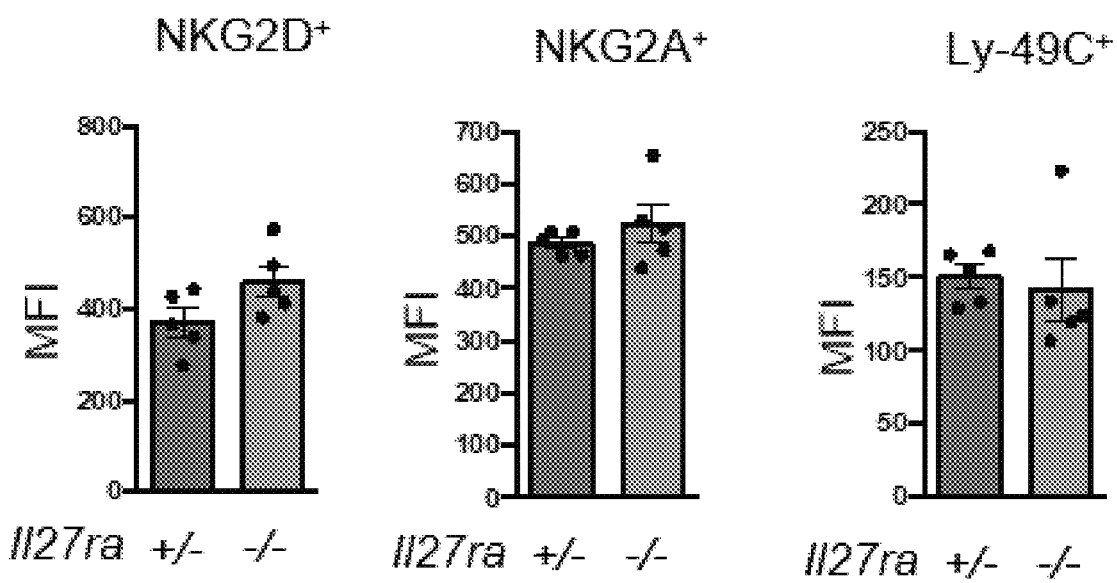
Figure 10B:
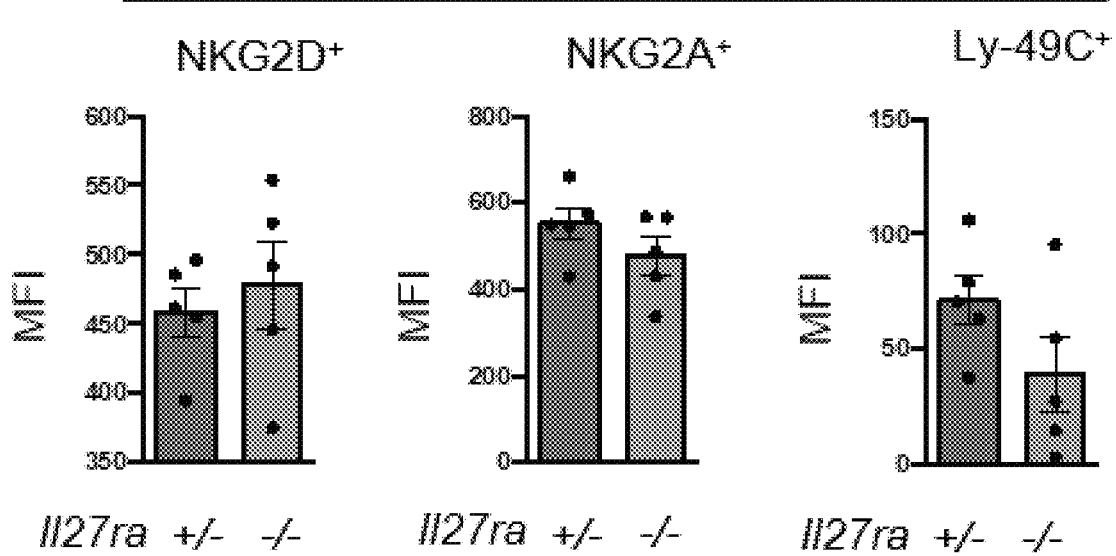
Figure 10C:
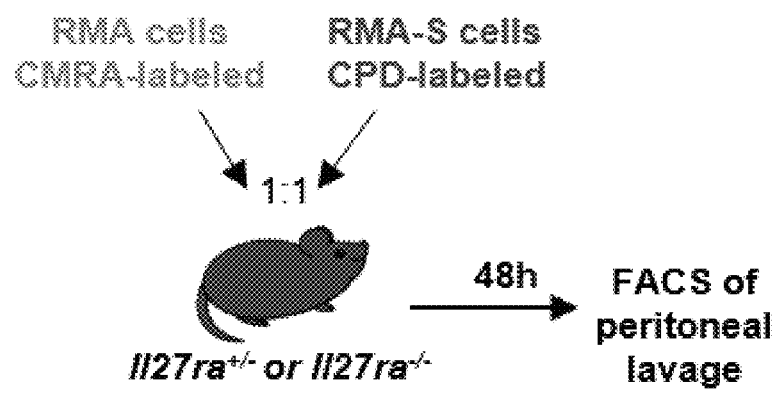
Figure 10D:
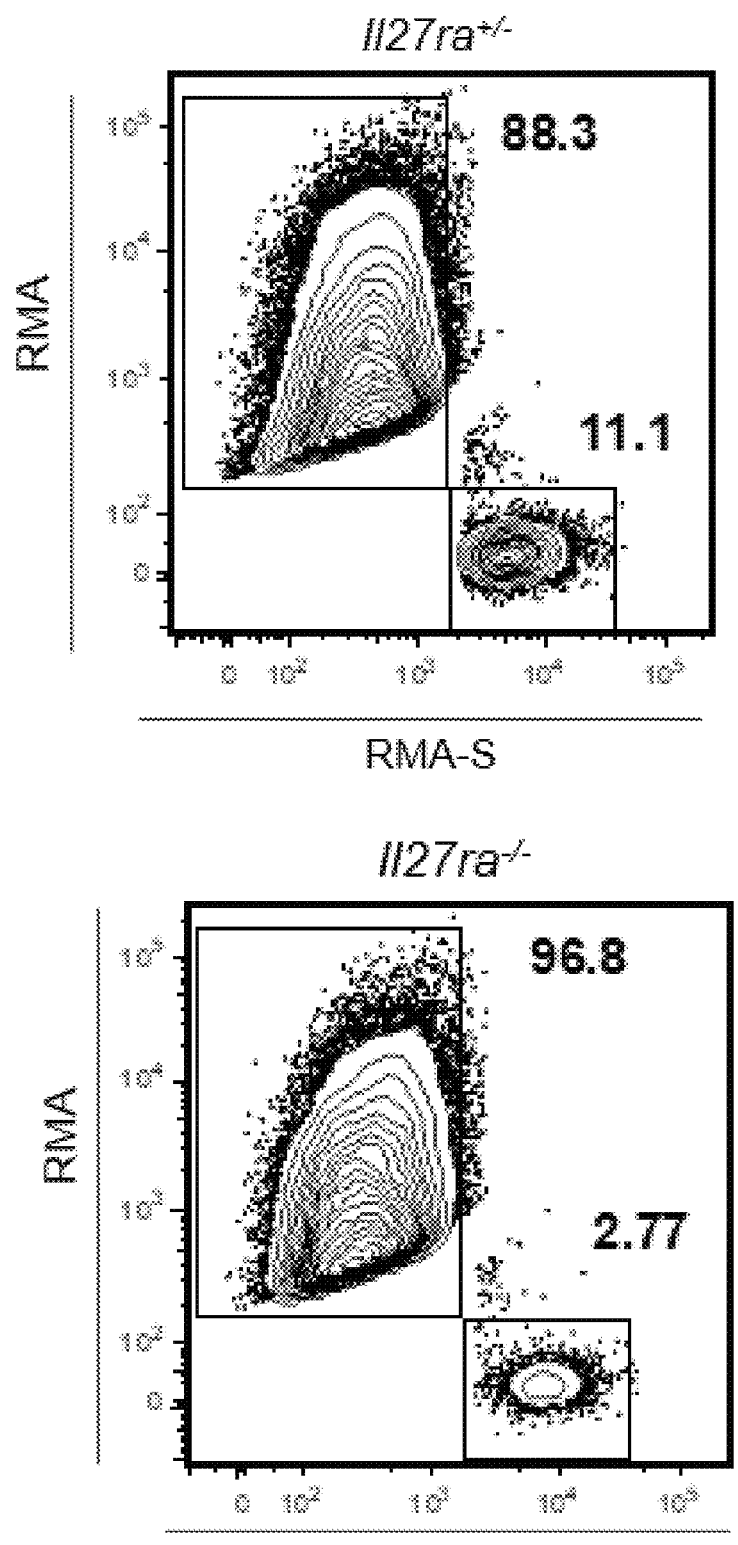
Figure 10E:
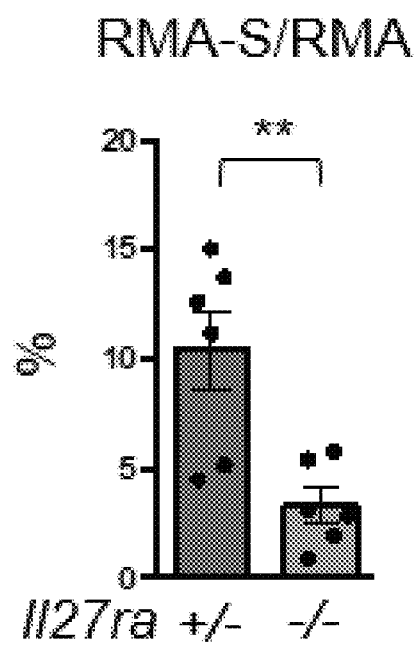
Figure 10F:
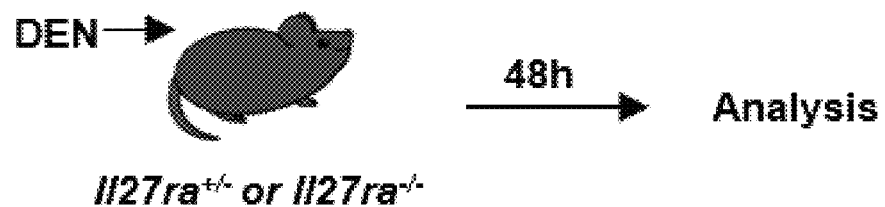
Figure 10G:
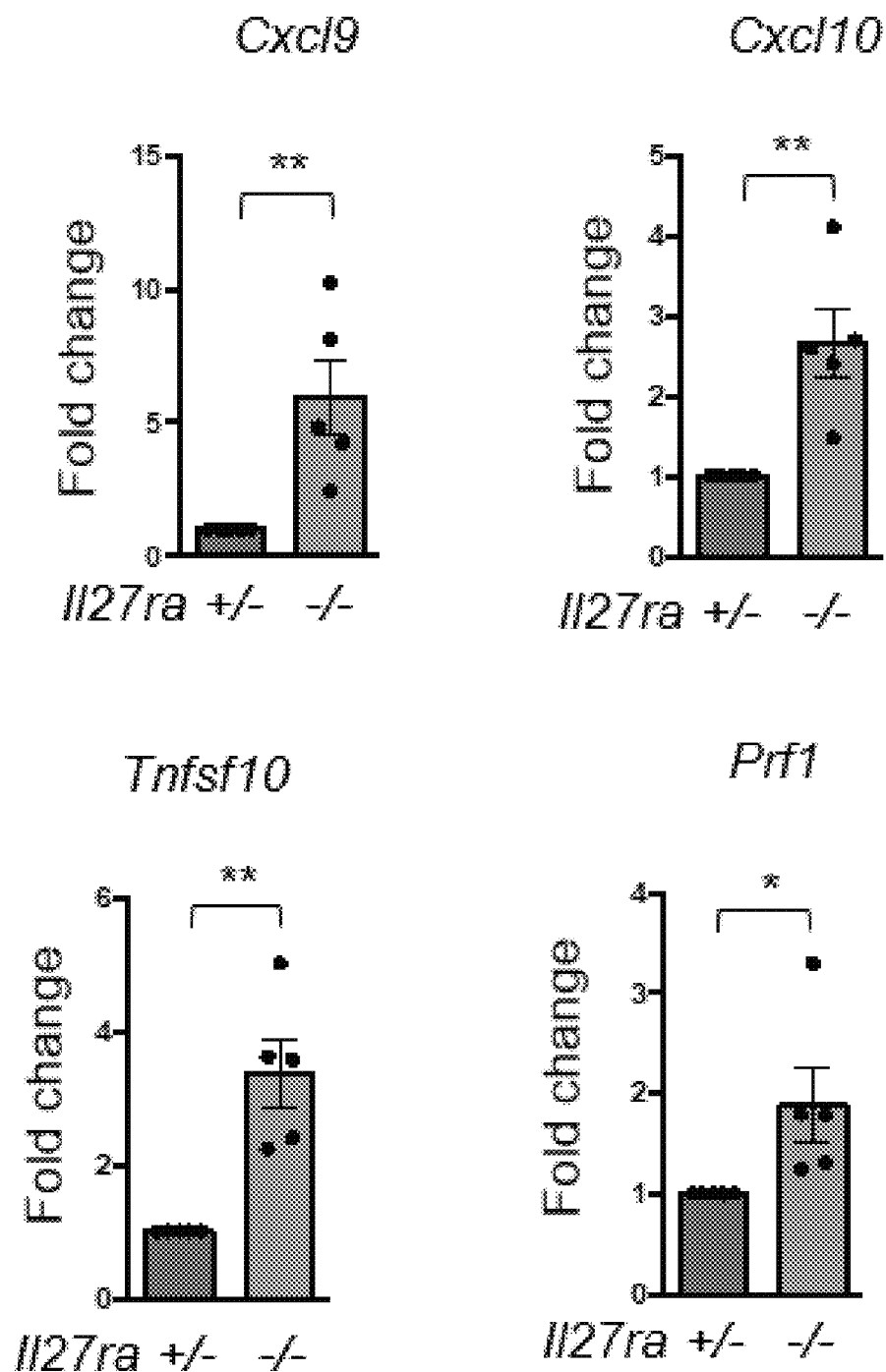
Figure 10G:
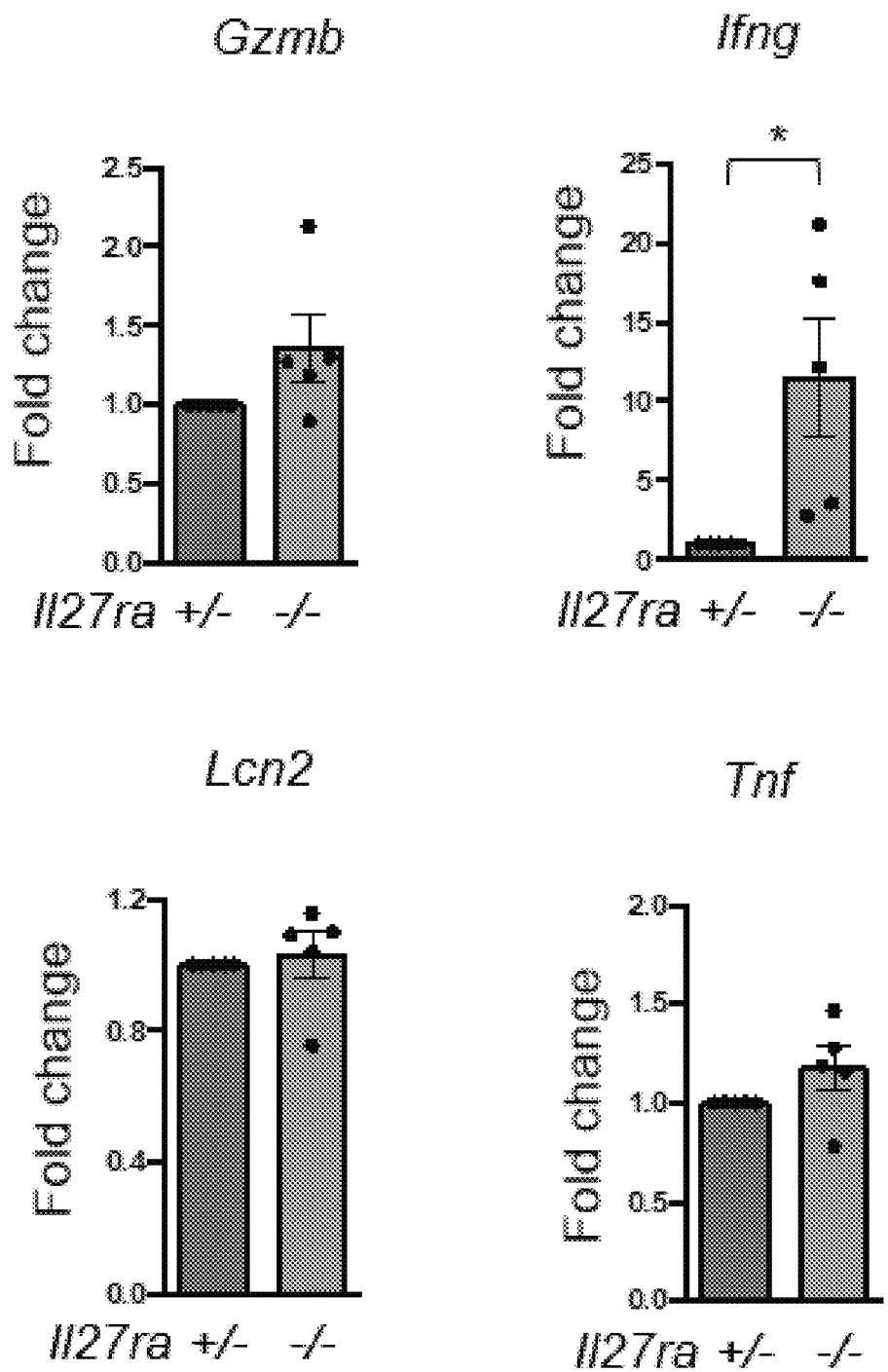

FIGS. 9A, 9B, and 9C: IL-27R deficiency does not alter liver regeneration and colony forming ability of HCC cells (9A) Liver to body weight ratio of Il27ra$^{+/-}$ (n=7) and Il27ra$^{-/-}$ (n=3) male mice sham surgery and Il27ra$^{+/-}$ (n=5) and Il27ra$^{-/-}$ (n=4) male mice subjected to ⅔ partial hepatectomy. (9B) Representative image and quantification of the colonies grown from DEN-derived HCC cells treated in vitro with rIL-27. Data are mean±SEM from at least 3 independent experiments. ****p<0.0001, Tukey's multiple comparisons test. (9C) pSTAT3 and STAT3 protein expression analysis in protein lysates of DEN-derived HCC cells treated with rIL-27 and collected at different time points (0, 15, 30 minutes).

FIGS. 10A, 10B, 10C, 10D, 10E, 10F, and 10G: IL-27R signaling is implicated into regulation of NK cell activity. Single cell suspensions of spleen and peripheral blood from DEN-Il27ra$^{+/-}$ (n=5) and Il27ra$^{-/-}$ (n=5) 10-month-old mice were stained for Live/Dead, CD45, TCRβ, NK1.1, CD49a, CD49b, NKG2D, NKG2A and analyzed by FACS. Mean fluorescence intensity of NKG2D$^+$CD49b$^+$, NKG2A$^+$CD49b$^+$ and Ly-49C$^+$CD49b$^+$ NK cells in spleens (10A) or peripheral blood (10B). (10C) Scheme of the experiment. Cell lines were dye-labelled, mixed in 1:1 ratio and i.p. injected into 8-week-old Il27ra$^{+/-}$ and Il27ra$^{-/-}$ mice, cell recovery was analyzed in 48 hours. (10D) Representative plots of RMA and RMA-S, sensitive and insensitive to NK cells killing, respectively. (10E) Percentage of RMA/RMA-S cells ratio from peritoneal lavage of Il27ra$^{+/-}$ (n=6) and Il27ra$^{-/-}$ (n=6) mice. (10F) Scheme of the experiment. 8-week-old Il27ra$^{+/-}$ and Il27ra$^{-/-}$ male mice were injected with 100 mg/kg of DEN, livers were collected for analysis in 48 hours. (10G) Relative gene expression of chemokines Cxcl9, Cxcl10, and cytotoxic molecules Tnfsf10, Prf1, Gzmb and Ifng in livers from Il27ra$^{+/-}$ (n=5) and Il27ra$^{-/-}$ (n=5) male mice. Gene expression was first normalized to Rpl32 then to gene expression in liver of Il27ra$^{+/-}$ mice. Data are mean±SEM from at least 3 independent experiments. *p<0.05, **p<0.01, unpaired Student's t-test (two-tailed).

Figure 11:
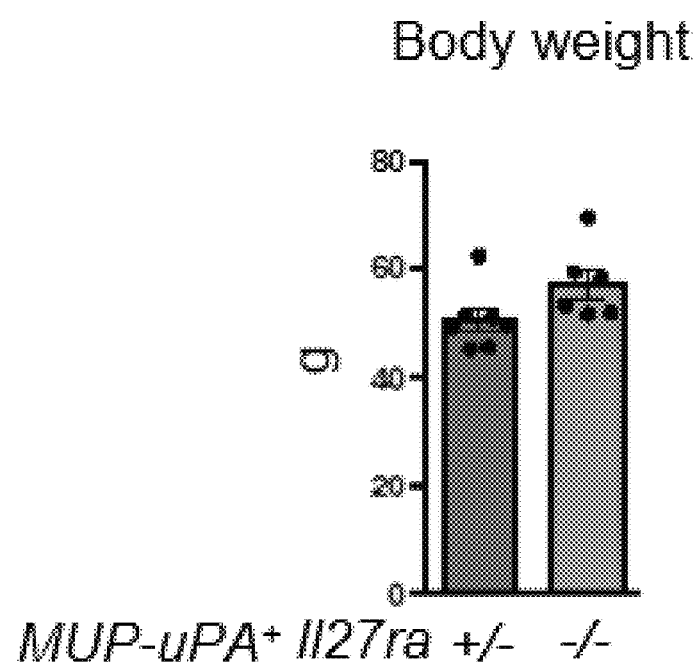

FIG. 11 shows that IL-27R deficiency does affect body weight of mice in NASH-dependent model of HCC. Body weight of WD-fed tumor-bearing mice MUP-uPA$^+$Il27ra$^{+/-}$ (n=7) and MUP-uPA$^+$Il27ra$^{-/-}$ (n=6) male mice. Data are mean±SEM from at least 3 independent experiments.

Figure 12A:
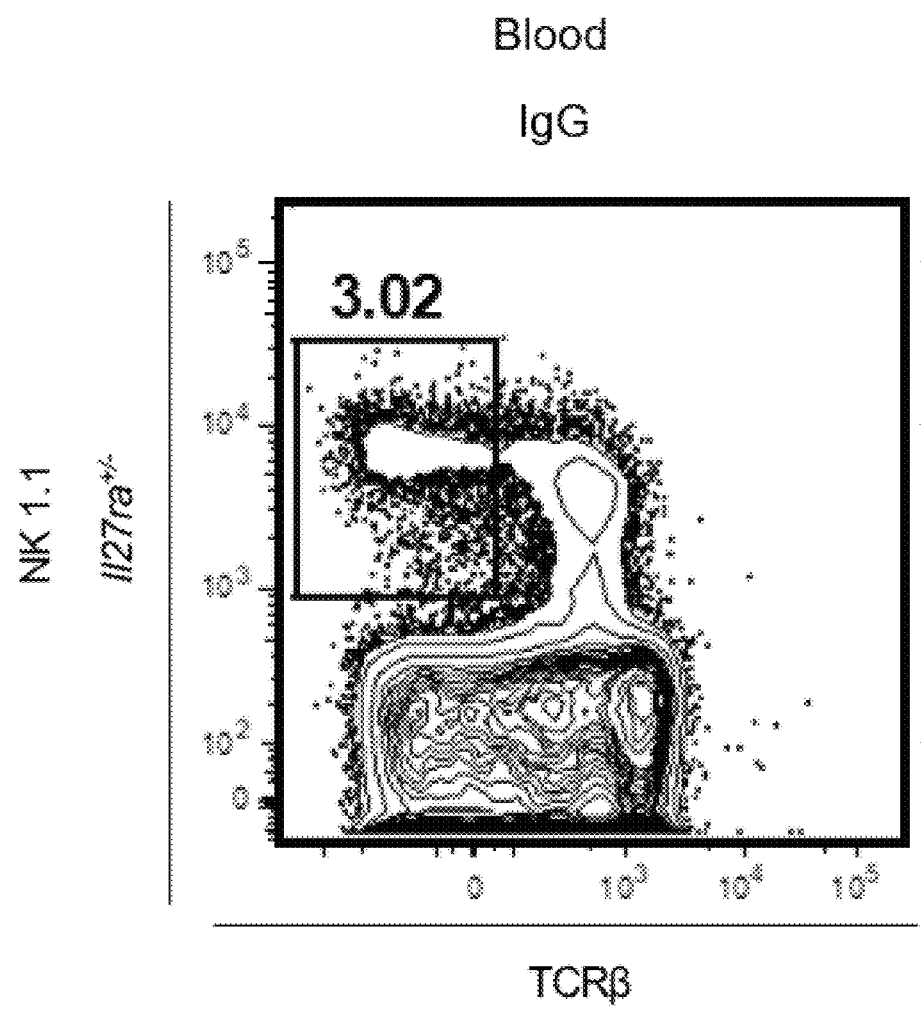
Figure 12A:
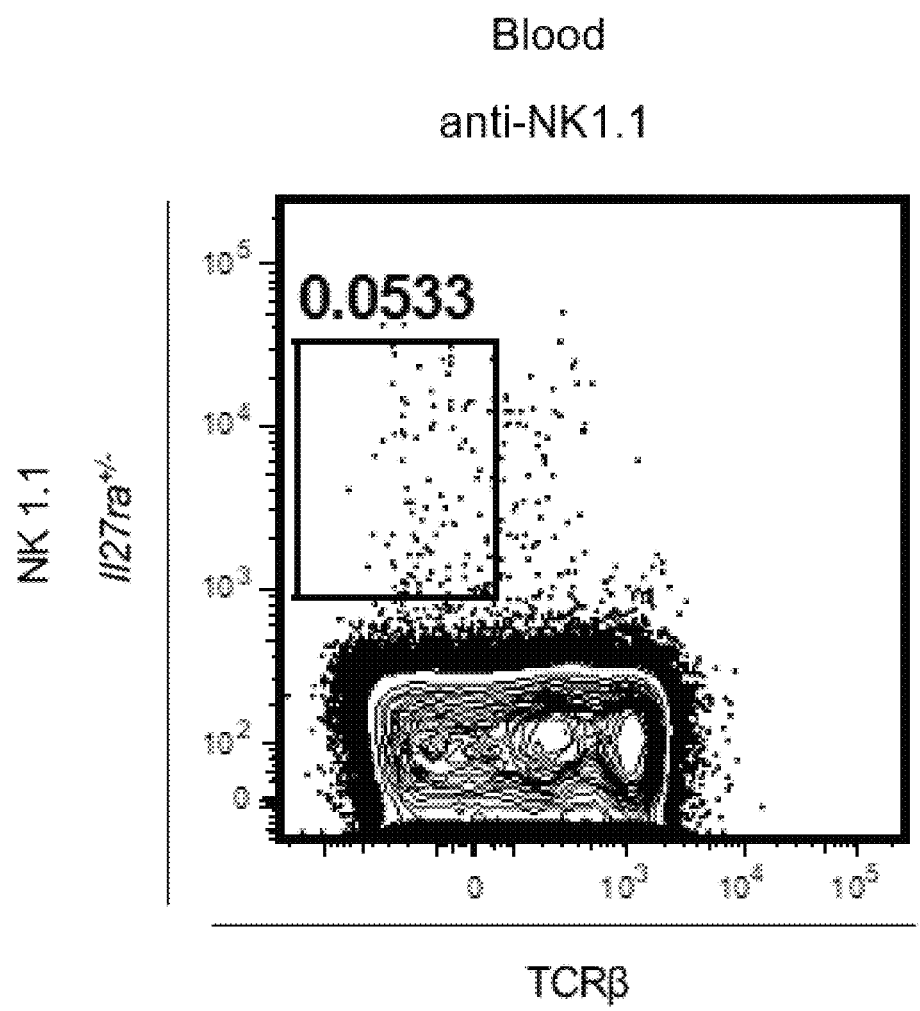
Figure 12A:
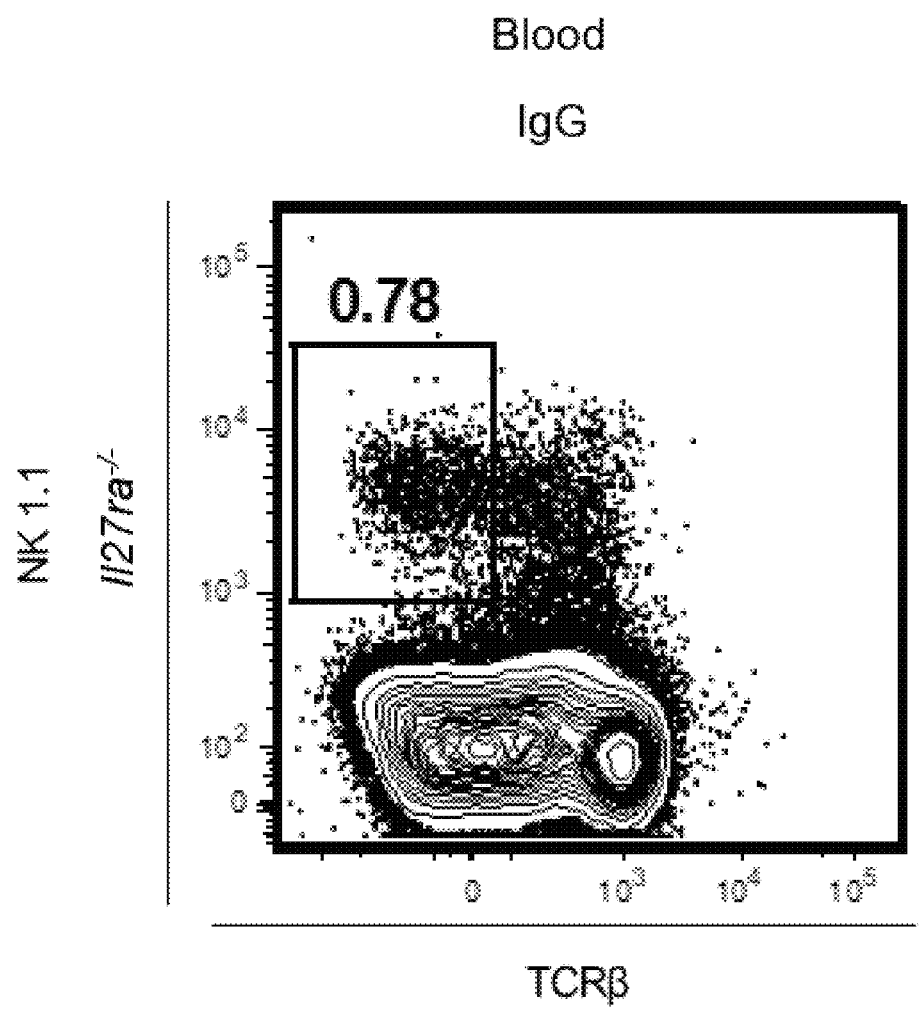
Figure 12A:
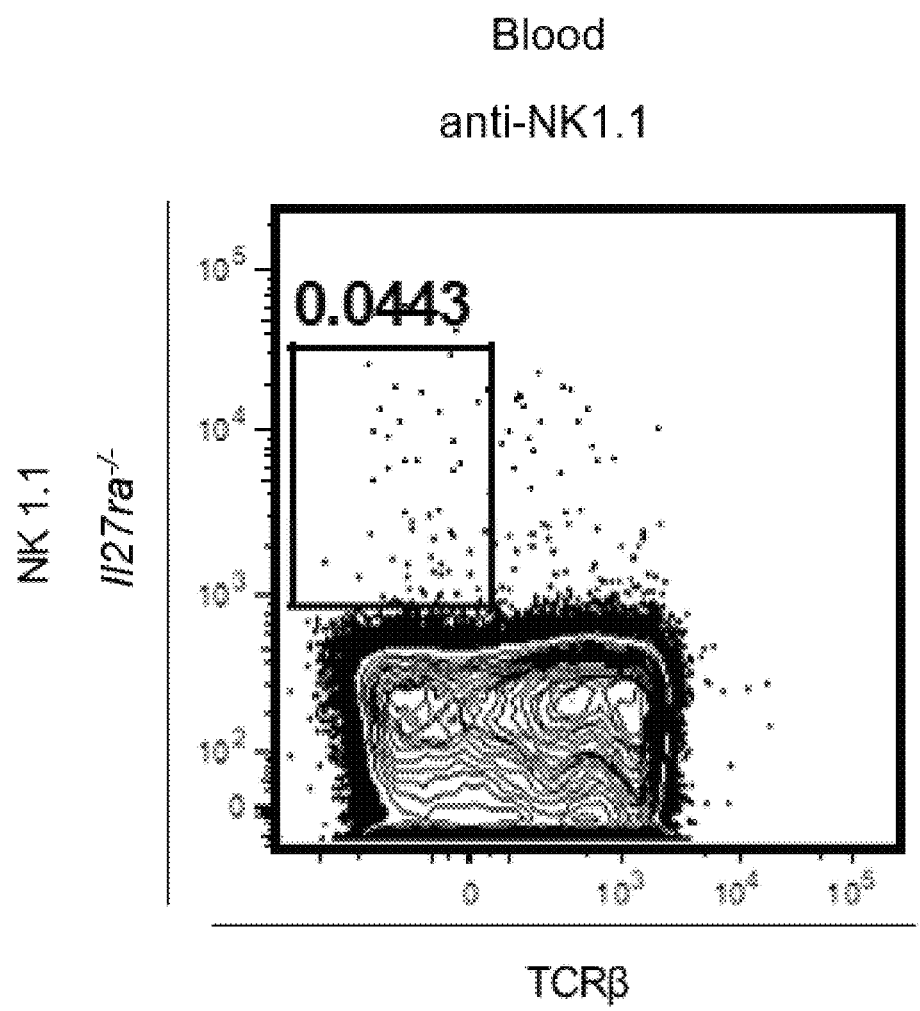
Figure 12B:
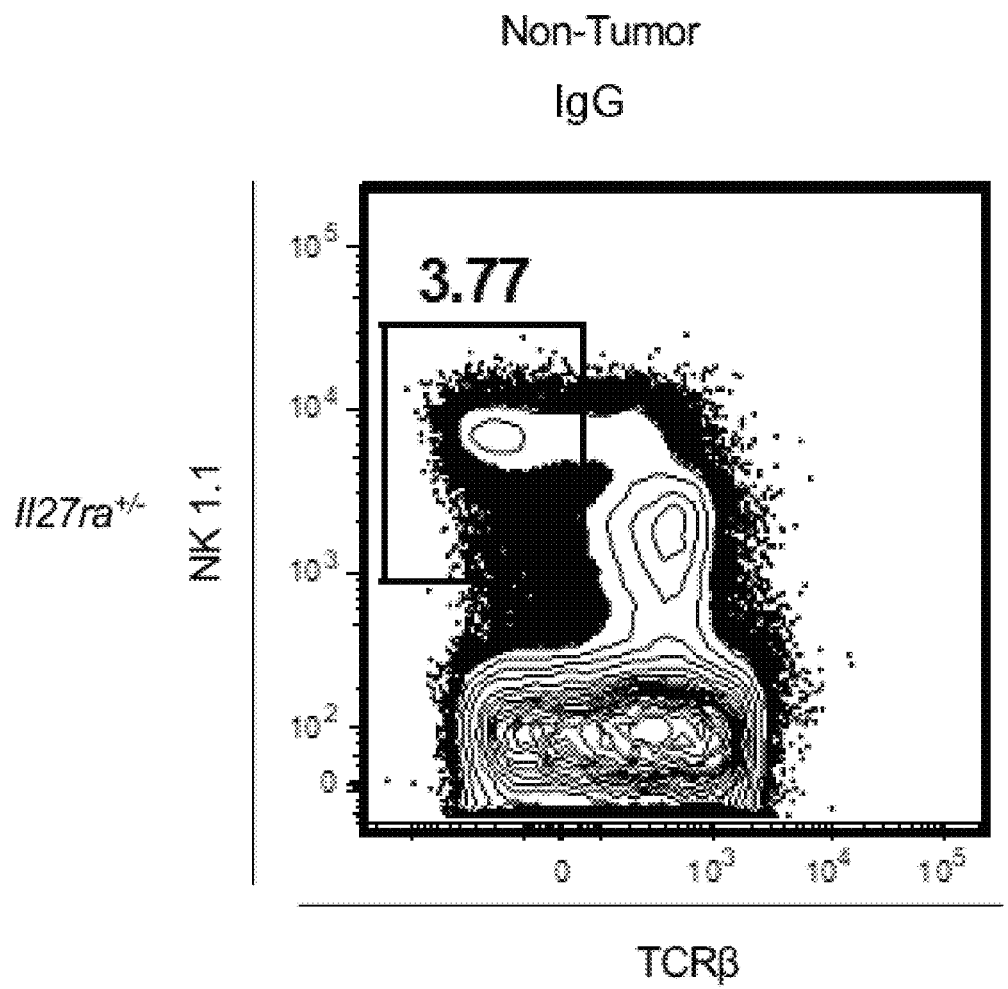
Figure 12B:
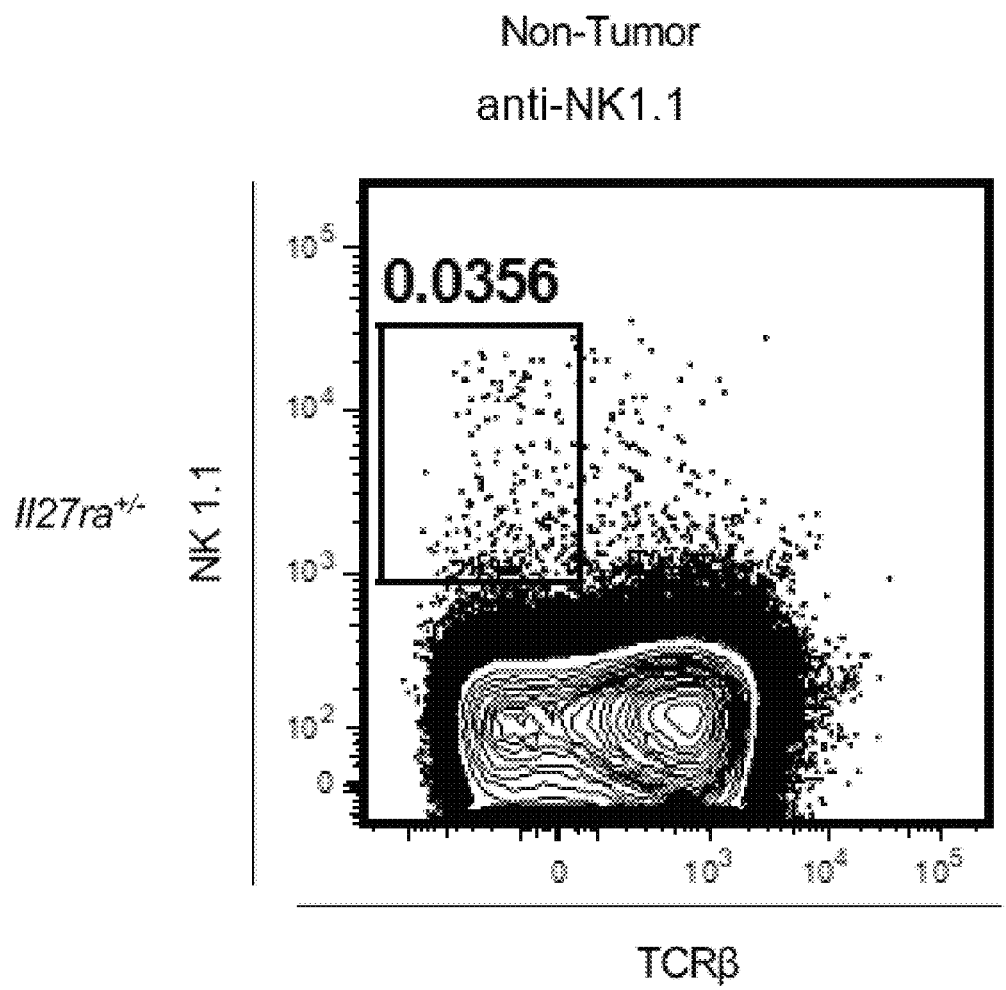
Figure 12B:
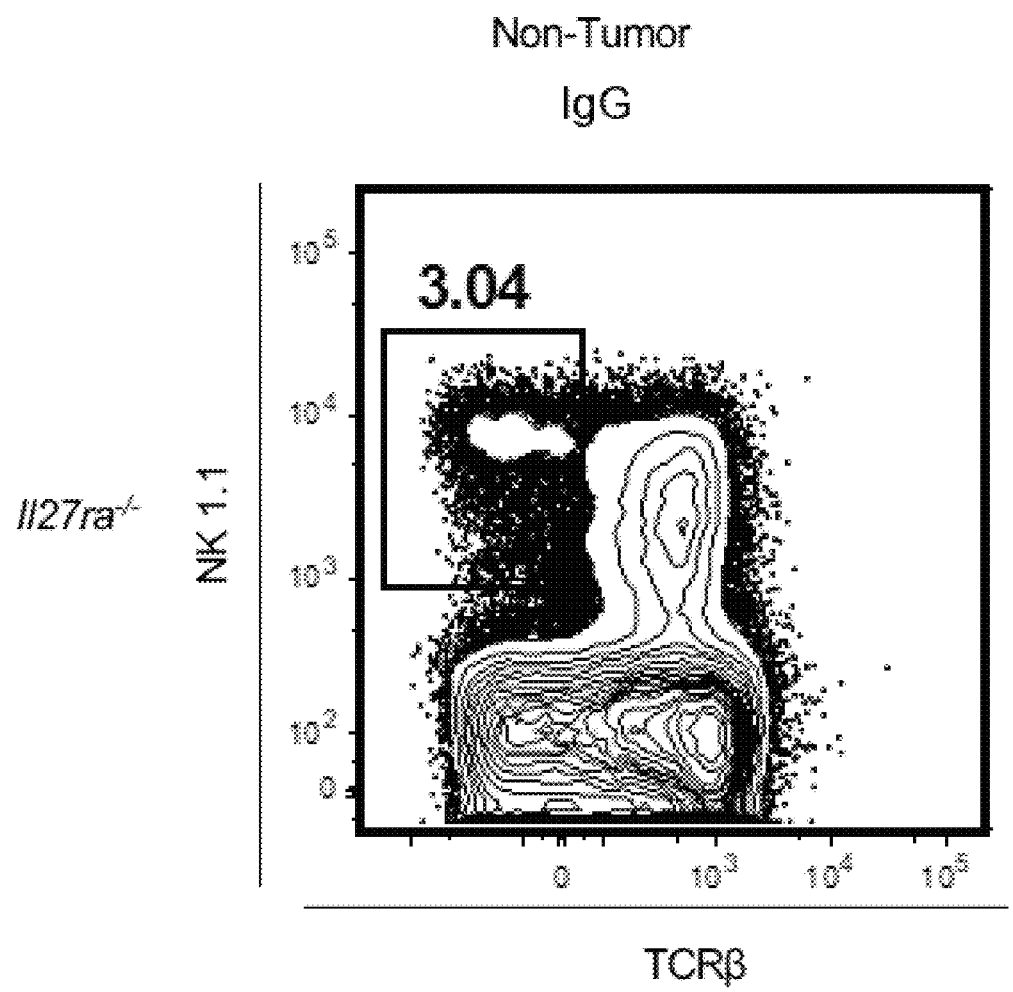
Figure 12B:
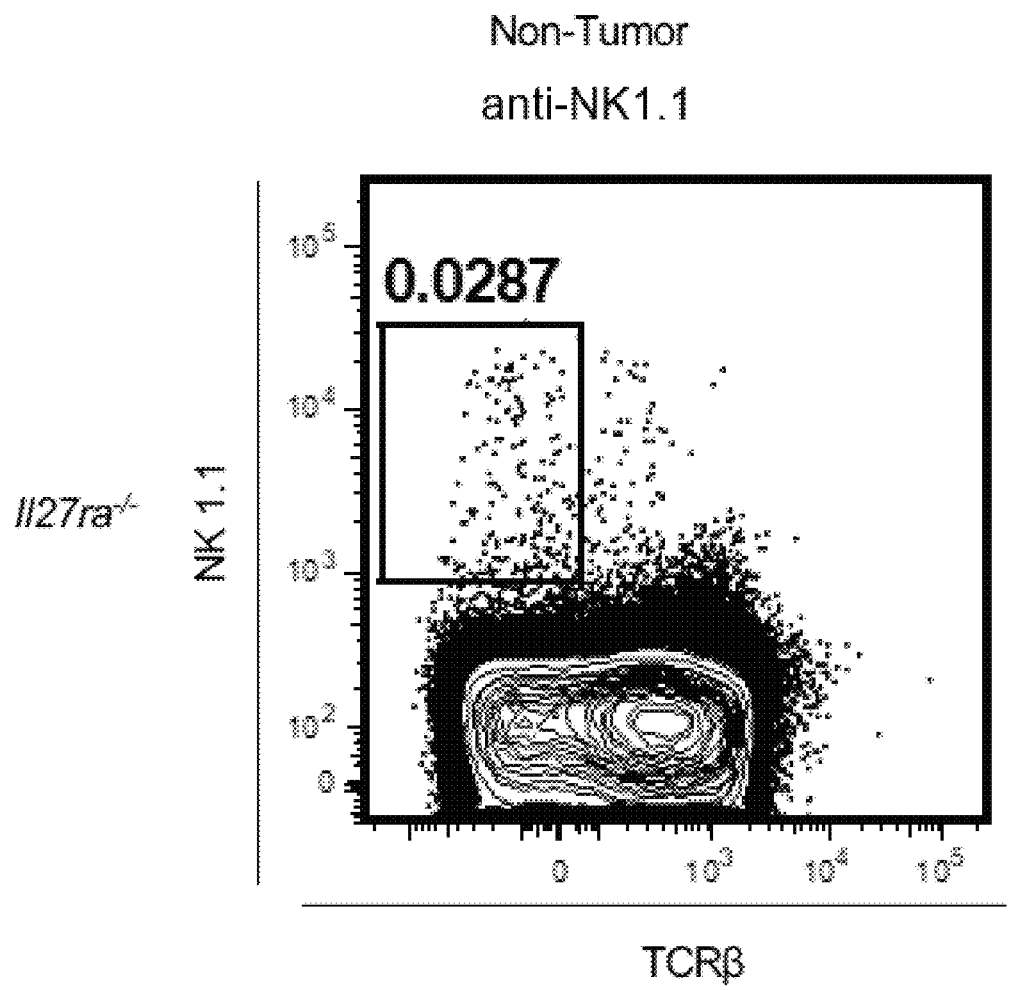
Figure 12B:
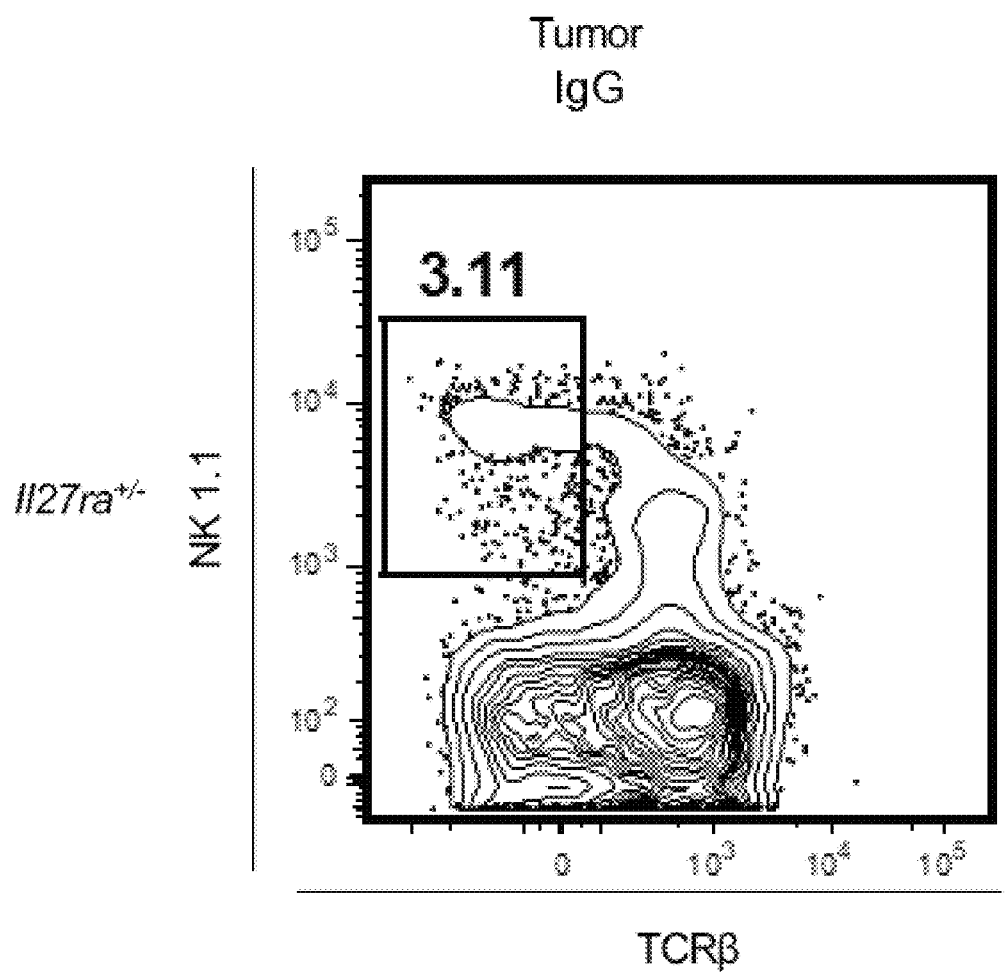
Figure 12B:
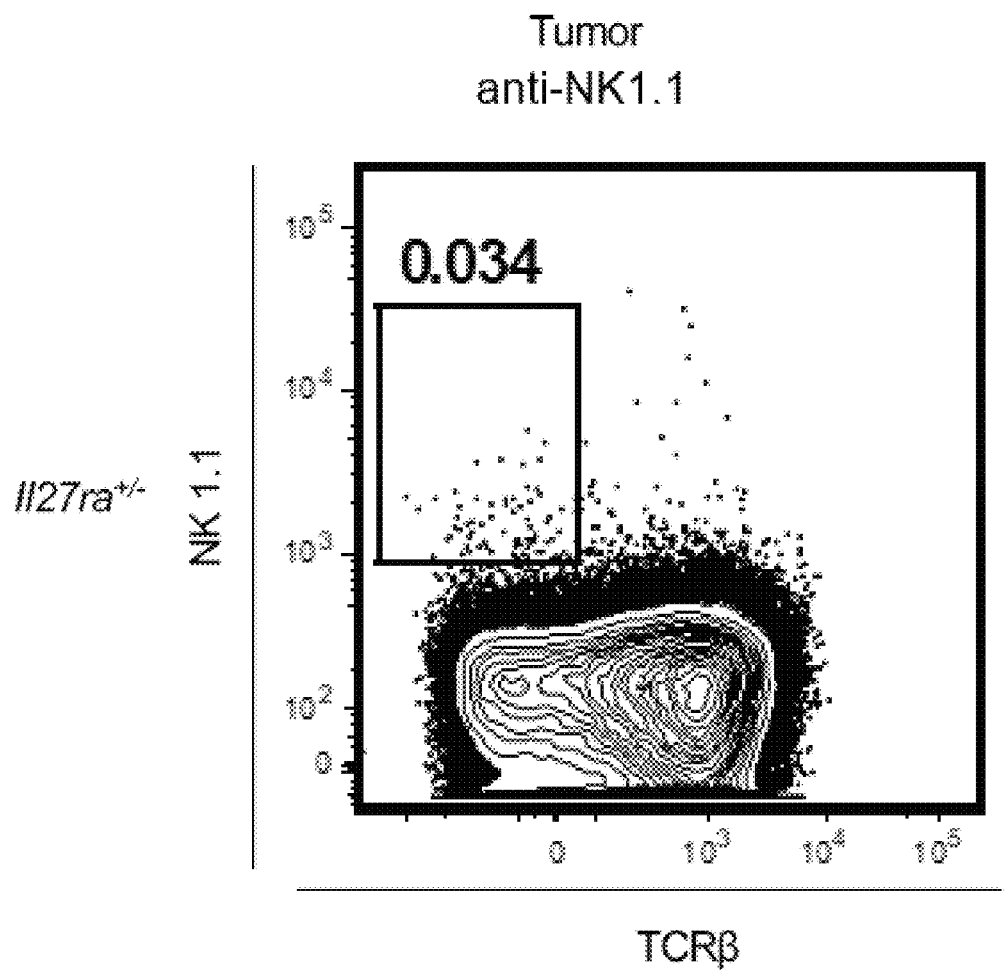
Figure 12B:
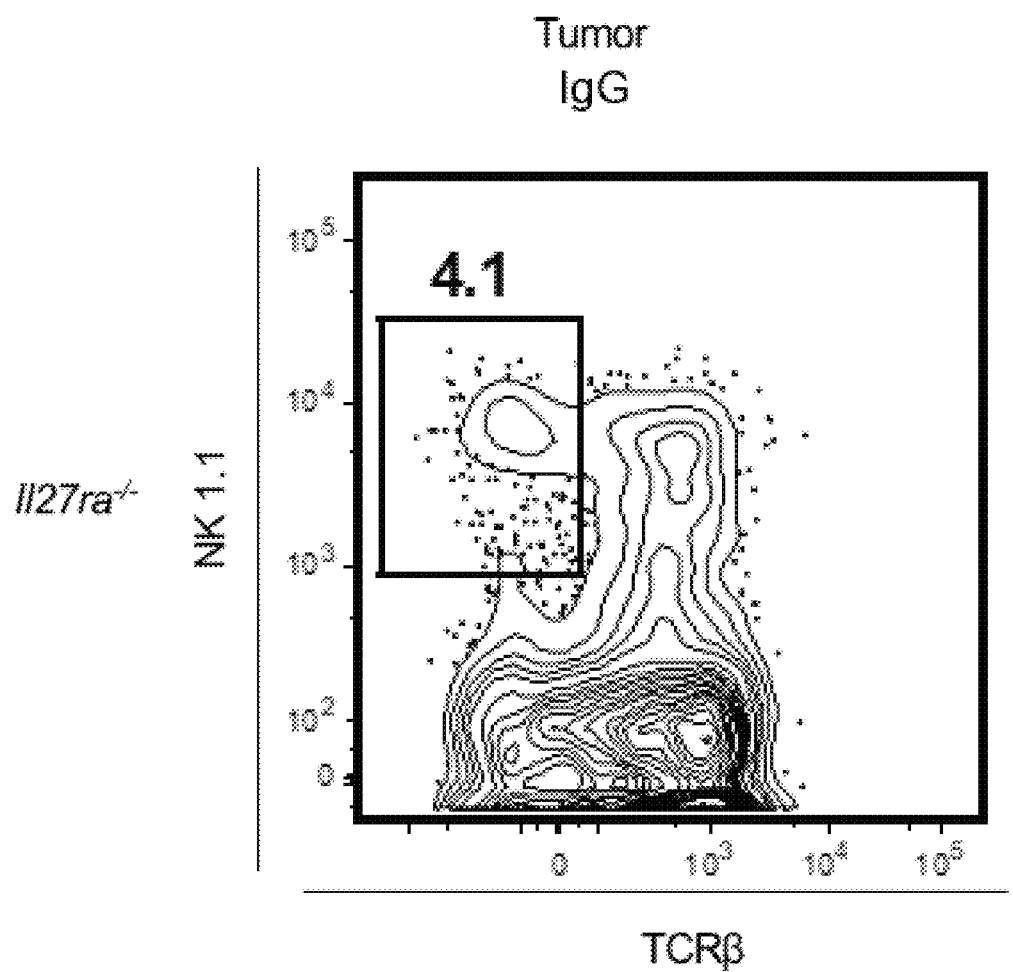
Figure 12B:
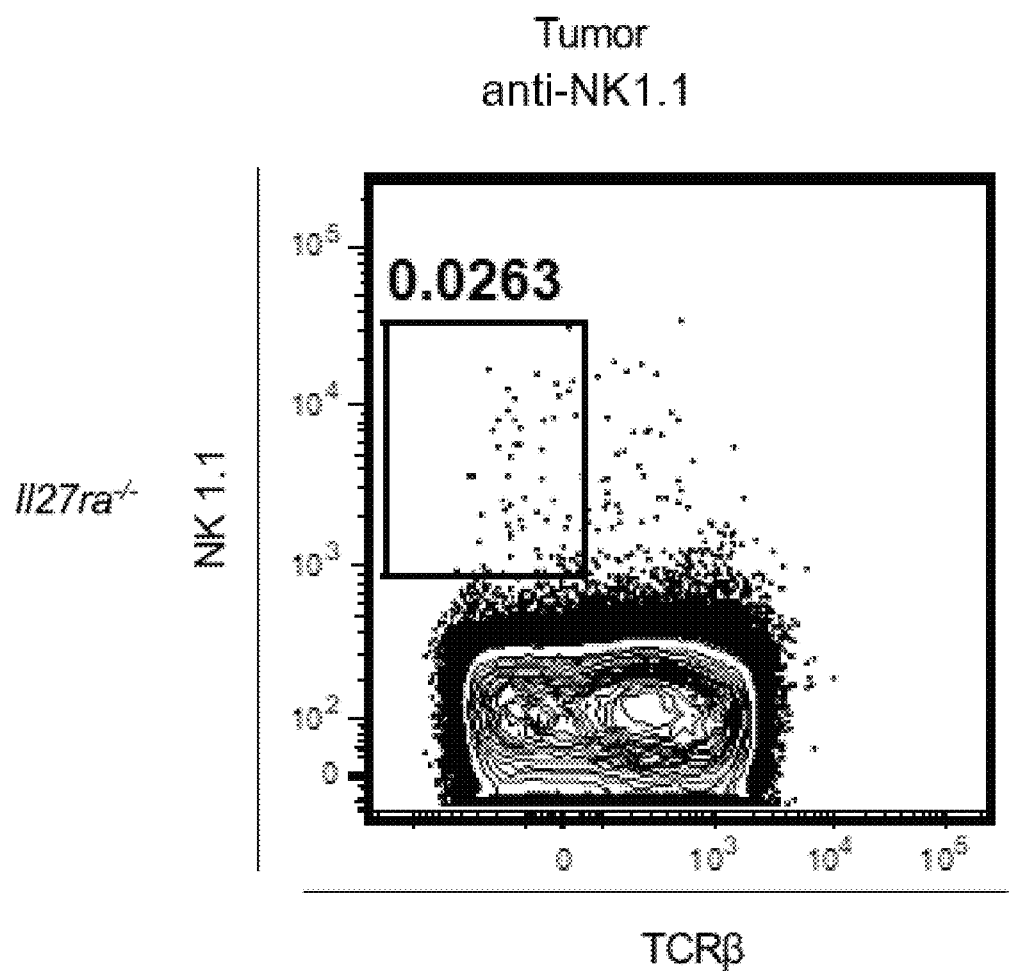

FIGS. 12A and 12B show efficiency of long-term NK-cell depletion. Representative FACS plots of NK cell depletion efficiency in blood (12A) and non-tumor and tumor tissue (12B) from Il27ra$^{+/-}$ and Il27ra$^{-/-}$ male mice which received anti-NK1.1 antibody or isotype control. Data are mean±SEM from at least 3 independent experiments.

DESCRIPTION OF EMBODIMENTS

The terminology used herein is for the purpose of describing particular embodiments only and is not intended to be limiting.

Hepatocellular carcinoma (HCC) is the most common form of liver cancer with poor survival and limited therapeutic options. HCC has different etiologies, typically associated with viral or carcinogenic insults or fatty liver disease and underlying chronic inflammation presents as a major unifying mechanism for tumor promotion. On the other hand, mechanisms of how inflammatory response can regulate anti-cancer immunity in HCC remain incompletely understood.

Interleukin (IL)-27 receptor signaling plays an anti-inflammatory role in a variety of infectious and chronic inflammatory diseases. Here, using genetic and pharmacological approaches we found that IL-27 receptor (IL-27R) signaling promotes HCC development in vivo. Genetic loss of IL-27R suppressed HCC development in both toxin/carcinogen-induced diethylnitrosamine (DEN) and non-alcoholic steatohepatitis (NASH)-driven models. Elevated expression of IL-27RA rendered poor prognosis to HCC patients. Mechanistically, the pro-tumorigenic effect was mediated by immunoregulatory role of IL-27R signaling within the tumor microenvironment, particularly the suppression of Natural killer (NK) cells. IL-27R ablation enhanced the accumulation and activation of cytotoxic NK cells during acute liver injury and in HCC tumors, while depletion of NK cells abrogated the effect of genetic IL-27R disruption.

Here we found that genetic loss of IL-27R surprisingly suppressed liver cancer development in two different in vivo models of HCC, including diethylnitrosamine (DEN) carcinogen-driven and non-alcoholic steatohepatitis (NASH)-driven HCC. Analysis of human HCC revealed that patients with high IL-27R expression display poor survival and have more advanced stages of the HCC. Mechanistically, we found that IL-27R signaling limited the accumulation and activation of natural killer (NK) cells in HCC tumors and IL-27R genetic ablation relieved the inhibition and resulted in infiltration of activated NK cells and reduction in HCC burden. IL-27R signaling repressed expression of NK-activating stress ligands on tumor cells; expression of NK-cell recruiting chemokines and NK cell activating receptors. Inactivation of IL-27R signaling in turn relieved that suppressive effect and enhanced NK cells anti-tumor immune responses in vivo. The dependence of IL-27R signaling driven immunoregulatory effects in HCC on NK cells was further established in experiments, where NK cell depletion reverted the effect of IL-27R inactivation on HCC development. Taken together, our data suggest that inactivation of IL-27R signaling may enhance NK cell accumulation and cytotoxicity and reverse their exhaustion in HCC, providing new therapeutic opportunities as well as preventive approaches in high risk patients with NASH and liver fibrosis set to progress to HCC.

The terminology used herein is for the purpose of describing particular embodiments only and is not intended to be limiting. Various terms relating to aspects of disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in any specific order. Where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, "about" means the numerical value can vary by ±10% and remain within the scope of the disclosed embodiments.

As used herein, the term "antibody" refers to an immunoglobulin molecule that specifically binds to, or is immunologically reactive with, a particular antigen, and includes polyclonal, monoclonal, genetically engineered and otherwise modified forms thereof including, but not limited to, chimeric antibodies, humanized antibodies, heteroconjugate antibodies (e.g., bispecific antibodies, diabodies, triabodies, and tetrabodies).

As used herein, the phrase "antigen-binding fragment thereof" means a fragment of an antibody that is able to bind an antigen. Antigen-binding fragments include, but are not limited to, Fab, Fab', F(ab')$_2$, Fv, scFv, scFv-Fc, diabody, bispecific diabody, trispecific triabody, minibody, monospecific Fab$_2$, bispecific Fab$_2$, trispecific Fab$_3$, nanobody, IgNAR, V-NAR, hcIgG, and VhH fragments.

As used herein, the phrase "chimeric antibody" refers to an antibody having variable sequences derived from a non-human immunoglobulin, such as rat or mouse antibody, and human immunoglobulin constant regions, typically chosen from a human immunoglobulin template.

As used herein, the term "Fv" fragment is the minimum antibody fragment that contains a complete target recognition and binding site. This region consists of a dimer of one heavy and one light chain variable domain in a noncovalent association ($V_H$-$V_L$ dimer). It is in this configuration that the three CDRs of each variable domain interact to define a target binding site on the surface of the $V_H$-$V_L$ dimer.

As used herein, the phrase "human antibodies" refers to antibodies having the amino acid sequence of a human immunoglobulin and includes antibodies isolated from human immunoglobulin libraries or from animals transgenic for one or more human immunoglobulins and that do not express endogenous immunoglobulins.

As used herein, the phrase "humanized antibody" refers to a chimeric antibody, or an antigen-binding fragment thereof, which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the framework (FR) regions that are those of a human immunoglobulin sequence. The humanized antibody can also comprise at least a portion of an immunoglobulin constant region (Fc), typically that of a human immunoglobulin consensus sequence.

As used herein, the phrase "in need thereof" means that the "subject" or "patient" has been identified as having a need for the particular method, prevention, or treatment. In some embodiments, the identification can be by any means of diagnosis. In any of the methods, preventions, and treatments described herein, the "subject" or "patient" can be in need thereof.

As used herein, a "nucleic acid molecule" is a polymeric form of nucleotides of any length, may comprise DNA and/or RNA, and can be single-stranded, double-stranded, or multiple stranded. One strand of a nucleic acid also refers to its complement.

As used herein, the phrase "primatized antibody" refers to an antibody comprising monkey variable regions and human constant regions.

As used herein, the phrase "regulatory sequence" is intended to include promoters, enhancers and other expression control elements, such as polyadenylation signals, that control the transcription or translation of the antibody chain genes.

As used herein, the term "single chain Fv" or "scFv" refers to a single chain Fv antibody in which the variable domains of the heavy chain and the light chain ($V_H$ and $V_L$ domains) from a traditional antibody have been joined to form one chain. Generally, the Fv polypeptide further comprises a polypeptide linker between the $V_H$ and $V_L$ domains which enables the scFv to form the desired structure for target binding.

As used herein, the terms "subject" and "patient" are used interchangeably. A subject includes any animal, including mammals. Mammals include, but are not limited to, farm animals (e.g., horse, cow, pig), companion animals (e.g., dog, cat), laboratory animals (e.g., mouse, rat, rabbits), and non-human primates (e.g., monkey). In some embodiments, the subject or patient is a human.

As used herein, the term "$V_H$" refers to the variable region of an immunoglobulin heavy chain of an antibody, including the heavy chain of, for example, an Fv, scFv, or Fab fragment.

As used herein, the term "$V_L$" refers to the variable region of an immunoglobulin light chain of an antibody, including the light chain of, for example, an Fv, scFv, dsFv, or Fab fragment.

The present disclosure provides methods of treating non-alcoholic steatohepatitis (NASH) in a subject, the method comprising administering to the subject an inhibitor of IL-27 or IL-27R. In some embodiments, the subject is administered an inhibitor of IL-27. In some embodiments, the subject is administered an inhibitor of IL-27R. In some embodiments, the inhibitor of IL-27 or IL-27R is an antibody, or an antigen-binding fragment thereof. In some embodiments, the inhibitor of IL-27 is an antibody, or an antigen-binding fragment thereof. In some embodiments, the inhibitor of IL-27R is an antibody, or an antigen-binding fragment thereof.

In some embodiments, the inhibitor of IL-27 or IL-27R is administered in combination with one or more additional therapeutic agents or procedures. In some embodiments, the one or more additional therapeutic agents or procedures is selected from the group consisting of: a chemotherapy, a targeted anti-cancer therapy, an oncolytic drug, a cytotoxic agent, an immune-based therapy, a cytokine, a surgical procedure, a radiation procedure, an activator of a costimulatory molecule, an inhibitor of an inhibitory molecule, a vaccine, or a cellular immunotherapy, or any combination thereof. In some embodiments, the one or more additional therapeutic agents is a chemotherapy. In some embodiments, the one or more additional therapeutic agents is a targeted anti-cancer therapy. In some embodiments, the one or more additional therapeutic agents is an oncolytic drug. In some embodiments, the one or more additional therapeutic agents is a cytotoxic agent. In some embodiments, the one or more additional therapeutic agents is an immune-based therapy. In some embodiments, the one or more additional therapeutic agents is a cytokine. In some embodiments, the one or more additional therapeutic agents is an activator of a costimulatory molecule. In some embodiments, the one or more additional therapeutic agents is an inhibitor of an inhibitory molecule. In some embodiments, the one or more additional therapeutic agents is a vaccine. In some embodiments, the one or more additional therapeutic agents is a cellular immunotherapy. In some embodiments, the one or more additional procedures is a surgical procedure or a radiation procedure. In some embodiments, the one or more additional procedures is a surgical procedure. In some embodiments, the one or more additional procedures is a radiation procedure.

In some embodiments, the subject has NASH-driven hepatocellular carcinoma (HCC).

In some embodiments, the inhibitor of IL-27 is an antibody, or an antigen-binding fragment thereof. Examples of IL-27 antibodies, or antigen-binding fragments thereof, are disclosed in, for example, PCT Publication WO 2019/183499, which is incorporated herein by reference in its entirety.

The antibodies, or antigen-binding fragments thereof, can be any isotype. In some embodiments, the antibody is an IgM or IgG antibody. In some embodiments, the antibody is an IgM antibody. In some embodiments, the antibody is an IgG antibody. In some embodiments, the antibody is an IgG1 antibody.

In some embodiments, the variant IgG1 heavy chain is paired with a kappa light chain of allotype Km1, Km2, or Km3. In some embodiments, the variant IgG1 heavy chain is paired with a lambda light chain.

In some embodiments, the antibodies, or antigen-binding fragments thereof, are humanized and IgG. In some embodiments, the antibodies, or antigen-binding fragments thereof, are humanized and IgG1.

In some embodiments, the antibody, or antigen-binding fragment thereof, is a chimeric antibody, or antigen-binding fragment thereof. Methods for producing chimeric antibodies are known in the art (see, Morrison, Science, 1985, 229, 1202-1207; Oi et al., BioTechniques, 1986, 4, 214-221; Gillies et al., J. Immunol. Methods, 1985, 125, 191-202; and U.S. Pat. Nos. 5,807,715, 4,816,567, and 4,816,397).

In some embodiments, the chimeric antibody, or antigen-binding fragment thereof, is a primatized chimeric antibody, or antigen-binding fragment thereof. Methods for producing primatized antibodies are known in the art (see, U.S. Pat. Nos. 5,658,570, 5,681,722, and 5,693,780).

In some embodiments, the chimeric antibody, or antigen-binding fragment thereof, is a humanized antibody, or antigen-binding fragment thereof. Methods for producing humanized antibodies are known in the art (see, Riechmann et al., Nature, 1988, 332, 323-327; Padlan, Mol. Immunol., 1991, 28, 489-498; Studnicka et al., Prot. Eng., 1994, 7, 805-814; Roguska et al., Proc. Natl. Acad. Sci., 1994, 91, 969-973; European Patent Nos. EP239400, EP592106, and EP519596; PCT Publication WO 91/09967; and U.S. Pat. Nos. 5,225,539, 5,530,101, 5,585,089, 5,693,761, 5,693,762, 6,180,370, and 5,565,332).

In some embodiments, the antibody, or antigen-binding fragment thereof, is completely humanized. Completely "human" antibodies can be desirable for therapeutic treatment of human patients. Methods for producing completely human antibodies are known in the art, including phage display methods using antibody libraries derived from human immunoglobulin sequences (see, U.S. Pat. Nos. 4,444,887 and 4,716,111; and PCT Publications WO 98/46645, WO 98/50433, WO 98/24893, WO 98/16654, WO 96/34096, WO 96/33735, and WO 91/10741). Human antibodies can also be produced using transgenic mice which are incapable of expressing functional endogenous immunoglobulins, but which can express human immunoglobulin genes (see, PCT Publications WO 98/24893, WO 92/01047, WO 96/34096, and WO 96/33735; and U.S. Pat. Nos. 5,413,923, 5,625,126, 5,633,425, 5,569,825, 5,661,016, 5,545,806, 5,814,318, 5,885,793, 5,916,771, and 5,939,598). Completely human antibodies that recognize a selected epitope can also be generated using a technique referred to as "guided selection" (see, Jespers et al., Biotechnology, 1988, 12, 899-903).

In some embodiments, the antibodies, or antigen-binding fragments thereof, are derivatized antibodies. For example, the derivatized antibodies can be antibodies modified by glycosylation, acetylation, pegylation, phosphorylation, amidation, derivatization by known protecting/blocking groups, proteolytic cleavage, linkage to a cellular ligand or other protein, and the like. Any of numerous chemical modifications can be carried out by known techniques, including, but not limited to, specific chemical cleavage, acetylation, formylation, metabolic synthesis of tunicamycin, and the like. In addition, the derivative can contain one or more non-natural amino acids, such as using ambrx technology (see, Wolfson, Chem. Biol., 2006, 13, 1011-1012).

In some embodiments, the antibodies, or antigen-binding fragments thereof, are derivatized through glycosylation. Suitable biantennary complexes can be composed of a core structure having two N-acetylglucosamine (GlcNAc), three mannose, and two GlcNAc residues that are β-1,2 linked to α-6 mannose and α-3 mannose to form two antennae. One or more fucose (Fuc), galactose (Gal), high mannose glycans Man-5 or Man-9, bisecting GlcNAc, and sialic acid including N-acetylneuraminic acid (NANA) or N-glycolylneuraminic acid (NGNA) residues may be attached to the core. N-linked glycoforms may include G0 (protein having a core biantennary glycosylation structure), G0F (fucosylated G0), G0F GlcNAc, G1 (protein having a core glycosylation structure with one galactose residue), G1F (fucosylated G1), G2 (protein having a core glycosylation structure with two galactose residues), and/or G2F (fucosylated G2).

The antibodies, or antigen-binding fragments thereof, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies can be used to obtain antibody heavy and light chain genes, incorporate these genes into recombinant expression vectors and introduce the vectors into host cells (see, Molecular Cloning; A Laboratory Manual, Second Edition, Sambrook, Fritsch and Maniatis (eds.), Cold Spring Harbor, N.Y., 1989; Current Protocols in Molecular Biology, Ausubel et al., eds., Greene Publishing Associates, 1989; and U.S. Pat. No. 4,816,397).

In some embodiments, to generate nucleic acid molecules encoding the antibodies, or antigen-binding fragments thereof, described herein, DNA fragments encoding the light and heavy chain variable regions are first obtained. These DNAs can be obtained by amplification and modification of germline DNA or cDNA encoding light and heavy chain variable sequences, for example, using the polymerase chain reaction (PCR). Germline DNA sequences for human heavy and light chain variable region genes are known in the art (see, the "VBASE" human germline sequence database; Kabat et al., 1991, Sequences of Proteins of Immunological Interest, Fifth Edition, U.S. Department of Health and Human Services, NIH Publication No. 91-3242; Tomlinson et al., J. Mol. Biol., 1992, 22T, 116-198; and Cox et al., Eur. J. Immunol., 1994, 24, 827-836). A DNA fragment encoding the heavy or light chain variable region can be synthesized and used as a template for mutagenesis to generate a variant as described herein using routine mutagenesis techniques; alternatively, a DNA fragment encoding the variant can be directly synthesized.

In some embodiments, the antibodies, or antigen-binding fragments thereof, are conjugated to an effector moiety. In some embodiments, the antibodies, or antigen-binding fragments thereof, are modified by the covalent attachment of any type of molecule to the antibodies, or antigen-binding fragments thereof, such that covalent attachment does not interfere with binding to the ligand. In some embodiments, the effector moiety is a detectable label, a cytotoxic agent, a chemotherapeutic agent, or a nucleic acid molecule. The effector moiety can also be an antineoplastic agent, a drugs, a toxin, a biologically active protein (such as an enzyme), another antibody or antibody fragment, a synthetic or naturally occurring polymer, a nucleic acid molecule, a radionuclides (such as radioiodide), a radioisotope, a chelated metal, a nanoparticle, or a reporter group (such as a fluorescent compound or a compound which can be detected by NMR or ESR spectroscopy).

In some embodiments, the antibodies, or antigen-binding fragments thereof, can be conjugated to a cytotoxic agent, a radionuclide, or a drug moiety to modify a particular biological response. The effector moiety can be a protein or polypeptide, such as, for example, a toxin (such as abrin, ricin A, saporin, *Pseudomonas* exotoxin, diphtheria toxin, ethidium bromide or PE40, PE38, gelonin, RNAse, peptide nucleic acids (PNAs), ribosome inactivating protein (RIP) type-1 or type-2, pokeweed anti-viral protein (PAP), bryodin, momordin, chemotherapeutic agents, and bouganin), a signaling molecule (such as α-interferon, β-interferon, nerve growth factor, platelet derived growth factor or tissue plasminogen activator), a thrombotic agent or an anti-angiogenic agent (such as, angiostatin or endostatin) or a biological response modifier such as a cytokine or growth factor (such as, interleukin-1 (IL-1), interleukin-2 (IL-2), interleukin-6 (IL-6), granulocyte macrophage colony stimulating factor (GM-CSF), granulocyte colony stimulating factor (G-CSF), or nerve growth factor (NGF)).

In some embodiments, the cytotoxic agent is a small molecule, a prodrug, a maytansinoid, or a toxin. In some embodiments, the antibody, or antigen-binding fragment thereof, comprises from 3 to 5 maytansinoid molecules per antibody, or antigen-binding fragment thereof. In some embodiments, the maytansinoid is conjugated to the antibody, or antigen-binding fragment thereof, by a chemical linker chosen from N-succinimidyl-3-(2-pyridyldithio) propionate, N-succinimidyl-4-(2-pyridylthio)pentanoate (SPP), and succinimidyl-4-(N-maleimidomethyl)cyclohexanel-1-carboxylate. In some embodiments, the cytotoxic agent is taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, or puromycin.

In some embodiments, the detectable label is radioactive compound, a fluorescent compound, a chromophore, an enzyme, an imaging agent, a metal ion, or a substrate. In some embodiments, a fluorescent moiety includes, but is not limited to, fluorescein, fluorescein isothiocyanate, rhodamine, 5-dimethylamine-1-napthalenesulfonyl chloride, phycoerythrin and the like. Useful enzymatic labels include, but are not limited to, alkaline phosphatase, horseradish peroxidase, glucose oxidase, and the like.

In some embodiments, the effector moiety is an antimetabolite (such as, methotrexate, 6-mercaptopurine, 6-thioguanine, cytarabine, and 5-fluorouracil decarbazine), an alkylating agent (such as, mechlorethamine, thioepa chlorambucil, melphalan, carmustine (BSNU) and lomustine (CCNU), cyclothosphamide, busulfan, dibromomannitol, streptozotocin, mitomycin C5 and cisdichlorodiamine platinum (II) (DDP) cisplatin), an anthracycline (such as, daunorubicin (formerly daunomycin) and doxorubicin), an antibiotic (such as, dactinomycin (formerly actinomycin), bleomycin, mithramycin, anthramycin (AMC), calicheamicins or duocarmycins), or an anti-mitotic agent (such as, vincristine and vinblastine).

In some embodiments, the radionuclides is, but is not limited to, $^{13}$N, $^{18}$F, $^{32}$F, $^{64}$Cu, $^{66}$Ga, $^{67}$Ga, $^{68}$Ga, $^{77}$Br, $^{80m}$Br, $^{82}$Rb, $^{86}$Y, $^{90}$Y, $^{95}$RU, $^{97}$RU, $^{99m}$TC, $^{103}$Ru, $^{105}$Ru, $^{111}$In, $^{113m}$In, $^{113}$Sn, $^{121m}$Te, $^{122m}$Te, $^{125m}$Te, $^{123}$I, $^{124}$I, $^{125}$I, $^{126}$I, $^{131}$I, $^{133}$I, $^{165}$Tm, $^{167}$Tm, $^{168}$Tm, $^{177}$Lu, $^{186}$Re, $^{188}$Re, $^{195m}$Hg, $^{211}$At, $^{212}$Bi, $^{213}$Bi, and $^{225}$Ac.

In some embodiments, the chemotherapeutic agent is cisplatin, carboplatin, oxaliplatin, nedaplatin, triplatin tetranitrate, phenanthr platin, picoplatin, satraplatin, methotrexate, vincristine, doxorubicin, tunicamycin, oligomycin, bortezomib, MG132, 5-flurouracil, sorafenib, flavopiridol, gemcitabine, taxol, mercaptopurine, thioguanine, hydroxyurea, cytarabine, mitomycin, cyclophosphamide, ifosfamide, nitrosourea, dacarbazine, procarbizine, an etoposide, a campathecin, bleomycin, idarubicin, daunorubicin, dactinomycin, distamycin A, etidium, netropsin, auristatin, amsacrine, prodigiosin, bortexomib, pibenzimol, tomaymycin, duocarmycin SA, plicamycin, mitoxantrone, asparaginase, vinblastine, vinorelbine, paclitaxel, docetaxel, CPT-11, gleevec, erlotinib, gefitinib, ibrutinib, crizotinib, ceritinib, lapatinib, navitoclax, or regorafenib.

In some embodiments, the antibodies, or antigen-binding fragments thereof, can be conjugated to a small molecule toxin. In some embodiments, the antibodies, or antigen-binding fragments thereof, can be conjugated to a dolostatin or a dolostatin peptidic analog or derivative, such as an auristatin (see, U.S. Pat. Nos. 5,635,483 and 5,780,588). The dolostatin or auristatin drug moiety may be attached to the antibody through its N-terminus, C-terminus or internally (see, PCT Publication WO 02/088172). Exemplary auristatin embodiments include the N-terminus linked monomethylauristatin drug moieties DE and DF, as disclosed in U.S. Pat. No. 7,498,298 (disclosing linkers and methods of preparing monomethylvaline compounds such as MMAE and MMAF conjugated to linkers).

Antibodies, or antigen-binding fragments thereof, can also be conjugated to liposomes for targeted delivery (see, Park et al., Adv. Pharmacol., 1997, 40, 399-435; and Marty et al., Methods Molec. Med., 2004, 109, 389-401).

In some embodiments, the antibodies, or antigen-binding fragments thereof, can be attached to poly(ethyleneglycol) (PEG) moieties. In some embodiments, the antibodies, or antigen-binding fragments thereof, and the PEG moieties can be attached through any available amino acid side-chain or terminal amino acid functional group located in the antibodies, or antigen-binding fragments thereof, for example, any free amino, imino, thiol, hydroxyl or carboxyl group. Such amino acids can occur naturally in the antibodies, or antigen-binding fragments thereof, or can be engineered into the fragment using recombinant DNA methods (see, U.S. Pat. No. 5,219,996). Multiple sites can be used to attach two or more PEG moieties. PEG moieties can be covalently linked through a thiol group of at least one cysteine residue located in the antibodies, or antigen-binding fragments thereof. Where a thiol group is used as the point of attachment, appropriately activated effector moieties, for example, thiol selective derivatives such as maleimides and cysteine derivatives, can be used.

In some embodiments, the antibodies, or antigen-binding fragments thereof, can comprise a modified Fab' fragment which is PEGylated. The PEG moiety can be attached to a cysteine in the hinge region. In some embodiments, a PEG-modified Fab' fragment has a maleimide group covalently linked to a single thiol group in a modified hinge region. A lysine residue can be covalently linked to the maleimide group and to each of the amine groups on the lysine residue can be attached a methoxypoly(ethyleneglycol) polymer having a molecular weight of approximately 20,000 Da. The total molecular weight of the PEG attached to the Fab' fragment can therefore be approximately 40,000 Da.

In some embodiments, the antigen-binding fragment can be an Fab, an F(ab')2, an Fv, an scFv, an scFv-Fc, a diabody, or a minibody fragment. In some embodiments, the antigen-binding fragment can be an Fab fragment. In some embodiments, the antigen-binding fragment can be an F(ab')2 fragment. In some embodiments, the antigen-binding fragment can be an Fv fragment. In some embodiments, the antigen-binding fragment can be an scFv fragment. In some embodiments, the antigen-binding fragment can be an scFv-Fc fragment. In some embodiments, the antigen-binding fragment can be a diabody fragment. In some embodiments, the antigen-binding fragment can be a minibody fragment.

In some embodiments, the antibodies, or antigen-binding fragments thereof, described herein can be administered to a patient by a variety of routes such as orally, transdermally, subcutaneously, intranasally, intravenously, intraarterially, intramuscularly, intraocularly, topically, locally, intrathecally, intracerebroventricularly, intraspinally, and intracranially. The most suitable route for administration in any given case will depend on the particular antibody, the subject, and the nature and severity of the disease and the physical condition of the subject. In some embodiments, the antibodies, or antigen-binding fragments thereof, can be formulated as an aqueous solution. In some embodiments, the antibodies, or antigen-binding fragments thereof, are administered intravenously or intracranially.

In some embodiments, the administration of the antibodies, or antigen-binding fragments thereof, described herein is repeated after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens, a patient can receive antibody therapy for a prolonged period of time, such as 6 months, 1 year, or more. The amount of the antibodies, or antigen-binding fragments thereof, described herein administered to the patient is a therapeutically effective amount. As used herein, a "therapeutically effective" amount of the antibodies, or antigen-binding fragments thereof, described herein can be administered as a single dose or over the course of a therapeutic regimen, such as over the course of a week, two weeks, three weeks, one month, three months, six months, one year, or longer. Exemplary therapeutic regimens are further described herein. Treatment of a disease encompasses the treatment of patients already diagnosed as having any form of NASH at any clinical stage or manifestation; the delay of the onset or evolution or aggravation or deterioration of the symptoms or signs of the disease; and/or preventing and/or reducing the severity of the disease.

In some embodiments, the antibodies, or antigen-binding fragments thereof, described herein are administered as an IV infusion once every 7 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg. In some embodiments, the antibodies, or antigen-binding fragments thereof, described herein are administered as an IV infusion once every 14 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg. In some embodiments, the antibodies, or antigen-binding fragments thereof, described herein are administered as an IV infusion once every 21 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg. In some embodiments, the antibodies, or antigen-binding fragments thereof, described herein are administered as an IV infusion once every 28 days at about 0.1 mg/kg, about 0.5 mg/kg, about 1.0 mg/kg, about 2.0 mg/kg, about 3.0 mg/kg, about 4.0 mg/kg, about 5.0 mg/kg, about 6.0 mg/kg, about 8.0 mg/kg, or about 10.0 mg/kg.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: General Methods

Mice:

Il27ra$^{-/-}$≥(JAX #018078) and C57BL6/J (WT) (JAX #000664) mice were purchased from Jackson laboratory and crossed to obtain Il27ra$^{+/-}$ and Il27ra$^{-/-}$ mice. Ncr1$^{gfp/gfp}$ were obtained from Dr. Wayne Yokoyama (Washington University, St. Louis) and used to generate Il27ra$^{+/-}$Ncr1$^{+/gfp}$, and Il27ra$^{-/-}$Ncr1$^{+/gfp}$. For NASH model, Il27ra$^{-/-}$ mice were crossed to MUP-uPA$^+$ (Weglarz et al., Amer, J. Pathol., 2000, 157, 1963-1974) to obtain MUP-uPA$^+$Il27ra$^{+/-}$ and MUP-uPA$^+$Il27ra$^{-/-}$ mice. All mice were on C57BL/6 background. The genotyping was performed by standard PCR protocols. Mice were housed and bred under specific pathogen-free condition in an AAALAC-approved barrier facility. Littermate and cagemate controls were used for all experiments.

DEN model: To induce HCC development, 25 mg/kg of diethylnitrosamine (DEN) (Sigma-Aldrich, N0258) was administered intraperitoneally into male mice at the age of 15 days as previously described (Sakurai et al., Cancer Cell, 2008, 14, 156-165'. Mice were maintained on autoclaved water and a regular chow diet. HCC development was analyzed at 10 months of age. For acute response mice were collected 48 h after DEN (100 mg/kg) administration.

NASH model: MUP-uPA$^+$Il27ra$^{+/-}$ and MUP-uPA$^+$Il27ra$^{-/-}$ female and male mice were fed Western diet (Teklad, TD.88137) for 8 months beginning at 8 weeks after birth. HCC development was analyzed at 10 months of age.

Antibody Treatment:

200 µg/mouse of anti-NK1.1 (PK136, FCCC cell culture facility) or SV40 IgG2a (PAB419, FCCC cell culture facility) isotype control antibodies were injected i.p. weekly for 5.5 months starting from 4.5 months of age.

500 µg/mouse of anti-IL-27 (SRF381, Surface Oncology) or IgG2a isotype control antibodies were injected i.p. for the last 15 weeks prior to tissue collection at 10 months. The human monoclonal antibody SRF381 was selected for binding to recombinant human IL-27 and cross-reactivity to recombinant murine IL-27. SRF381 inhibits IL-27 mediated phosphorylation of STAT1 in human PBMCs and murine splenocytes. The Fc region of SRF381 was replace with murine IgG2a.

Histology and Immunohistochemistry:

For histological analysis; a liver lobe (with tumors) was isolated and fixed in 10% buffered formalin (Fisher Health-Care, 23-245685) for 24 hours, Five µm thick sections were prepared and stained with hematoxylin (Sigma-Aldrich, HHS32) and eosin Y (Thermo Scientific, 6766007). All images were acquired with Nikon Eclipse 80i microscope. For immunohistochemistry staining, 5 µm thick sections of livers containing tumors were deparaffinized by taking them through 4 changes in xylenes, then washed by 4 changes in 100% ethanol followed by re-hydration in tap water. Antigen retrieval was performed in 1× Citrate buffer (Electron Microscopy Sciences, 64142-08) at 95° C. for 1 hour followed by 1 hour cooling down to room temperature. Slides were rinsed in tap water for 3 minutes and dehydrated in 100% ethanol for 1 minute, followed by blocking in 3% $H_2O_2$ in PBS for 10 minutes. Slides were blocked with 5% goat serum in 1% BSA-PBS for 20 minutes, and were incubated with primal), antibody for anti-Ki67 (1:100; BioLegend, 151202), anti-pERK1/2 (1:400; Cell Signaling; 4370) or anti-IL-27Ra (34N4G11; Novus Biologicals, NBP2-19015) overnight at 4° C. After washing with 1% BSA-PBS, slides were incubated with secondary goat anti-rat and goat anti-rabbit biotinylated antibodies for 30 minutes at room temperature followed by 30 minutes of incubation with streptavidin-HRP (1:500; BD Pharmingen, 554066). For developing; DAB substrate (Invitrogen) was applied for 3 minutes followed by washing in water and counterstaining with Hematoxylin solution (Sigma-Aldrich, HHS32). Excess of Hematoxylin was removed by immersing slides in 0.25% ammonia water followed by rinsing in water. Slides were mounted with coverslips using Permount mounting medium solution (Fisher Chemical, SP15). All images were acquired with Nikon Eclipse 80i microscope, Microsoft PowerPoint was used for one step brightness adjustment for all images in parallel. Quantification was done using ImageJ (version 1.51).

Van Gieson Staining:

For collagen staining, deparaffinized and re-hydrated slides were stained for 5 minutes in Van Gieson solution (EMS, 26374-06) followed by dehydration by 2 changes in 100% ethanol and cleared by 2 changes of xylenes. All images were acquired with Nikon Eclipse 80i microscope. Microsoft PowerPoint was used for one step brightness adjustment for all images in parallel. Quantification was done using ImageJ (version 1.51).

Flow Cytometry:

Mice were sacrificed by $CO_2$ inhalation and livers were perfused with HESS containing 2% of Heparin (20 USP units/mL) to remove traces of blood, Livers were isolated, non-tumor and tumor tissues were dissected separately and incubated with a cocktail of digestion enzymes containing collagenase I (450 Unit) (Sigma-Aldrich, 00130) and DNase I (120 U/mL) (Sigma-Aldrich, D4263) in HBSS (with $Ca^{2+}/Mg^{2+}$) for 40 minutes at 37° C. with gentle shaking at 150 rpm. After incubation, cell suspension was filtered through a 70 µm cell strainer. Immune cells were enriched by density-gradient centrifugation over Percoll (GE Healthcare, 17-0891-01) at 1000×g for 25 minutes without brake (40% Percoll in RPMI-1640 and 80% Percoll in PBS). Leukocyte ring on a border of gradient and parenchymal cells on top were collected, washed and stained. The following antibodies were used: CD45-PercP (30F-11; BioLegend; 103130), CD11b-Pacific Blue (M1/70; BioLegend, 101224). NK1.1-FITC (PK136; BioLegend, 108706), NK1.1-PE (PK136; BioLegend, 108708), TCRβ-Alexa Fluor 700 (H57-597; BioLegend, 109224), CD4-APC/Cy7 (GK1.5; BioLegend, 100414), CD8α-APC (53-6.7; BioLegend, 100712), Ly6G-APC/Cy7 (1A8; BioLegend, 127624), Ly6C-PE/Cy7 (HK1.4; BioLegend, 128018); F4/80-APC (BMS; BioLegend, 123116), Granzyme B-Pacific Blue (GB 11; BioLegend, 515408), CD27-PE/Cy7 (LG.3A10; BioLegend, 124216), Ly-49C-APC (4L03311), Ly-49I-PE (YLI-90; eBioscience, 1943023), NKG2AB6-APC (16A11; BioLegend, 142808), NKG2D-PE (CX5; BioLegend, 130208), CD49a-PE/Cy7 BioLegend, 142608), CD49b-APC/Cy7 (DX5; BioLegend, 108920), CD11b-biotin (M1/70; BioLegend, 101204), CD31-PE (390; BioLegend, 102408), TER-119-biotin (TER-119; BioLegend, 1162204), H-2Kb-PE/Cy7 (AF6-88.5; BioLegend, 116519), H-2K$^b$/H-2D$^b$-APC/Fire 750 (28-8-6; BioLegend, 114617), Streptavidin-APC/Cy7 (BioLegend, 405208)

Spleens were isolated, mashed and filtered through 70 μm cell strainers. Peripheral blood was collected by cardiac puncture and erythrocytes were lysed by red blood cell (RBC) lysis buffer (15 nM NH$_4$Cl, 0.1 mM NaHCO$_3$, 0.1 mM Na$_2$-EDTA) for 5 minutes at room temperature. Peripheral blood and splenocytes were stained with CD45-PercP (30F-11; BioLegend, 103130), NK1.1-FITC (PK136; BioLegend, 108706), NK1.1-PE (PK136; BioLegend, 108708), TCRβ-Alexa Fluor 700 (H57-597; BioLegend, 109224), Ly-49C-APC; Ly-49I-PE (YLI-90; eBioscience, 1943023), NKG2AB6-APC (16A11; BioLegend, 142808), NKG2D-PE (CX5; BioLegend, 130208), CD49a-PE/Cy7 (HMα1; BioLegend, 142608) and CD49b-APC/Cy7 (DX5; BioLegend, 108920). All antibodies were used at 1:50 dilution and LIVE/DEAD Fixable Yellow Dead Cell stain (Invitrogen, L34959) at 1:200.

Gene Expression Analysis:

Non-tumor and tumor tissues were homogenized in TRIzol reagent (Invitrogen, 15596018) with 2.8 mm ceramic beads (OMNI International, 19-646-3) using Bead Ruptor (OMNI International). Total RNA was extracted using Aurum Total RNA Fatty and Fibrous Tissue Kit (Bio-Rad, 7326870) according to manufacturer's protocol. Sorted or treated cells were lysed in RLT Plus buffer (QIAGEN, 157030074) and total RNA was isolated using RNeasy Plus Mini Kit (QIAGEN, 74136) according to manufacturer's protocol. Complementary DNA was synthesized using iScript Reverse Transcription Supermix (Bio-Rad, 1708841) with random primers according to manufacturer's protocol. Q-RT-PCR was performed with Bio-Rad CFX 96 Connect Real-Time PCR Detection System using iTaq Universal SYBR Green Supermix (Bio-Rad, 1725124), The following primers were used: Rpl32, Lcn2, Ccnd1, Cxcr6, Gzmb, Prf1, Tnfsf10, Faslg, Ifng, Klrk1, Raet1a, H60b, Tap1, Cxcl9, Crcl10.

Clonogenic Assay:

1000 DEN-derived HCC cells were plated on 0.1%-swine gelatin precoated 6-well plate in ACL-4 containing 20% FBS in triplicate per condition. Twenty-four hours later, medium was changed to ACL-4 containing 5% FBS with or without rIL-27 (200 ng/ml), On day 4, medium was refreshed and cells were left to grow for additional 3 days. On day 7, after beginning of the treatment, the medium was aspirated, cells were washed with HBSS (Ca$^{2+}$/Mg$^{2+}$ free) and fixed 10% acetic and 10% methanol fixing solution for 15 minutes at room temperature. When fixing solution was aspirated, plates were left to dry followed by adding 0.4% crystal violet staining solution for 20 minutes at room temperature, Rinsed with tap water wells were scanned with EPSON Perfection V600 Photo scanner.

Immunomagnetic Purification of NK Cells and Treatment with rIL-27 In Vitro:

NK cells were purified from spleen of wild type male mice by negative selection using magnetic beads and a cocktail of biotinylated antibodies: CD3e (145-2C11; BioLegend, 100304), CD4 (GK1.5; BioLegend, 100404), CD8α (53-6.7; BioLegend, 100704), CD11b (M1/70; BioLegend, 101204), CD11c (N418; BioLegend, 117304). Gr-1 (RB6-8C5; BioLegend, 108404), TER-119 (TER-119; BioLegend, 1162204), B220 (RA3-6B2; BioLegend, 103204) and CD19 (6D5; BioLegend, 115504). Purified NK cells were plated at a density of 250,000 cells/mL in 2 mL of complete RPMI-1640 without PBS containing 25 ng/ml, of rIL-27. Twelve hours later, cells were lysed and used for gene expression analysis.

HCC Stimulation In Vitro:

For gene expression analysis, 500,000 DEN-derived 1-ICC cells were plated on a 0.1%-swine gelatin precoated 6-well plate in ACL-4 containing 20% FBS in triplicate per condition. Twenty-four hours later, medium was changed to complete DIEM without FBS with or without rIL-27 (200 ng/ml) for 3 hours at 37° C. in a 5% CO$_2$ cell culture incubator. For Western blot analysis cell were treated as described above and collected at 0, 15, and 30 minutes, Partial Hepatectomy:

⅔ partial hepatectomy was performed as previously described (Mitchell et al., Nat. Protoc., 2008, 3, 1167-1170). Briefly, mice were anesthetized by isoflurane. Skin and abdominal wall were cut open; left and right lobe were ligated sequentially with silk suture and excised. Then abdominal wall was sutured and skin was clipped. Liver regeneration was analyzed in 8 days, Western Blot:

In vitro treated HCC were washed with HBSS (Ca$^{2+}$/Mg$^{2+}$ free) and lysed in RIPA buffer supplemented with phosphatase and protease inhibitors (Sigma-Aldrich, PPC1010) (200 μL per 10$^6$ cells) followed by centrifugation at 15,000×g for 10 minutes at 4° C. to pellet not lysed cell debris. The supernatant was collected for the analysis. Protein concentration was determined by BCA Protein Assay Kit (Sigma-Aldrich, 1001491004) according to manufacturer's protocol. 40 μg of cell lysates was separated by 4-20% Tris-glycine MINI-PROTEAN TGX gels (Bio-Rad, 4564094) and transferred to PVD membranes using Trans-Blot Turbo Transfer Pack (Bio-Rad, 1704156). Each membrane was washed with TBST (10 mM Tris-HCl, 150 mM NaCl, 0.1% Tween-20; pH 7.6) and blocked with 5% skimmed milk in TBST for 1 hour followed by overnight incubation at 4° C. with appropriate primary antibody: pSTAT3 (D3A7; Cell Signaling Technology, 9145S) and STAT3 (124H6; Cell Signaling Technology, 9139S). Loading was evaluated by staining with β-actin-horseradish peroxidase (HRP) (AC-15; Abcam, ab49900) antibody (1:50000) for 1 hour at room temperature. Each membrane was washed and primary antibodies (except 0-actin-HRP) were detected with a 1:5000 dilution of HRP-conjugated rabbit anti-mouse IgG (Cell Signaling Technology, 7076S) or mouse anti-rabbit IgG (Cell Signaling Technology, 7074S). The reactive bands were developed using ECL Prime western blotting detection reagent (GE Healthcare, RPN2232) and were visualized with an autoradiography film (LabScientific, XAR ALF 2025).

NK Cytotoxicity In Vivo:

NK-cell cytotoxicity was measured as previously described (Saudemont et al., Methods Mol. Biol., 2010, 612;

325-334). Briefly, RMA and RMA-S T-cell lymphoma cells were labelled with Orange CMRA (Invitrogen, C34551) or CPD eFluor 650 (eBioscience, 65-0840-90) dyes, respectively. $2\times10^5$ cells of each cell line were mixed in 1:1 ratio and injected i.p. to Il27ra$^{+/-}$ or Il27ra$^{-/-}$ mice. Forty-eight hours later, mice were sacrificed, peritoneal lavage was collected and analyzed by FACS.

NanoString:

50 ng of tumor RNA was used for NanoString to analyze an immune profile of the tumor microenvironment measuring the expression of 770 genes according to manufacturer's protocol. The hybridization between target mRNA and reporter-capture probe pairs was performed at 65° C. for 20 hours using Applied Biosystems Veriti Thermal Cycler. All processing was carried out on a fully automated nCounter Prep Station. Excess of probes was removed and probe-target complexes were aligned and immobilized in the nCounter cartridge followed by the image acquisition and data processing by nCounter Digital Analyzer. The expression level of a gene was measured by counting the number of times the specific barcode for that gene was detected, and the barcode counts were then tabulated in a comma-separated value (CSV) format. The raw digital count of expression was exported from nSolver v3.0 software. Statically significant differentially expressed genes between genotypes were analyzed by KEGG pathway analysis.

Statistical Analysis:

Student's two-tailed t-test was used for comparison between two groups. Survival curve data were analyzed using the long-rank (Mantel-Cox) test. Chi-square test was used to compare stages of human HCC. Tukey's test was used for multiple comparisons. Data were analyzed using the GraphPad Prism Software (Version 7.0). Data are presented as mean±SEM; *p<0.05, p<0.01, *p<0.001, ****p<0.0001. A p-value<0.05 was considered statistically significant.

Example 2: IL-27R Signaling Promotes HCC Development in DEN-Induced Model

Figure 1B:
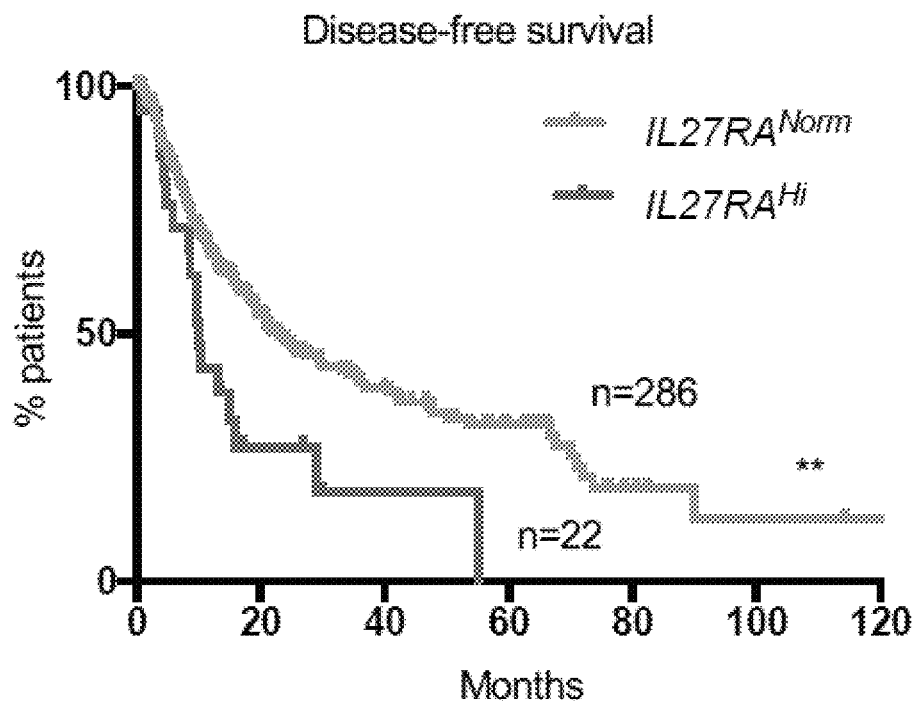
Figure 1C:
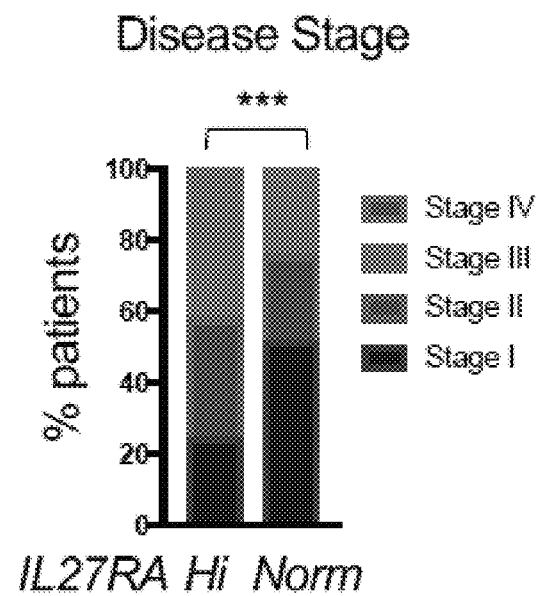

While the role of IL-27R signaling has been investigated in infectious and inflammatory diseases (Villarino et al., Immunity, 2003, 19, 645-655; Findlay et al., J. Immunol., 2010, 185, 2482-2492; Fitzgerald et al., J. Immunol., 2007, 179, 3268-3275; Peshkova et al., Sci. Rep., 2017, 7, 2255; and Peshkova et al., Nat. Commun., 2019, 10, 5046), little is known about its possible contribution to tumor development and progression in vivo. We first analyzed the expression of this cytokine receptor in human HCC tumors. IHC staining of human liver tissue with developed HCC revealed that IL-27R is expressed by infiltrating immune cells as well as hepatocytes (see, FIG. 1A). Next, we evaluated the impact of IL27RA expression in human HCC tumors on disease-free survival using TCGA provisional data subjected to Kaplan-Meier analysis. We found that patients with high IL27RA expression exhibited poor disease-free survival and presented with more advanced stages of HCC, suggesting a potential cancer-promoting role of IL-27R signaling in HCC (see, FIGS. 1B and 1C). Such a role is nevertheless surprising as IL-27R signaling was previously shown to reduce the expression of IL-6, IL-17A and other inflammatory cytokines deemed pro-tumorigenic in HCC (Ringelhan et al., Nat. Immunol., 2018, 19, 222-23; and Koltsova et al., Circulation Res., 2012, 111, 1274-1285).

Figure 1D:
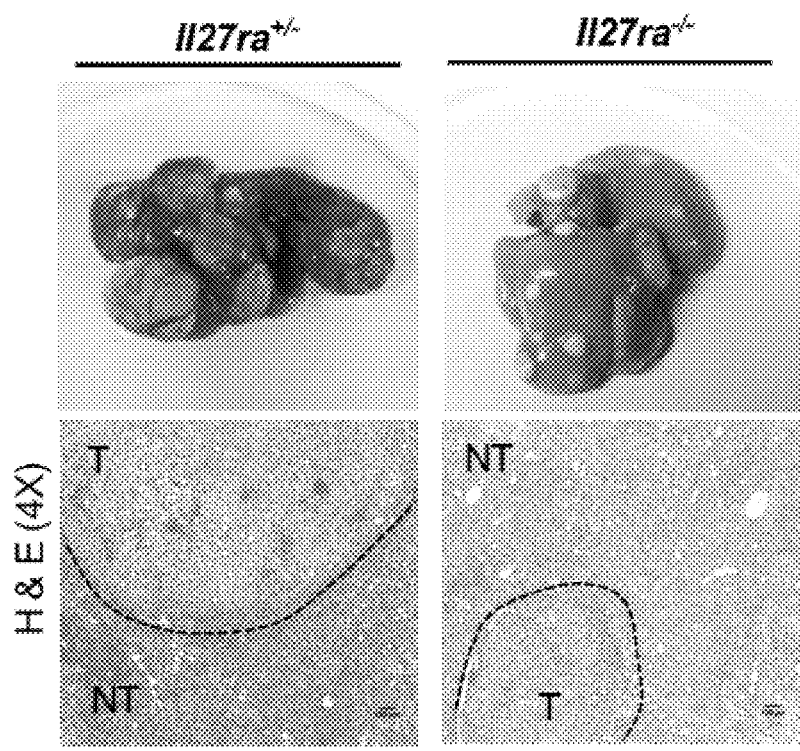
Figure 1H:
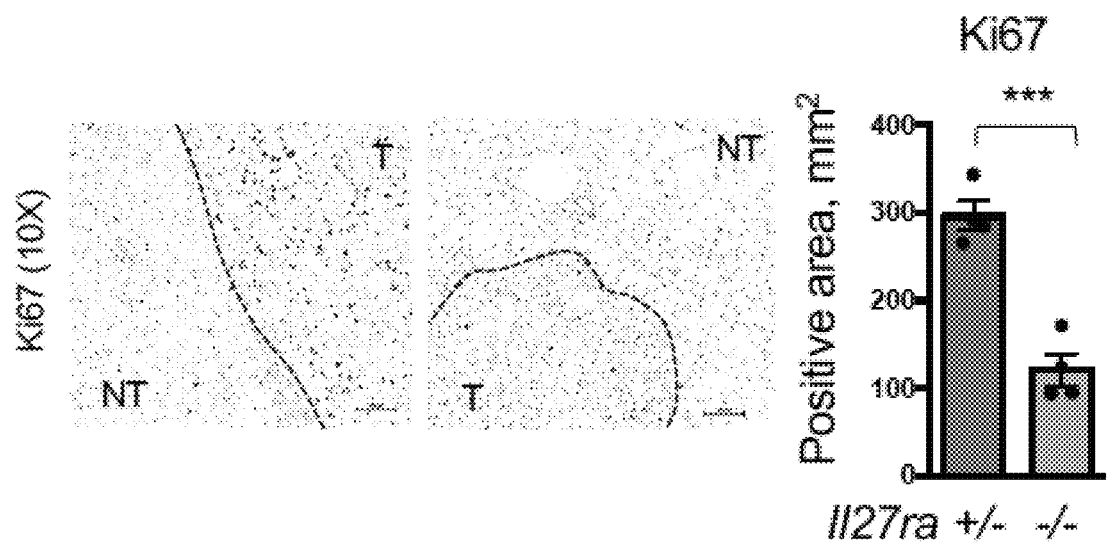
Figure 1I:
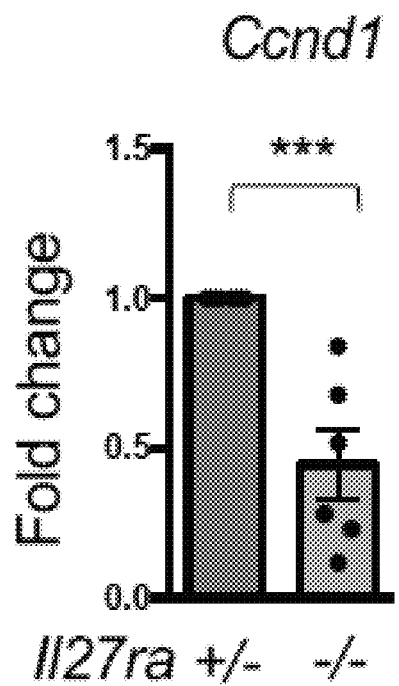
Figure 1J:
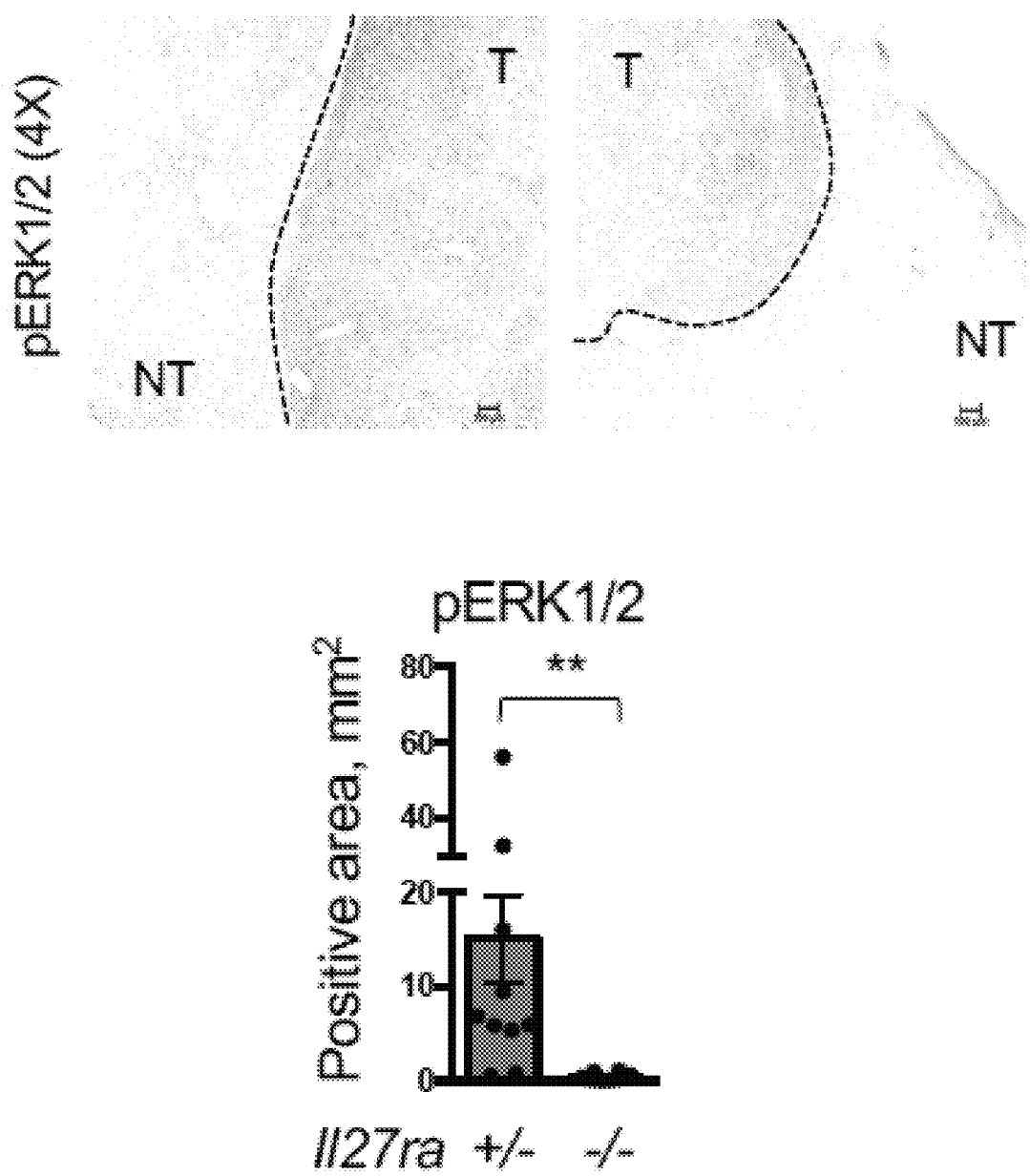

To directly evaluate the potential role of IL-27R signaling in HCC, we used a genetic approach in a well-established mouse model of HCC driven by the toxin/carcinogen DEN (Park et al., Cell, 2010, 140, 197-208; Naugler et al., Science, 2007, 317, 121-124; and Sakurai et al., Cancer Cell, 2008, 14, 156-165). To exclude any confounding influence of genetics or microbiota, we used cage-mate and littermate controls. Male Il27ra$^{+/-}$ or Il27ra$^{-/-}$ mice were injected with 25 mg/kg of DEN i.p. at day 15 after birth and tumor development was assessed at 10 months of age. Given previous observations that IL-27 dampens inflammatory signaling (Yoshida et al., Annu. Rev. Immunol., 2015, 33, 417-443), we expected that IL-27R ablation would exacerbate inflammation and promote in vivo HCC development. Unexpectedly, we found that HCC tumorigenesis was markedly reduced in Il27ra$^{-/-}$ mice compared to Il27ra$^{+/-}$ controls (see, FIGS. 1D and 1E). Body weight of tumor-bearing mice was not affected by IL-27R deficiency (see, FIG. 8A). Serum level of ALT, a marker of liver damage reflecting HCC formation, was significantly lower in Il27ra$^{-/-}$ mice compared to their Il27ra$^{+/-}$ tumor bearing counterparts suggesting preserved liver function in the absence of IL-27R (see, FIG. 1F). No difference was detected in serum Albumin, Globulin or total bilirubin (see, FIG. 8B). In line with limited liver damage, HCC tumors from IL-27R deficient mice were also characterized by lower expression of the inflammatory marker Lcn2 (see, FIG. 1G). Tumors of IL-27R deficient mice were characterized by reduced proliferation as determined by Ki67 staining (see, FIG. 1H) and cyclin D1 (Ccnd1) expression (see, FIG. 1I). Consistently with lower proliferation and inflammation/injury, activation of kinase ERK1/2 was also reduced in IL-27R deficient tumors (see, FIG. 1J). To determine if limited proliferation is a broader representation of IL-27R-dependent liver regeneration capacity, we compared liver regeneration in IL-27R deficient and sufficient mice. Partial hepatectomy of ⅔ of liver tissue revealed no significant differences between Il27ra$^{-/-}$ or control Il27ra$^{+/-}$ mice in the ability to regenerate liver mass, suggesting that IL-27R regulates HCC development independent of its effects on liver regeneration (see, FIG. 9A). In vitro stimulation of DEN-derived primary HCC cells with recombinant IL-27 (rIL-27) was also unable to change HCC cell growth in an in vitro clonogenic assay (see, FIG. 9B), despite induction of STAT3 phosphorylation in HCC cells (see, FIG. 9C).

Collectively, our data demonstrate that IL-27R signaling promotes HCC in the carcinogen-induced model in vivo.

Example 3: IL-27R Signaling Restricts NK Cell Accumulation in HCC

HCC progression is regulated by various immune cells, accumulating in tumor and non-tumor tissue (Ringelhan et al., Nat. Immunol., 2018, 19, 222-232). To elucidate the potential mechanisms by which IL-27R signaling controls tumor growth, we first conducted NanoString gene expression analysis on isolated tumors from IL-27R deficient and proficient animals. Among the most notable changes we found an increase in NK-specific markers and overall upregulation of the NK-mediated cytotoxicity pathway as defined by KEGG analysis in tumors of Il27ra$^{-/-}$ mice, implying a potential role of IL-27R-dependent NK cell regulation in the control of HCC (see, FIGS. 2A and 2B).

Figure 2A:
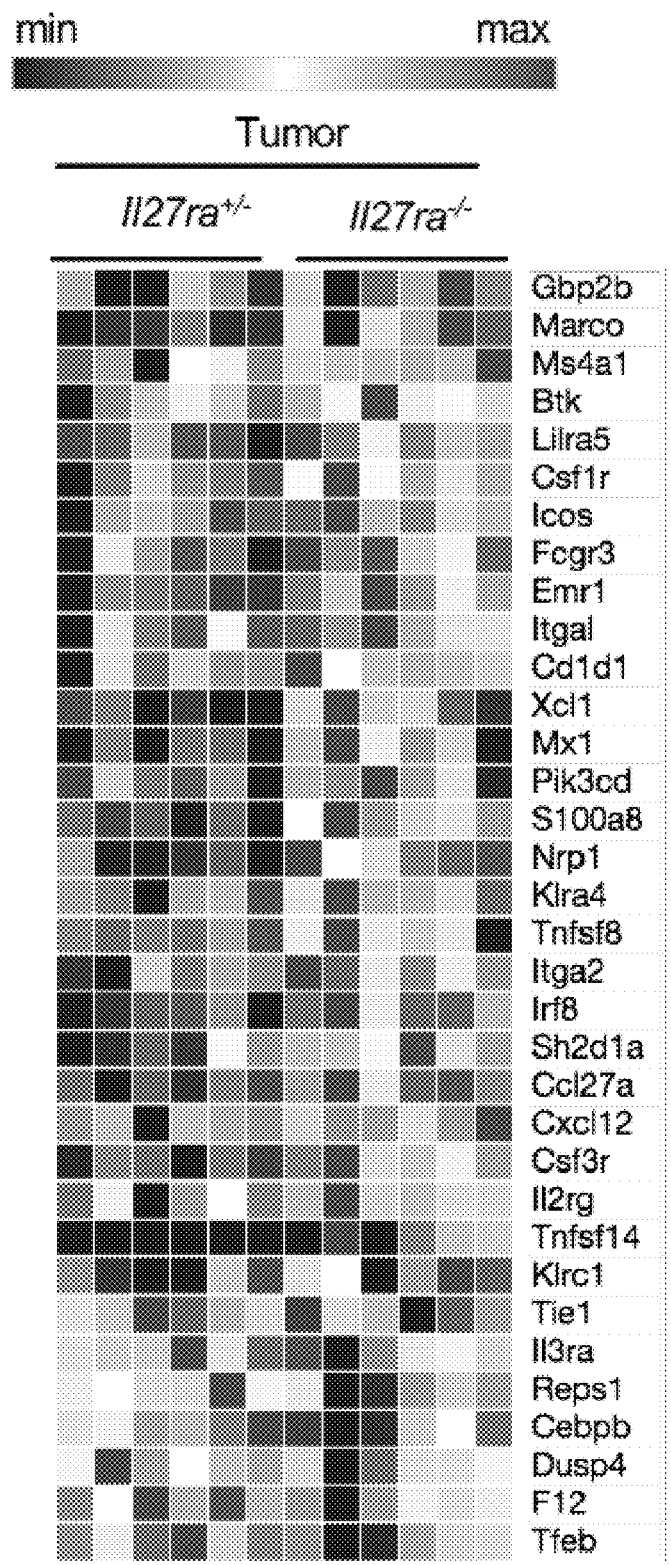
Figure 2B:
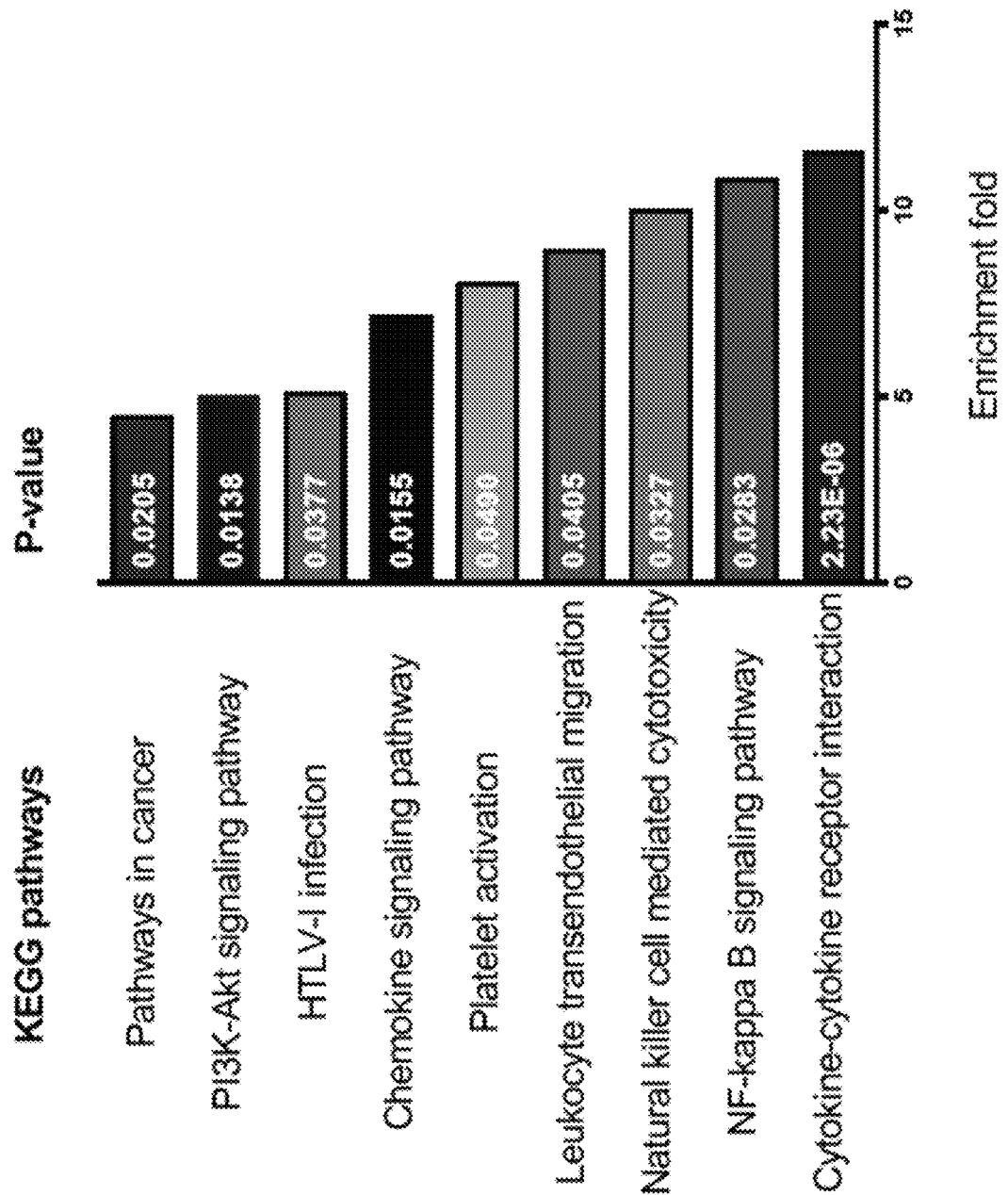
Figure 2C:
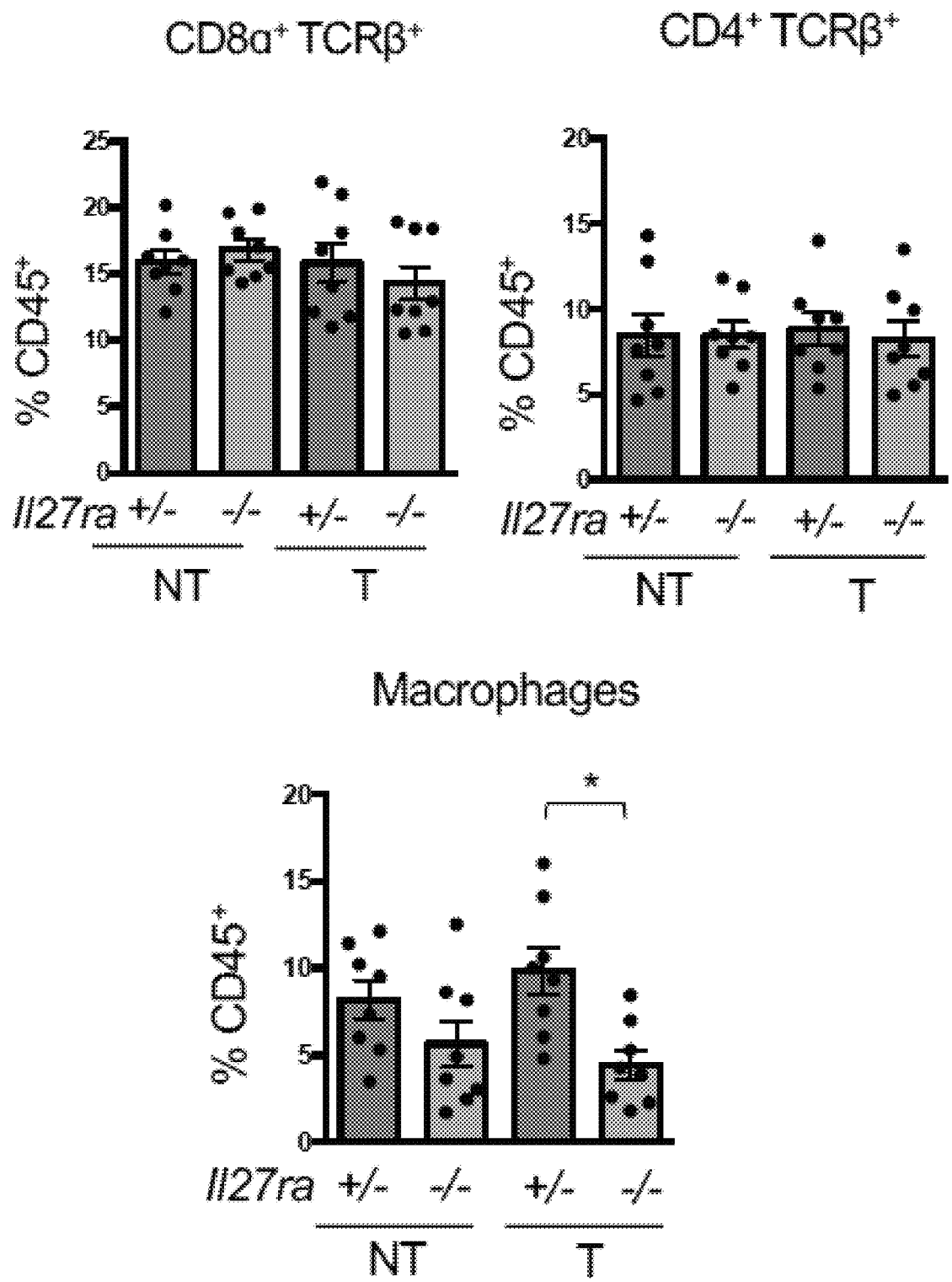
Figure 2D:
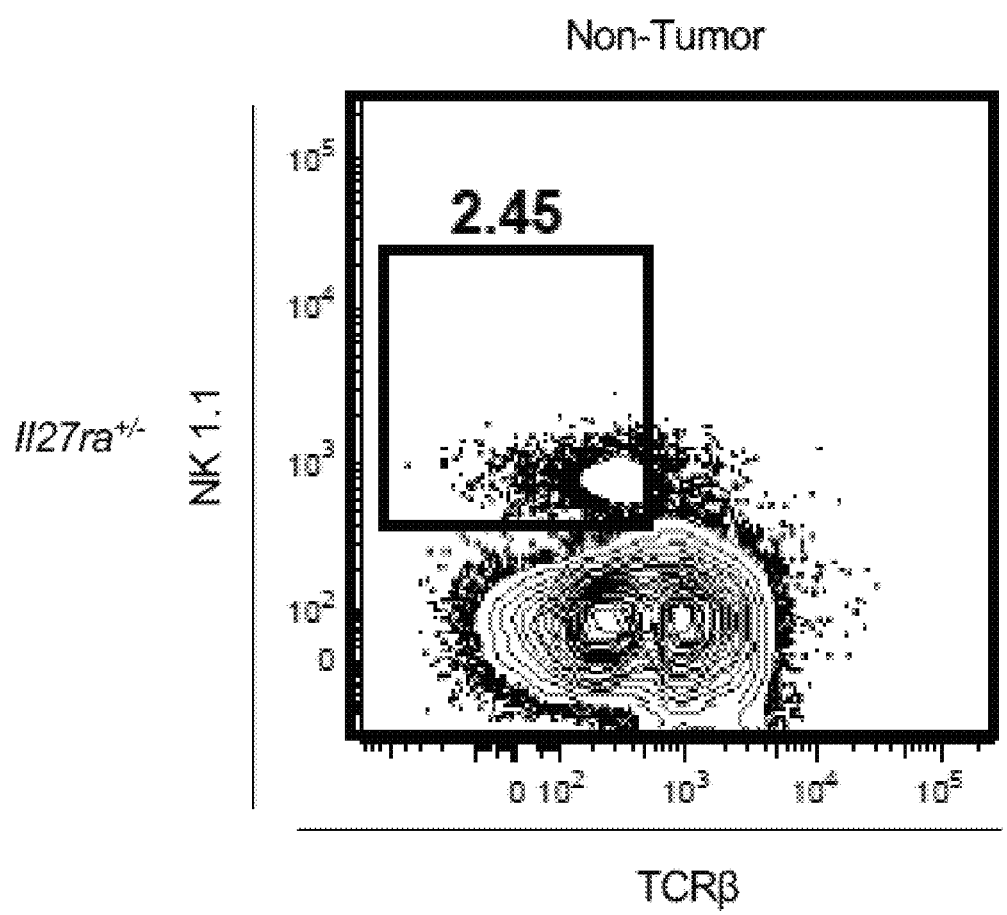
Figure 2D:
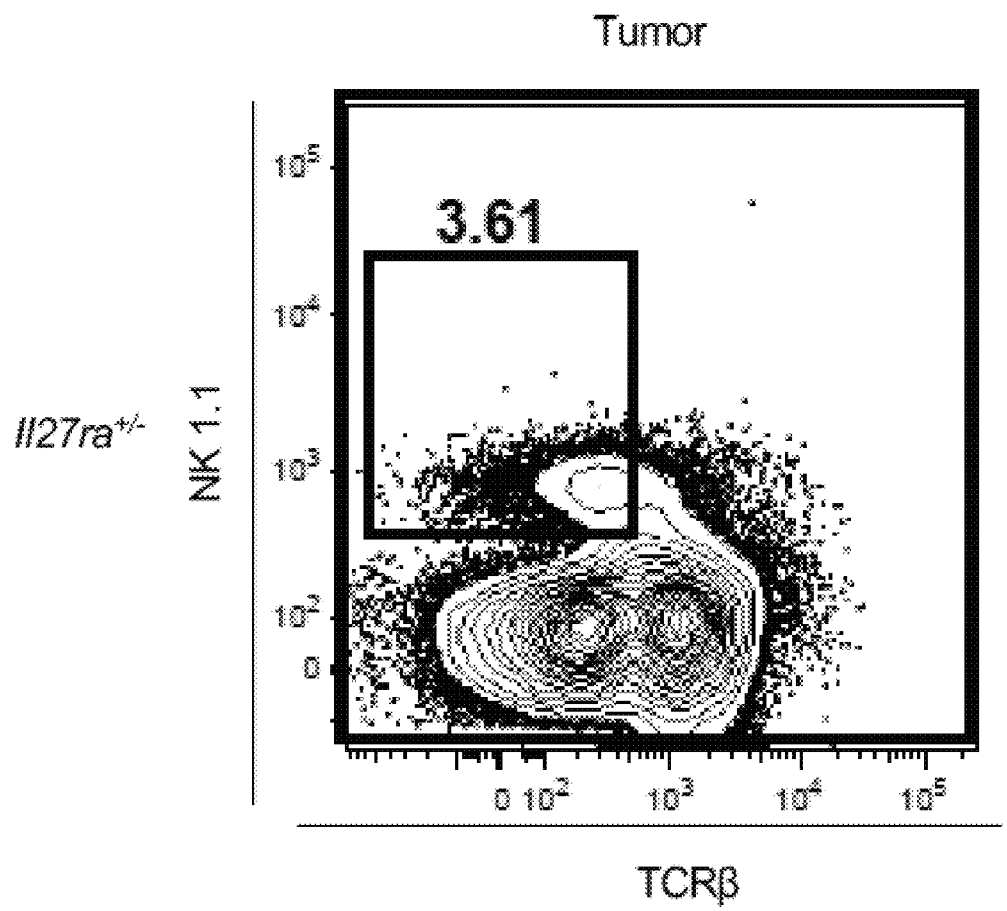
Figure 2D:
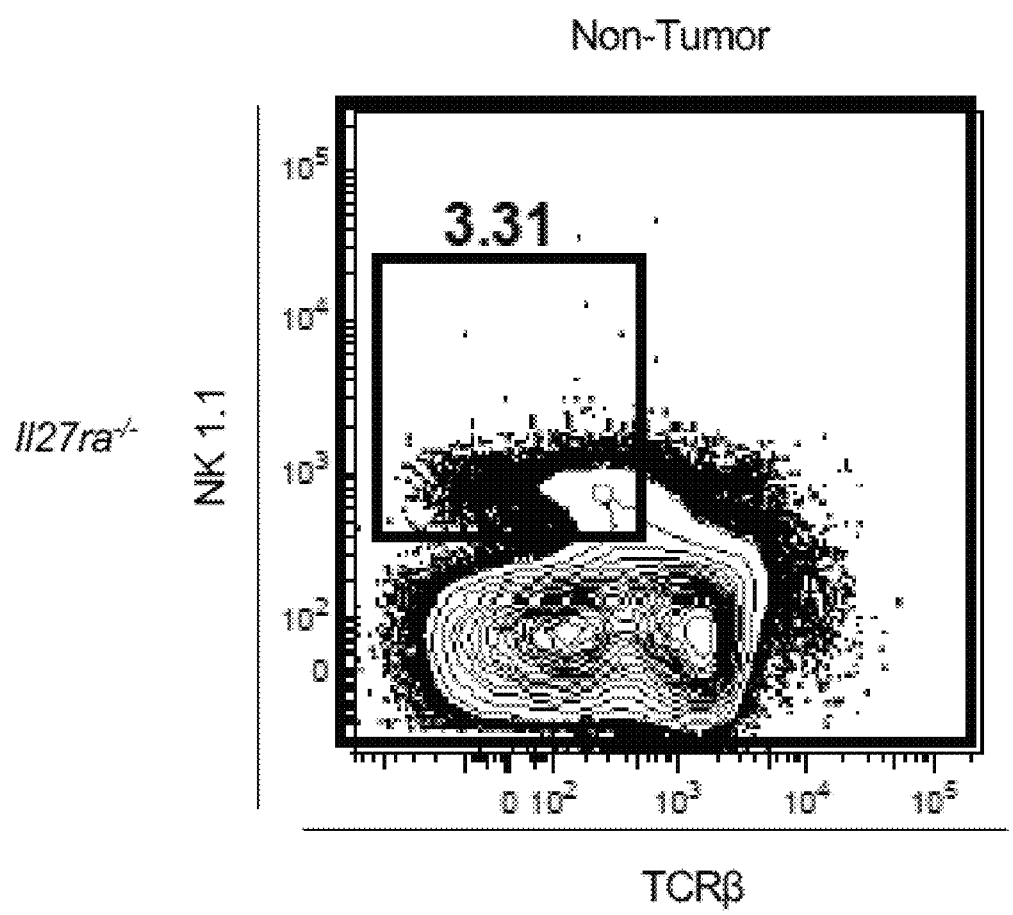
Figure 2D:
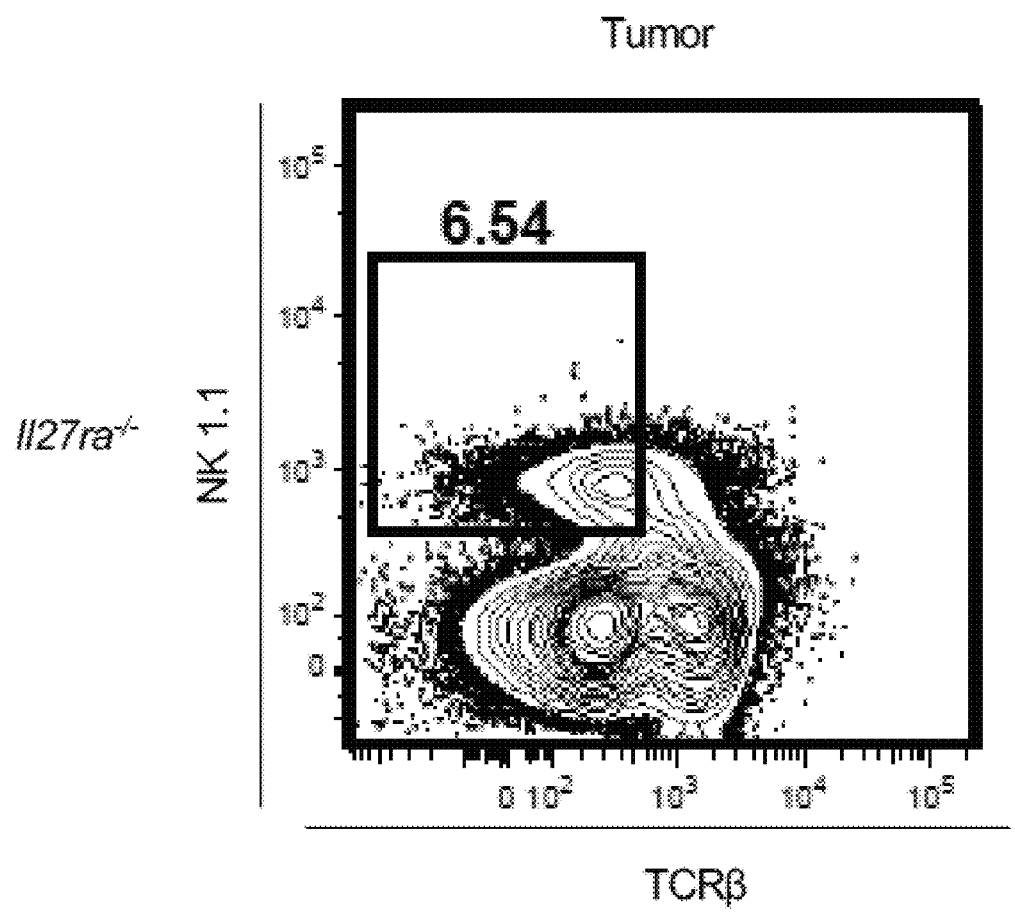
Figures 2E, 2F:
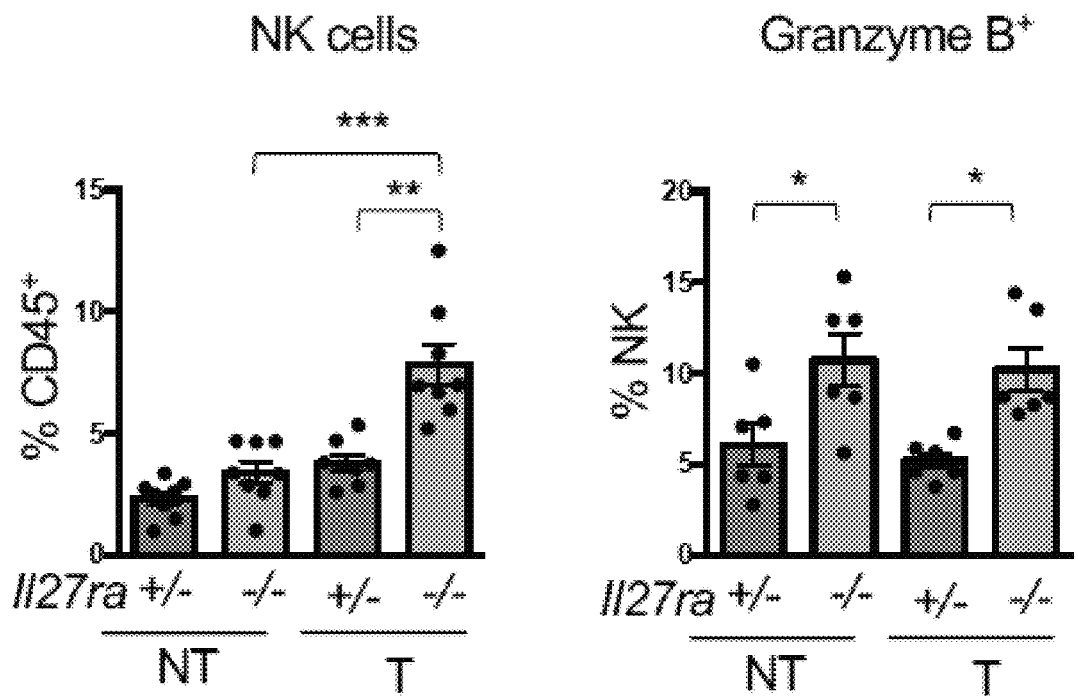
Figure 2G:
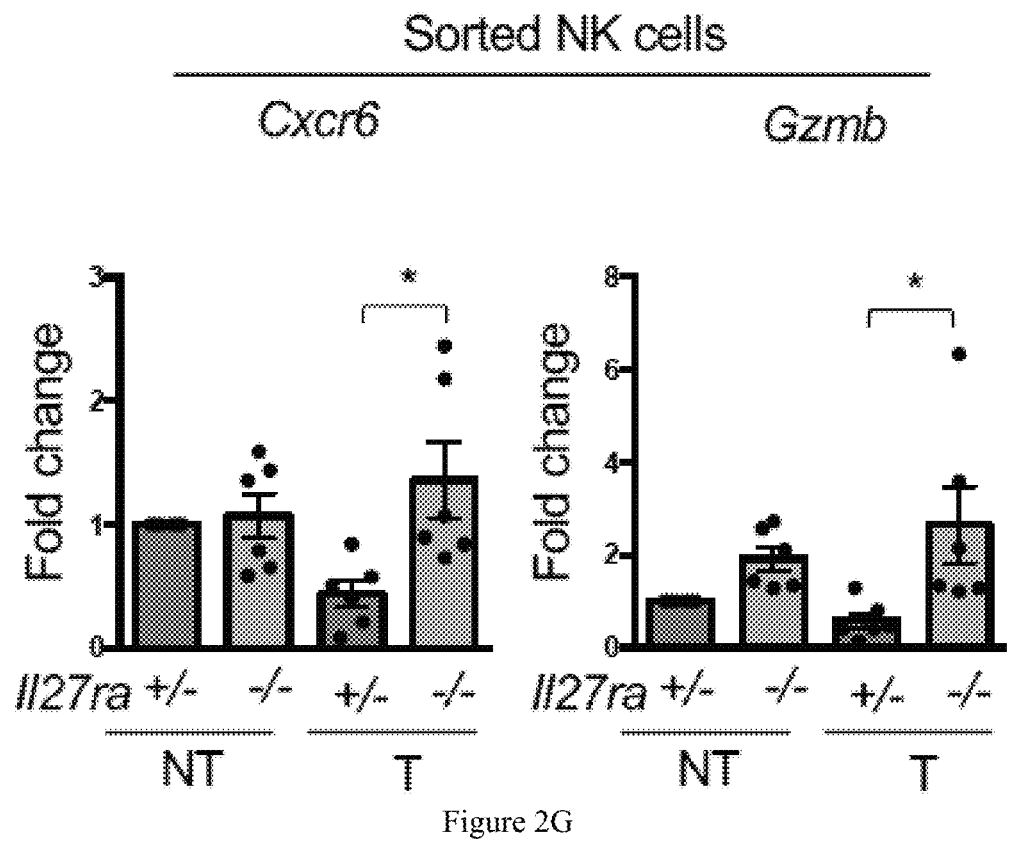
Figure 3D:
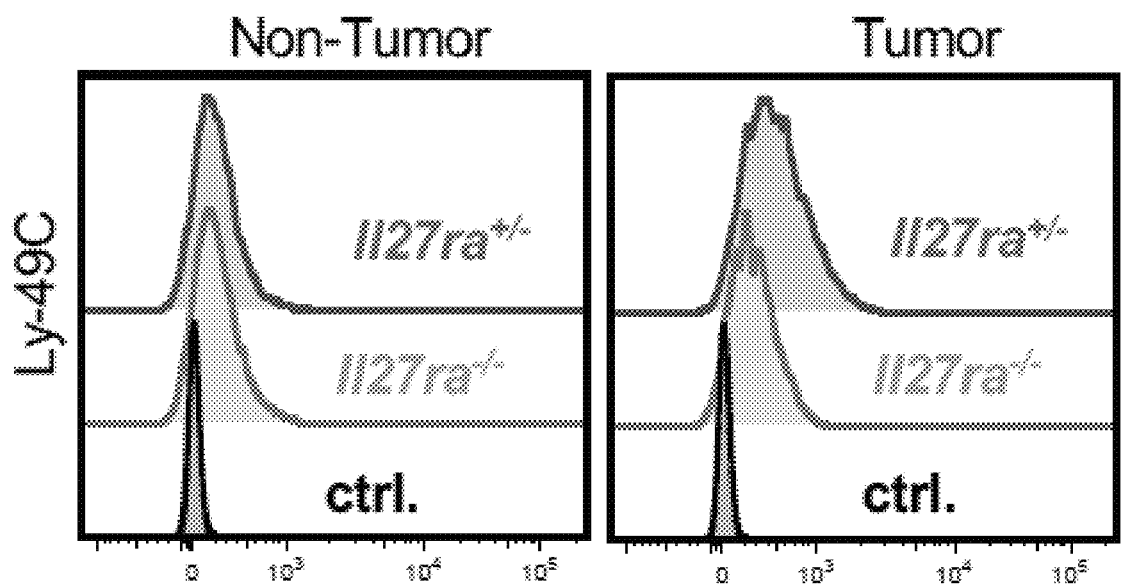
Figure 3E:
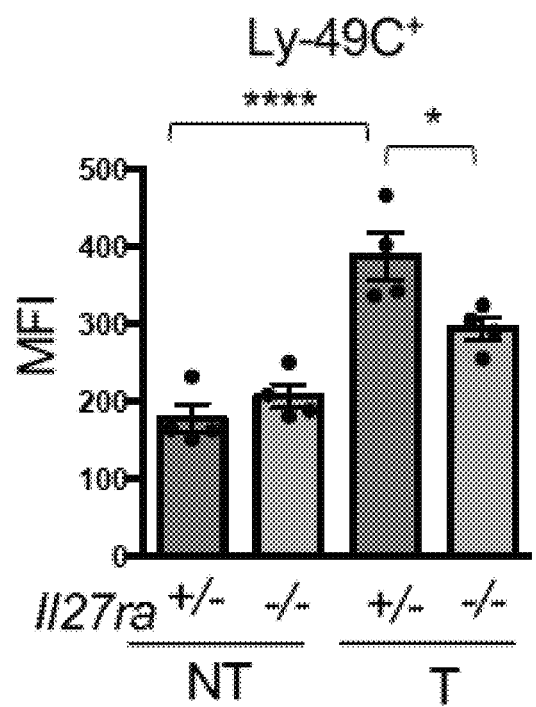
Figure 3F:
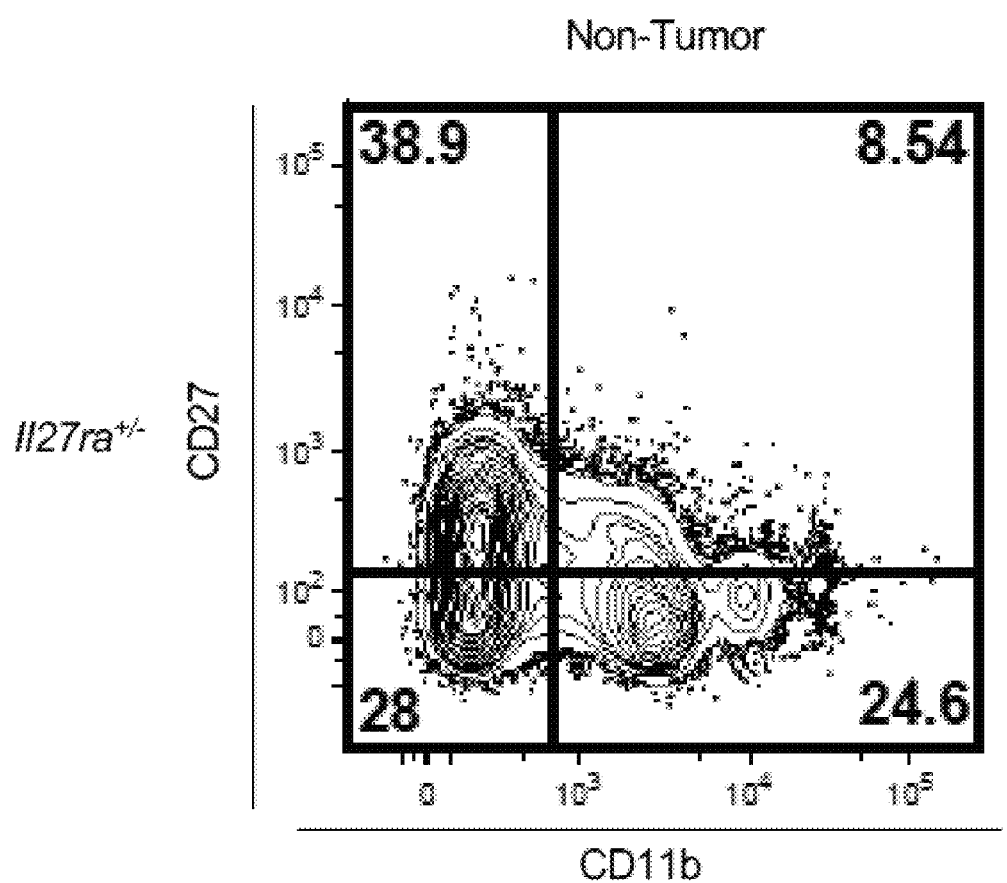
Figure 3F:
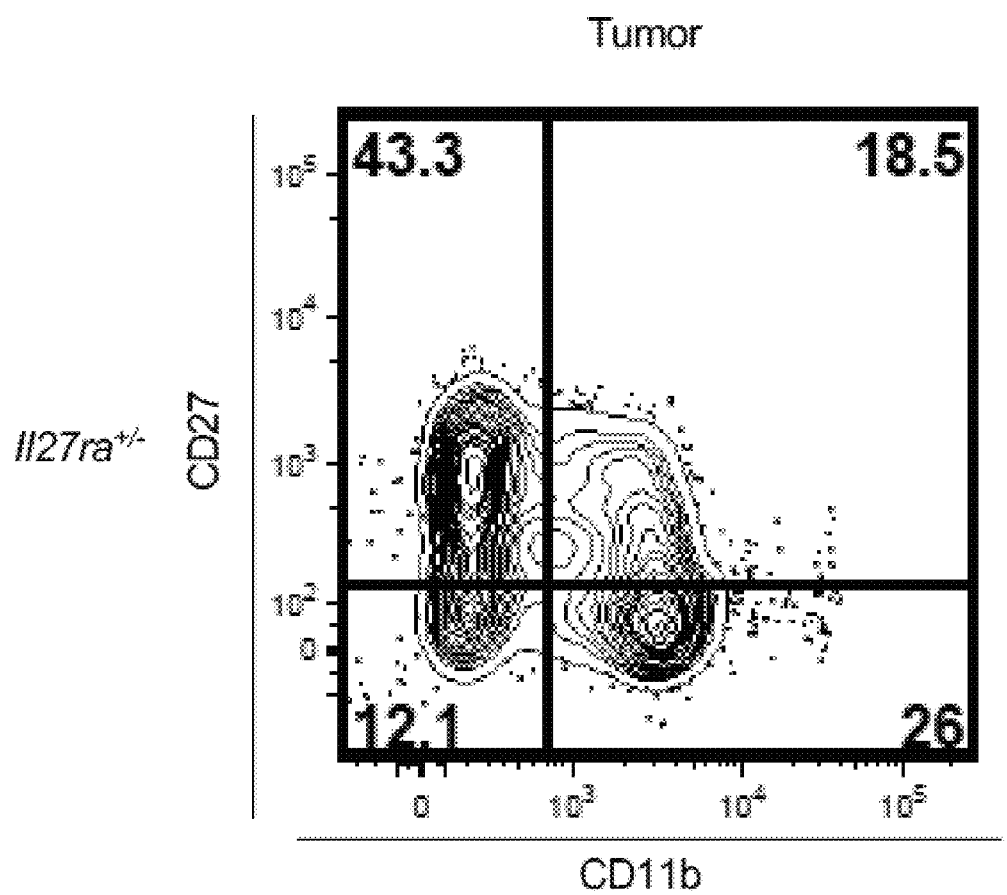
Figure 3F:
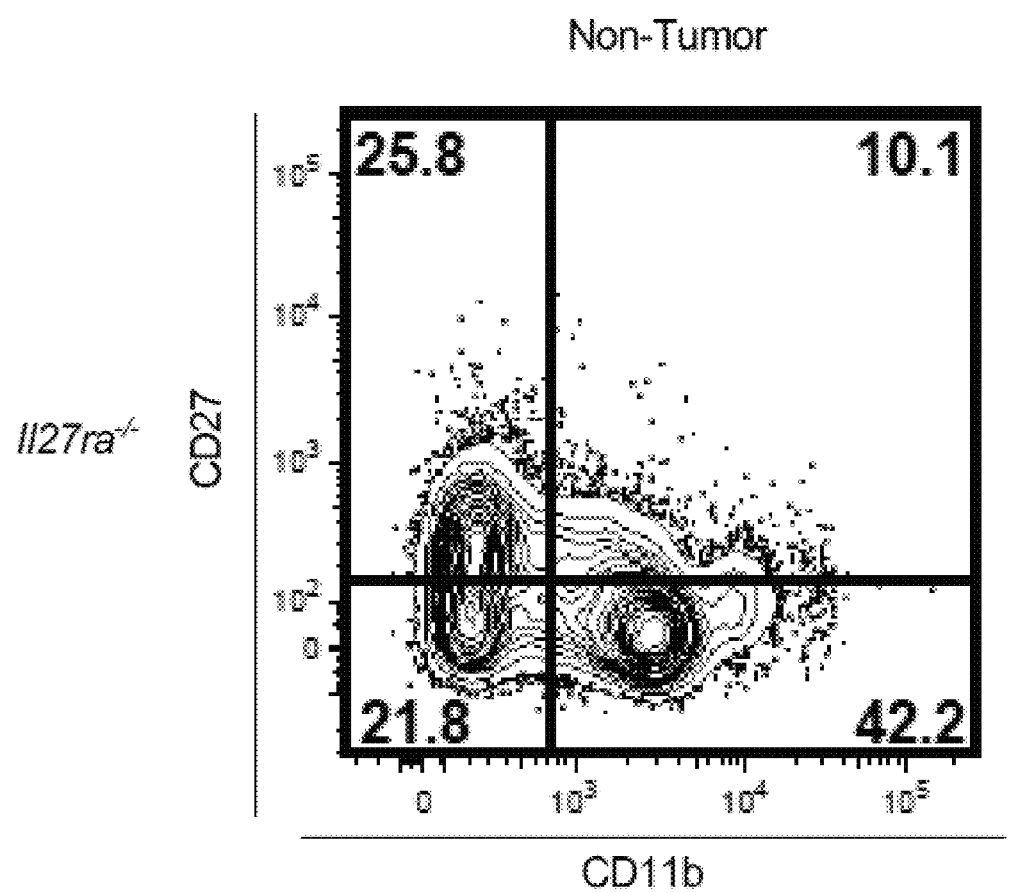
Figure 3F:
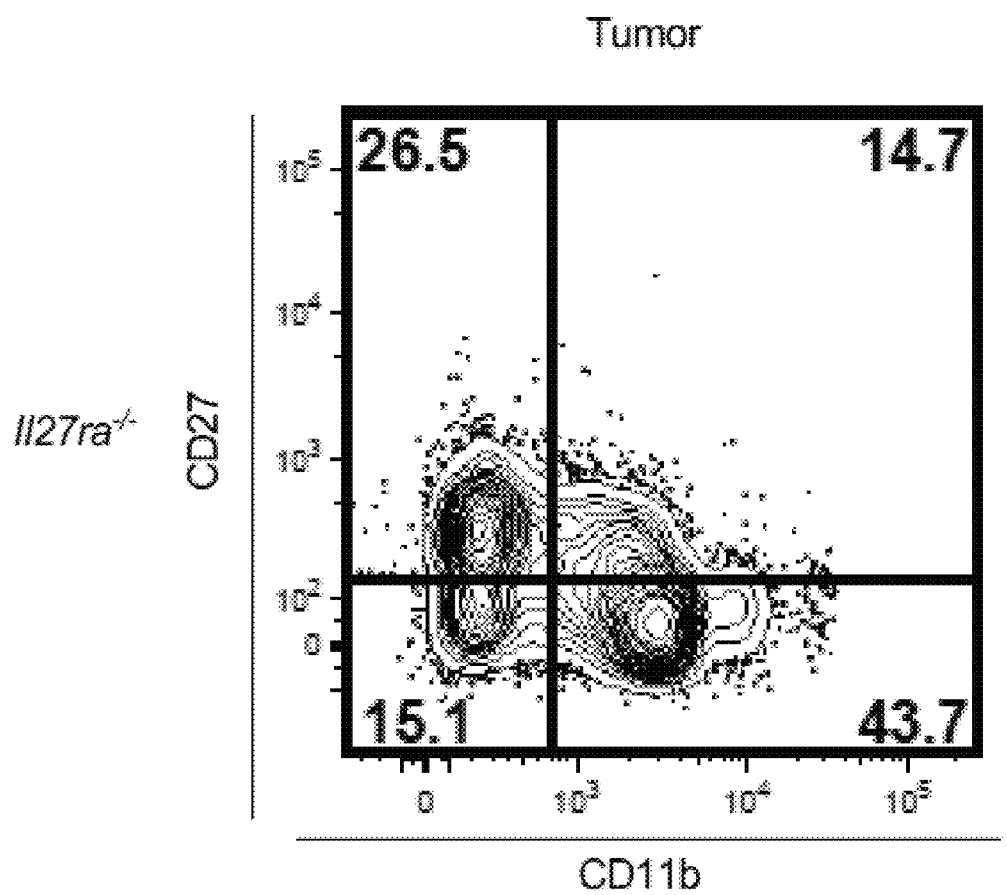
Figure 3G:
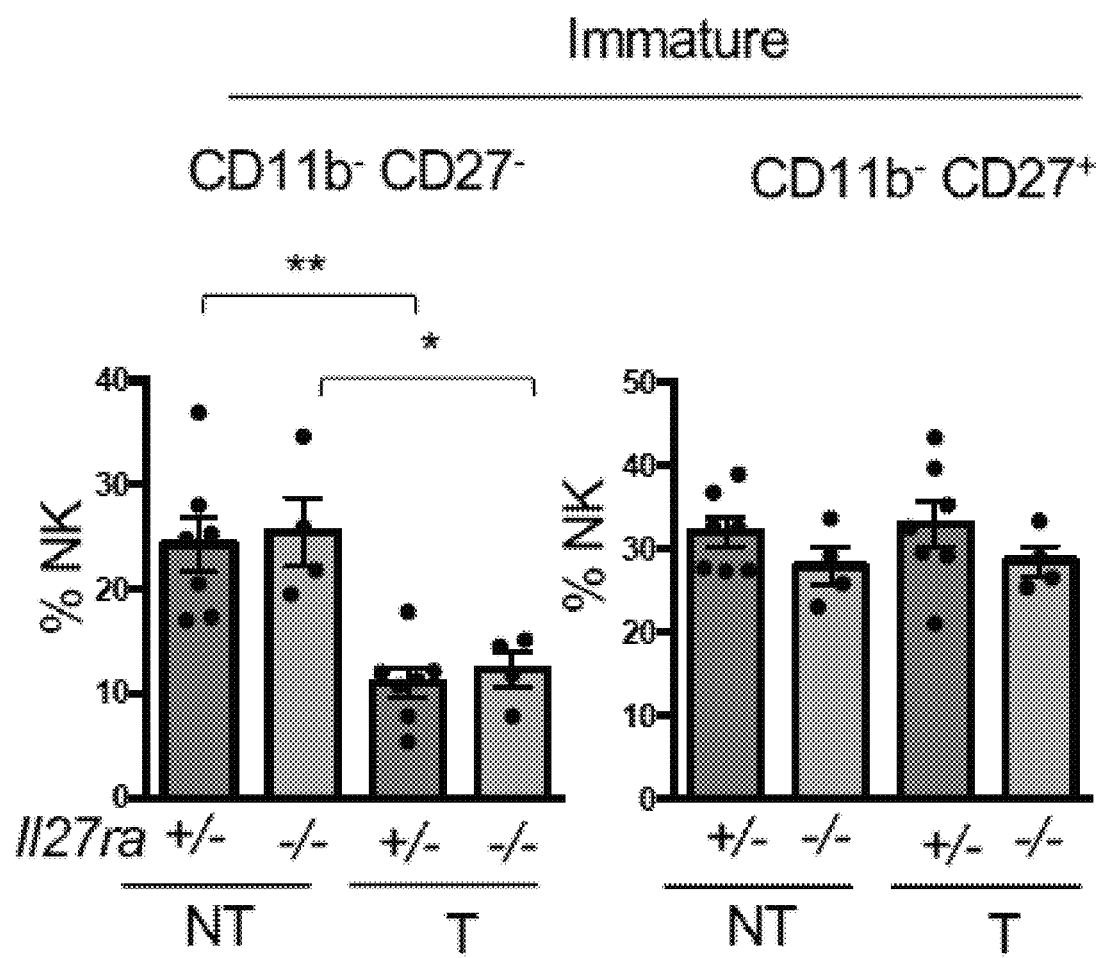
Figure 3G:
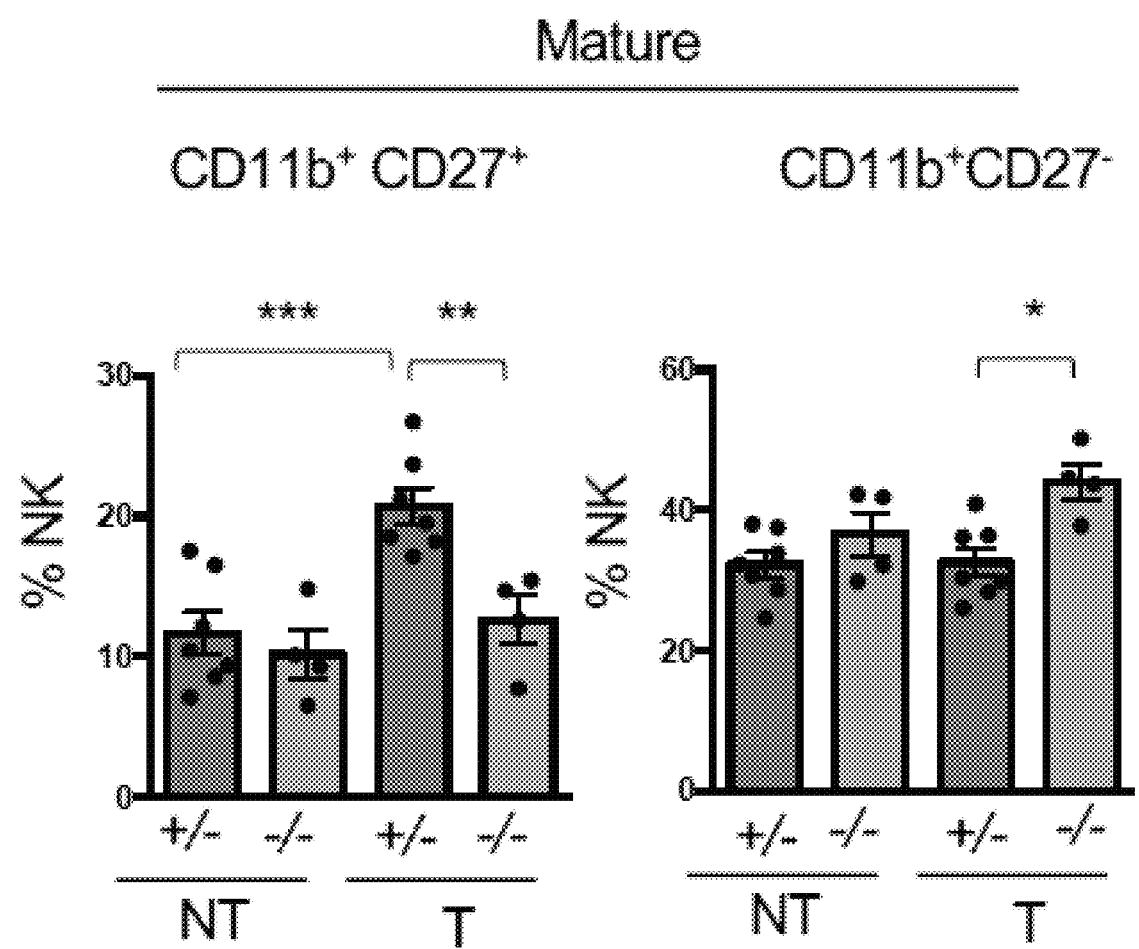
Figure 3H:
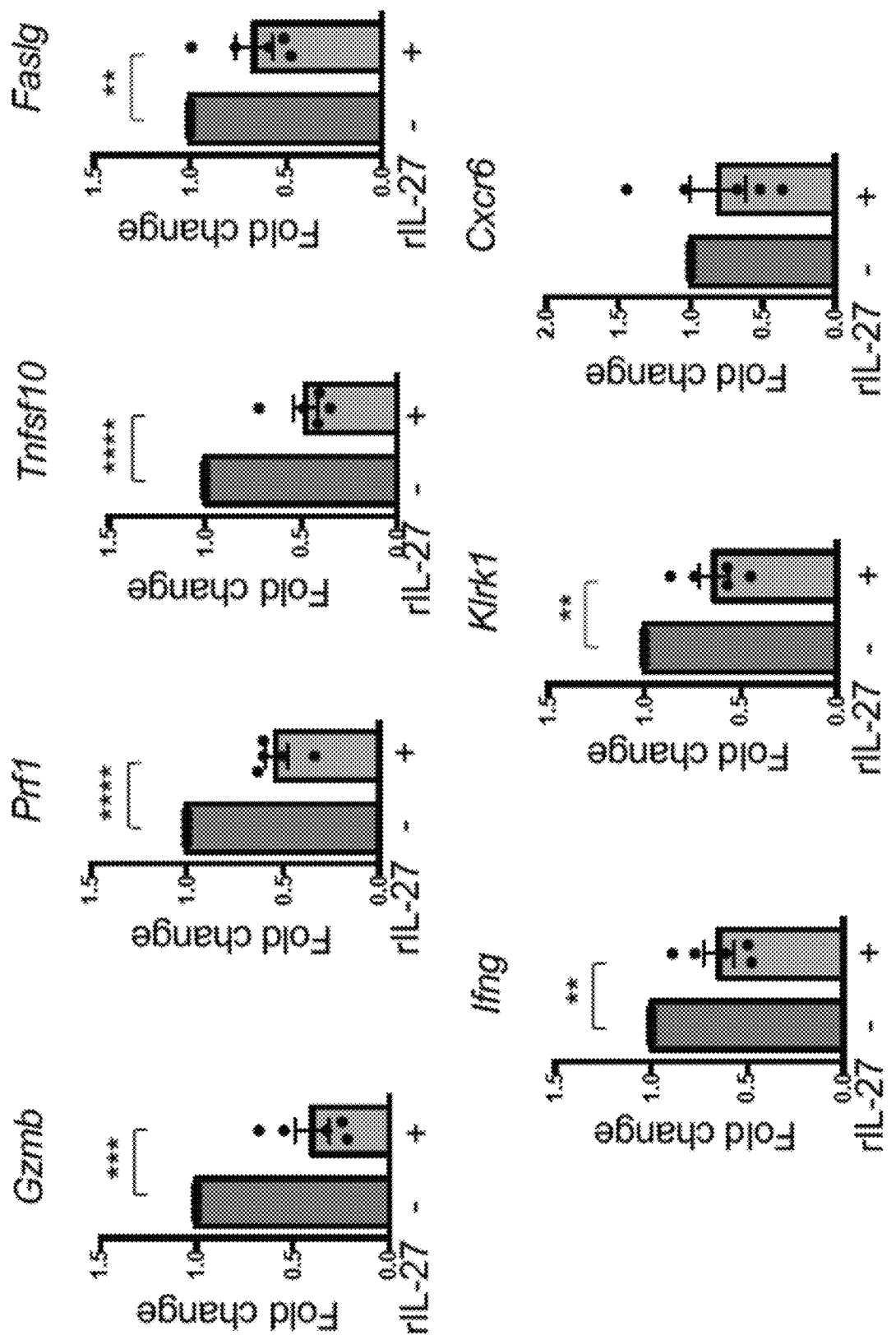
Figure 4A:
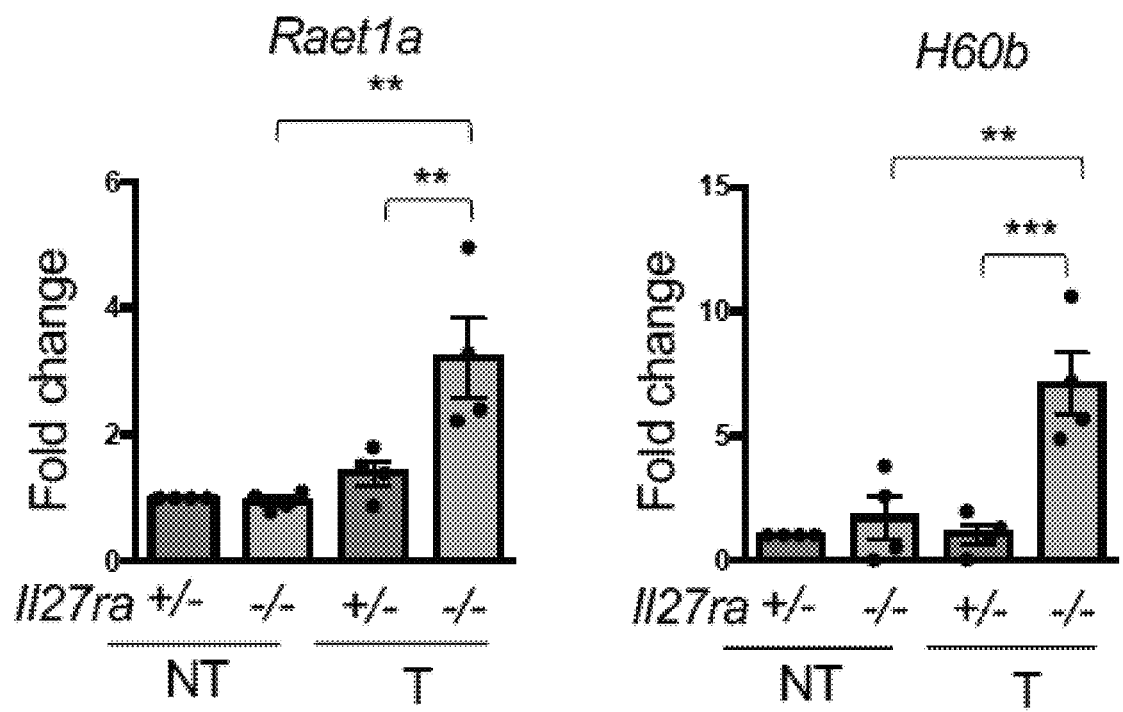
Figure 4B:
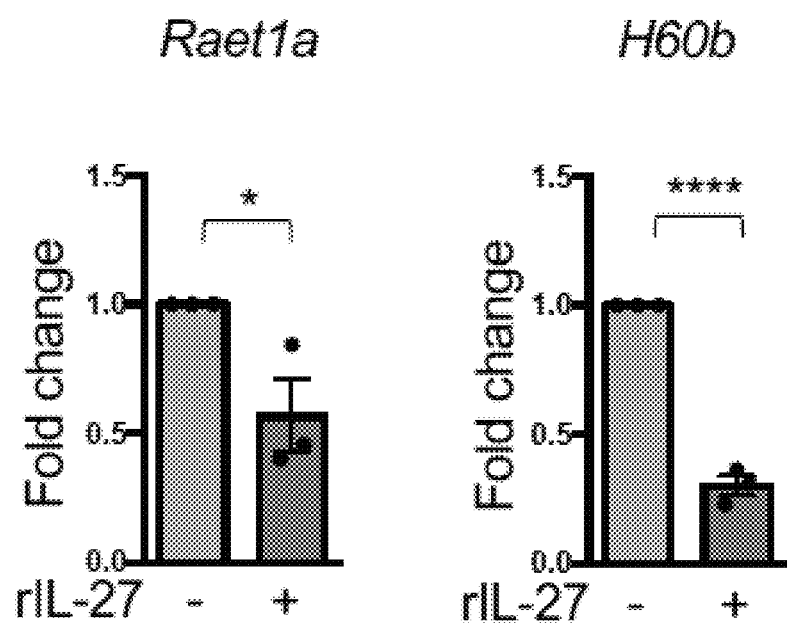
Figure 4C:
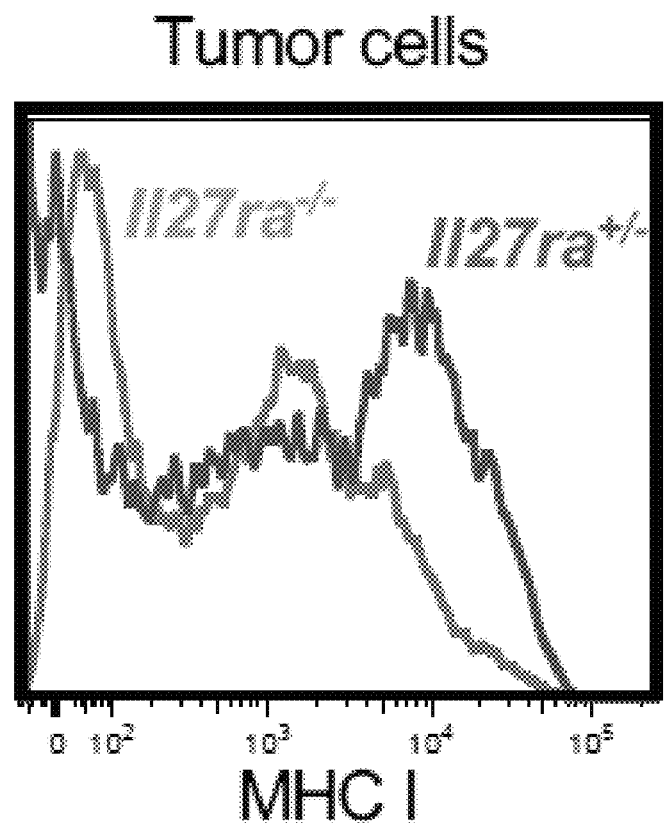
Figure 4D:
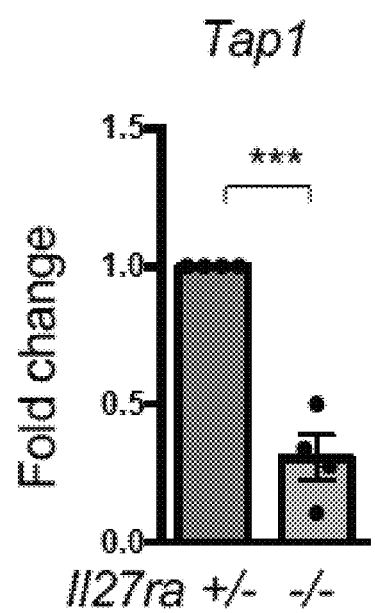

The analysis of immune cell composition in tumor and adjacent non-tumor tissue by flow cytometry revealed no differences in CD4 or CD8 T cell infiltration with some reduction of macrophages in tumors of Il27ra$^{-/-}$ mice (see, FIG. 2C). However, in concert with our gene expression data, we found a significant increase in NK cells in tumors of IL-27R deficient mice compared to IL-27R sufficient controls (see, FIGS. 2D and 2E). These NK cells were characterized by elevated Granzyme B production as determined by flow cytometry and Q-RT-PCR analysis on FACS sorted NK cells from HCC tumors and adjacent normal tissue (see, FIGS. 2F and 2G), suggesting their enhanced activation and cytolytic potential. Sorted NK cells also expressed higher level of Cxcr6, a chemokine receptor that is characteristically expressed on hepatic NK cells and regulates their accumulation (Stegmann et al., Sci. Rep., 2016, 6, 26157; and Hudspeth et al., J. Autoimmun., 2016, 66, 40-50 (see, FIG. 2G).

Example 4: IL-27R Acts as Immunological Checkpoint Taming NK Cell Activation in HCC NK cell activation is controlled by multiple activating and inhibitory receptors, which regulate their "active" versus "inactive" state (Long et al., Annu. Rev. Immunol., 2013, 31, 227-258). NKG2D activating receptor engagement by "stress molecule" ligands on target cells increases NK cell activity (Zhu et al., J. Immunol., 2010, 185, 7480-7486; Phillips et al., Stem Cells, 2013, 31, 1829-39; and Shi et al., Proc. Nat'l. Acad. Sci. U.S.A., 2018, 115, 11808-11813), while inhibitory receptor Ly-49C engages MHC class I ($H-2K^b$ and $H-2D^b$) on target cells and dampens NK cell activation (Phillips et al., Stem Cells, 2013, 31, 1829-39; and Long, Immunol. Rev., 2008, 224, 70-84).

Therefore, next we analyzed the expression of NK cell activating and inhibitory receptors in IL-27R sufficient and deficient mice. We found upregulation of activating receptor NKG2D (see, FIGS. 3A and 3B) and NKG2A, a marker of less mature NK cells that educates $CXCR6^+$ liver-resident NK cells (Stegmann et al., Sci. Rep., 2016, 6, 26157; and Lunemann et al., J. Leukoc. Biol., 2019, 105, 1331-1340) (see, FIG. 3C) and downregulation of inhibitory receptor Ly-49C on NK cells (Choi et al., J. Immunol., 2011, 186, 3911-3917) isolated from HCC tumors of $Il27ra^{-/-}$ mice (see, FIGS. 3D and 3E).

Next, we analyzed whether IL-27R signaling affects the maturation of NK cells. We found elevated presence of terminally differentiated mature $CD11b^+CD27^-$ NK cells (Hayakawa et al., J. Immunol., 2006, 176, 3, 1517-1524) in HCC tumors from $Il27ra^{-/-}$ mice, suggesting potential inhibiting role of IL-27R on NK cell maturation (see, FIGS. 3F and 3G). In contrast, more of cytokine-producing mature $CD11b^+CD27^+$ NK cells (Hayakawa et al., J. Immunol., 2006, 176, 3, 1517-1524) were found in tumors of $Il27ra^{-/-}$ control animals (see, FIG. 3G). No significant changes in NKG2D, NKG2A or Ly-49C expression were detected in blood or spleen suggesting their site-specific activation (see, FIGS. 10A and 10B).

To further understand functional implication of IL-27 signaling in controlling NK cell activity, we performed an in vivo cytotoxicity assay using RMA-S (sensitive to NK killing) and RMA (insensitive) tumor cell lines. Cells were dye-labeled and injected i.p. at 1:1 ratio into naïve $Il27ra^{-/-}$ and $Il27ra^{-/-}$ mice. After 48 hours, flow cytometry analysis of the peritoneal lavage revealed a reduced percentage of RMA-S cells in $Il27ra^{-/-}$ mice compared to $Il27ra^{-/-}$ controls, suggesting enhanced NK cell cytotoxicity towards the sensitive line in the absence of IL-27R (see, FIGS. 10C, 10D, and 10E). Taken together, these data suggest that IL-27R signaling is implicated into the regulation of NK cell accumulation, activation and cytotoxicity during HCC development.

To test whether IL-27 can directly regulate NK cells, sorted NK cells from wild type mice were stimulated in vitro with rIL-27. We found that IL-27 was able to suppress the expression of various cytotoxic and activating molecules including granzyme B (Gzmb), perforin (Prf1), TRAIL (Tnfsf10), FasL (Faslg) as well as IFN-γ (Ifng) and NKG2D (Klrk1) (see, FIG. 3H) without affecting cell survival, implying its direct role in suppressing NK effector phenotype.

In order to further characterize the link between liver injury, IL-27R signaling and NK cell accumulation, we analyzed livers from mice subjected to acute carcinogen-induced liver injury. Eight-week-old $Il27ra^{+/-}$ and $Il27ra^{-/-}$ mice were administered with 100 mg/kg DEN and gene expression in the liver was analyzed 48 hours later by Q-RT-PCR. We found strongly elevated expression of Cxcl9 and Cxcl10 chemokines as well as Prf1, Gzmb, and Ifng in the livers of DEN-treated $Il27ra^{-/-}$ mice (see, FIGS. 10F and 10G), indicating that IL-27R controls NK cell recruitment and/or activation during early and late stages of HCC development and may counteract early immunosurveillance exerted at the level of tumor seeds.

Example 5: IL-27R Signaling Regulates NK Cell Activation Through Repression of "Stress Ligand" Expression Activation of NK cells requires engagement of activating receptors on NK cells with corresponding stress-induced ligands on target cells. In particular, NK cell activation is dependent on RAE-1 and H60 families of activating ligands (Raulet et al., Annu. Rev. Immunol., 2013, 31, 413-441; and Molfetta et al., Int. J. Mol. Sci., 2017, 18) and is further enhanced by MHC I downregulation, a "missing self" signal on target cells (Shifrin et al., Semin. Immunol., 2014, 26, 138-144). We analyzed the expression of stress ligands, Raet1a and H60b in normal or tumor tissues of mice with DEN-induced HCC. Q-RT-PCR analysis revealed a significant upregulation of both Raet1a and H60b expression in tumors of $Il27ra^{-/-}$ mice compared to $Il27ra^{+/-}$ controls (see, FIG. 4A). Conversely, rIL-27 was able to suppress Raet1a and H60b expression in the DEN-derived primary HCC cell line (see, FIG. 4B). Furthermore, a significant downregulation of surface MHC I expression on tumor cells was observed in tumors from $Il27ra^{-/-}$ mice compared to $Il27ra^{+/-}$ controls (see, FIG. 4C), along with a reduction in Tap1 expression, a regulator of peptide loading on MHC class I molecules (see, FIG. 4D). These data imply that IL-27R signaling promotes expression of MHC I and represses upregulation of NK-triggering "stress ligands", thereby serving as a direct and indirect immunoregulator of NK cell activity and NK cell mediated anti-tumor responses.

Example 6: IL-27R Signaling Drives NASH-Induced HCC

While the incidence of liver cancer caused by Hepatitis B and C declines due to efficient therapies and vaccines (Zamor et al., J. Gastrointest. Oncol., 2017, 8, 229-242), obesity-driven HCC is on the rise (El-Serag, Gastroenterology, 2012, 142, 1264-1273; Wallace et al., Expert Rev. Gastroenterol. Hepatol., 2015, 9, 765-79; and Gupta et al., Amer. J. Clin. Oncol., 2018, 41, 874-881). Obesity drives the development of non-alcoholic steatohepatitis (NASH), strongly promoting HCC (Younossi, J. Hepatol., 2019, 70, 531-544). To complement our studies in toxin/mutagen-induced DEN model, we next sought to generalize our observations using a NASH-dependent model of HCC. We crossed $Il27ra^{-/-}$ mice to MUP-uPA mice where the uPA (urokinase plasminogen activator) transgene is controlled by mature hepatocyte-specific promoter (MUP). MUP-uPA expression combined with Western diet (WD) feeding drives strong fibrosis and spontaneous HCC development and overall faithfully models NASH-driven HCC in humans (Nakagawa et al., Cancer Cell, 2014, 26, 331-343; Nakagawa, World J. Hepatol., 2015, 7, 2110-2118; and Febbraio et al., Cell. Metab., 2019, 29, 18-26). MUP-uPA$^+$Il27ra$^{-/-}$ and MUP-uPA$^+$Il27ra$^{+/-}$ mice were fed the WD starting at 8 weeks of age for a total of 8 months. We did not find any significant difference in body weight (see, FIG. 1I). Similar to observations in the DEN-induced HCC model, IL-27R deficient MUP-uPA$^+$ mice were largely protected from HCC development (see, FIGS. 5A and 5B). Tumors from MUP-uPA$^+$Il27ra$^{-/-}$ mice were characterized by the reduction of Ccnd1 expression, implying reduced proliferative capacity of tumors in the absence of IL-27R signaling (see, FIG. 5C). We also observed a reduction of collagen content in livers of MUP-uPA$^+$Il27ra$^{-/-}$ mice, suggesting limited fibrosis in the absence of IL-27R signaling (see, FIG. 5D). The level of Lcn2 was decreased in tumors of IL-27R deficient MUP-uPA$^+$ mice (see, FIG. 5E).

Figure 5A:
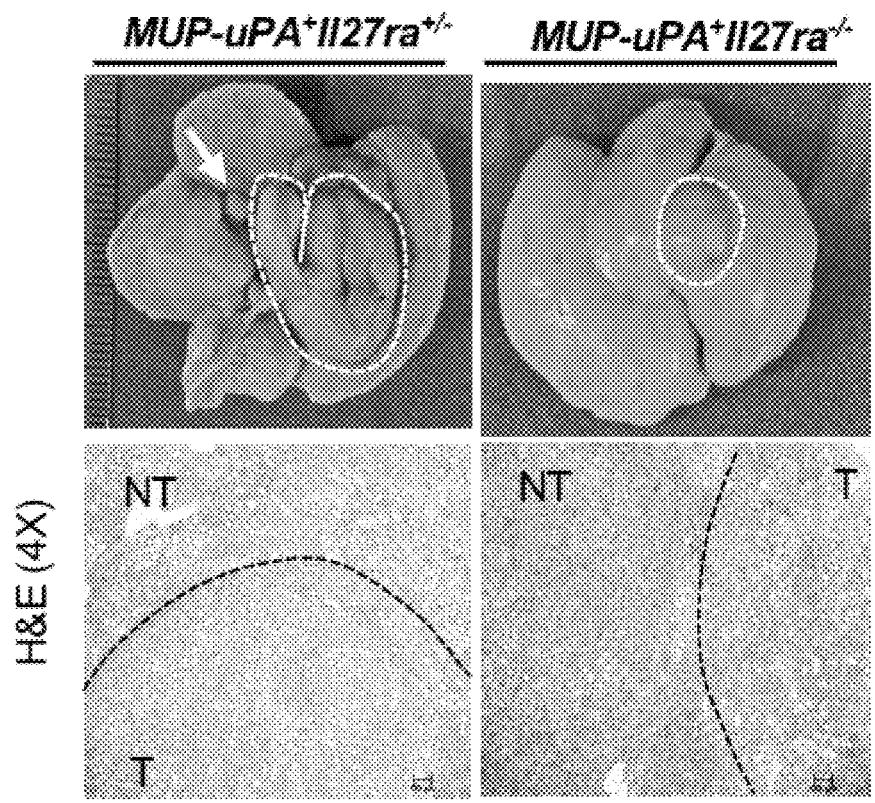
Figure 5B:
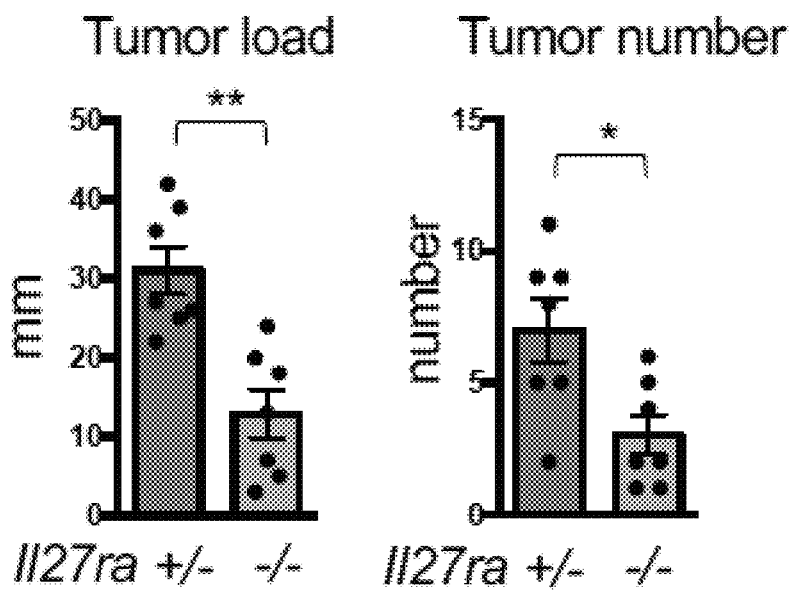
Figure 5C:
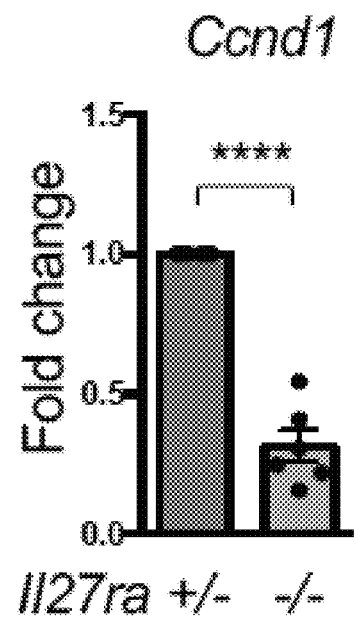
Figure 5D:
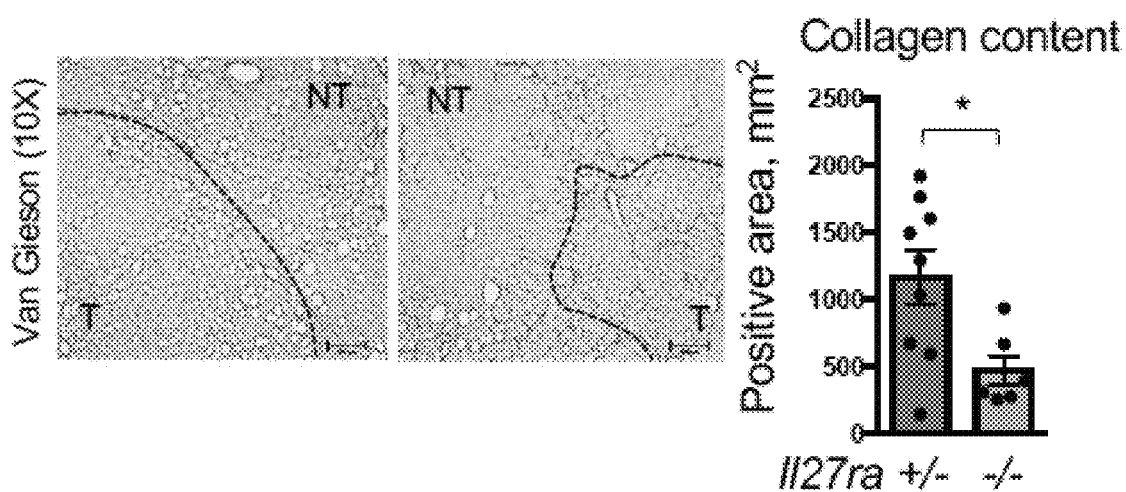
Figure 5E:
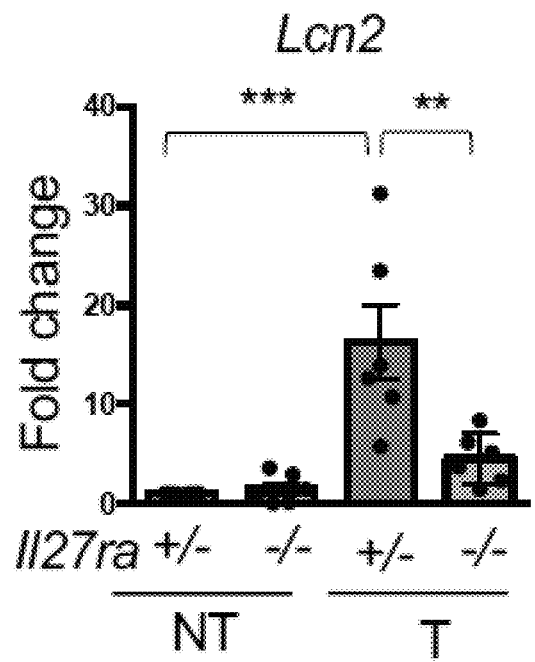
Figure 5F:
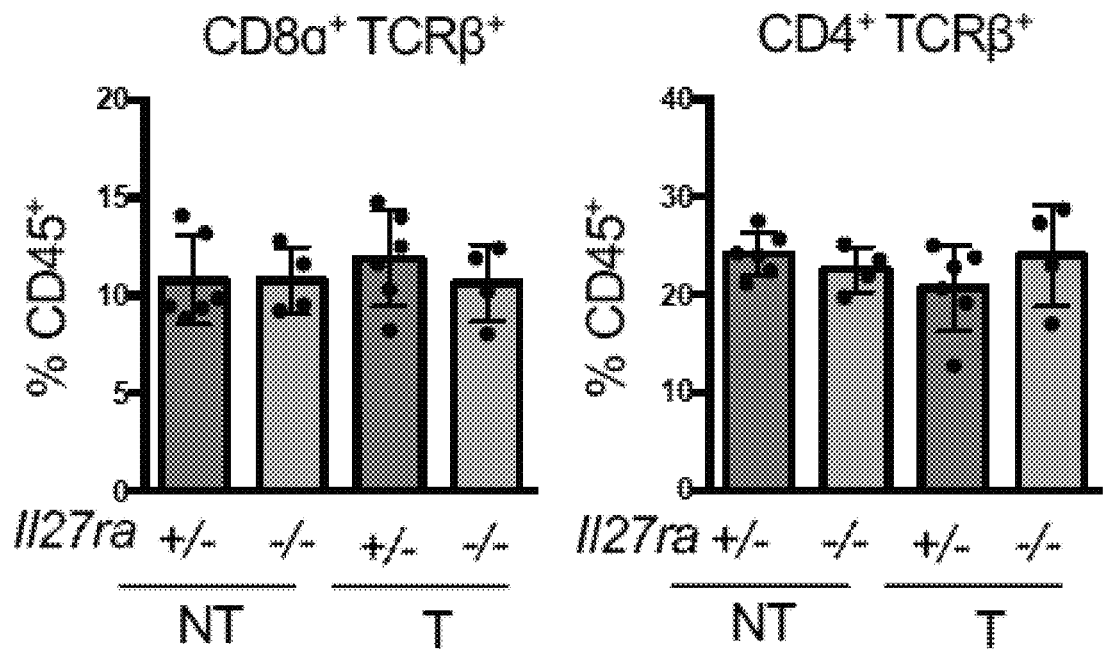
Figure 5G:
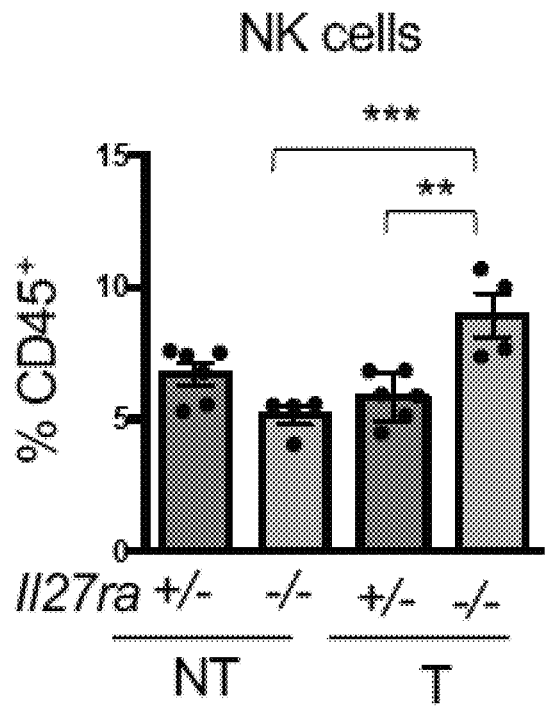
Figure 5H:
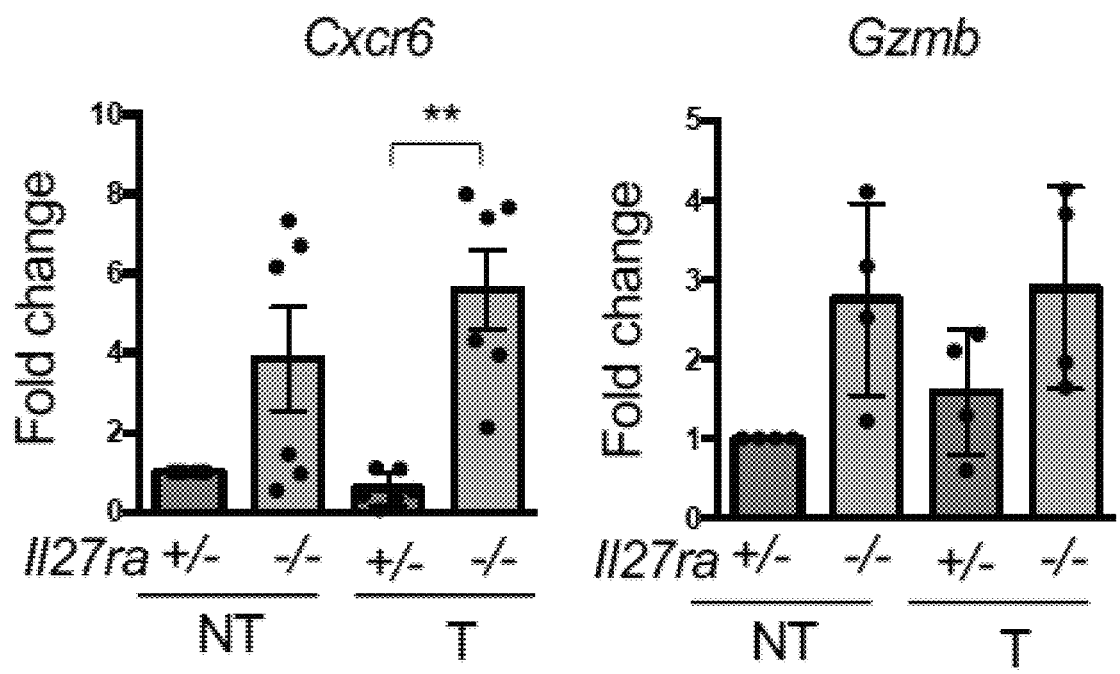
Figure 5I:
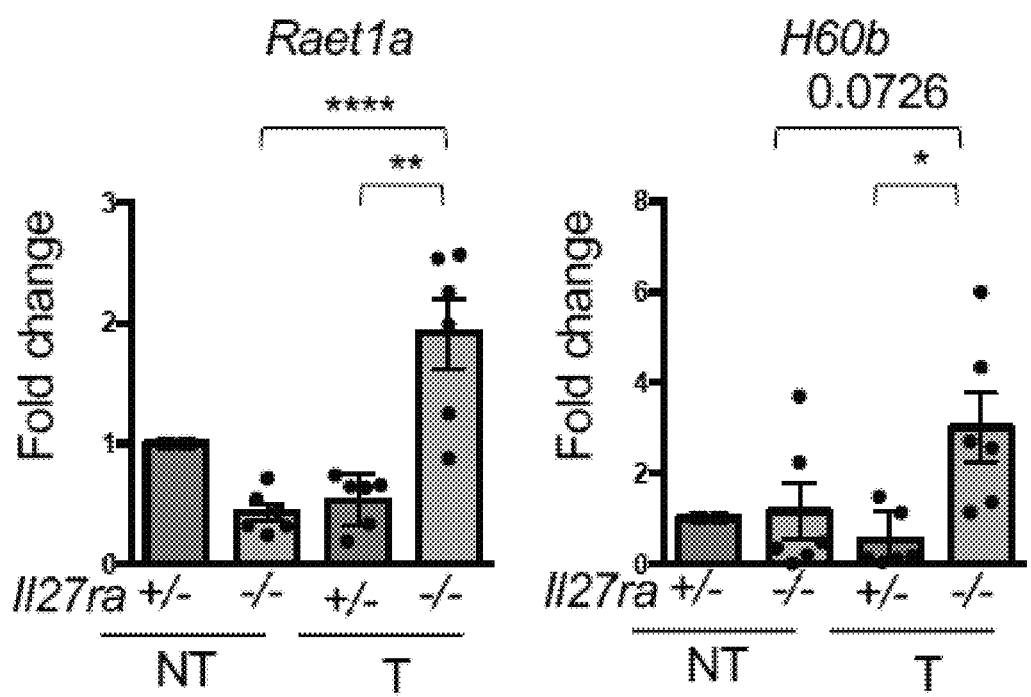
Figure 5J:
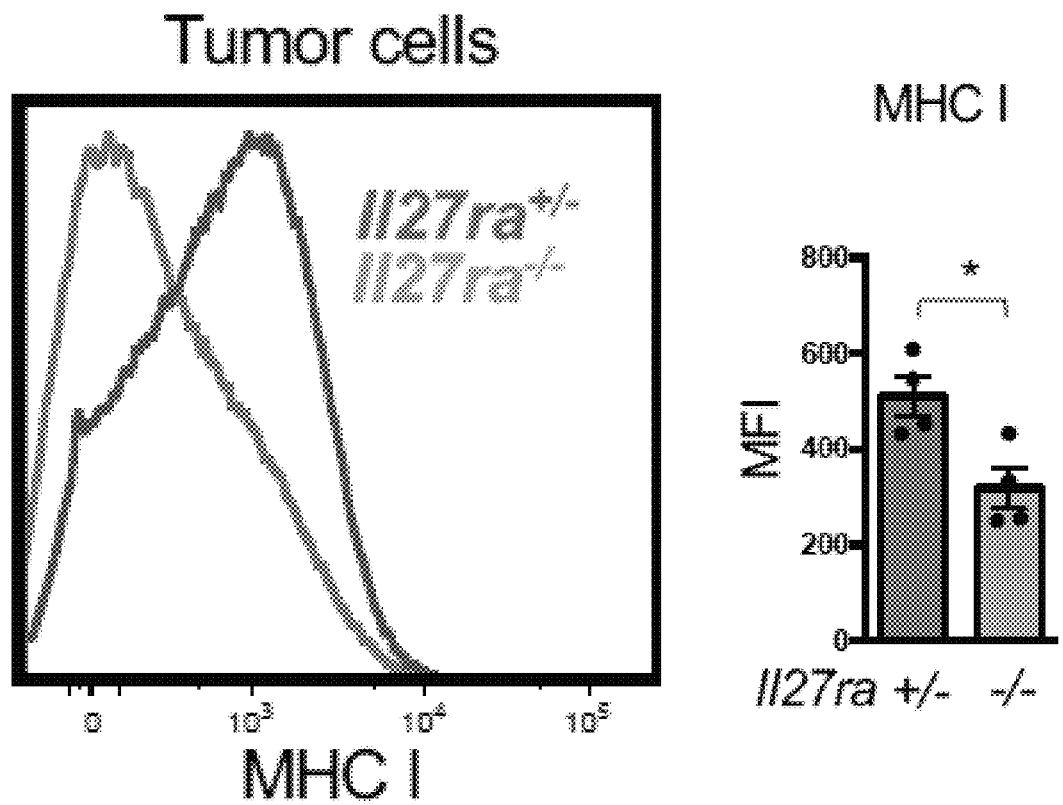
Figure 5K:
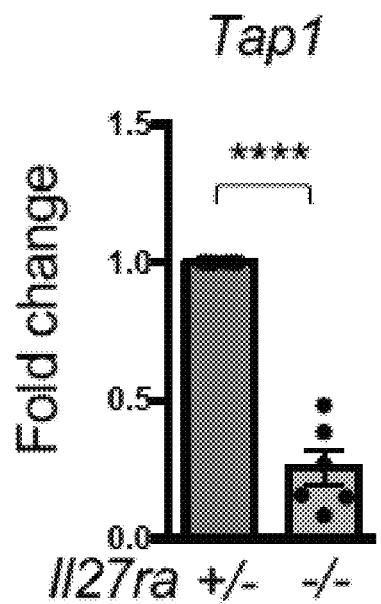

The analysis of immune cell composition revealed no changes in CD4 or CD8 T cells (see, FIG. 5F), but elevated accumulation of NK cells in tumors of MUP-uPA$^+$Il27ra$^{-/-}$ mice (see, FIG. 5G). CXCR6 (Cxcr6) and granzyme B (Gzmb) expression was also upregulated in the absence of IL-27R as determined by Q-RT-PCR (see, FIG. 5H). Consistent with the results in DEN model, we also detected heightened expression of Raet1a and H60b in tumors of IL-27R deficient MUP-uPA$^+$ mice (see, FIG. 5I) while MHC I and Tap1 were downregulated in tumors of mice lacking IL-27R (see, FIGS. 5J and 5K). These data further advanced a functional mechanistic link connecting IL-27R signaling to regulation of NK cell mediated anti-tumor immunity and HCC development in models of different etiology.

Example 7: Tumor Promoting Effect of IL-27R Signaling is Exerted Through Suppression of NK Cell Mediated Anti-Tumor Immunity Next, we sought to establish the "linearity" of the mechanistic link between IL-27R signaling, NK cell activity and HCC development. We first tested whether NK cell activity is essential for the anti-tumor effect of IL-27R ablation. We depleted NK cells using anti-NK1.1 antibody in DEN-treated Il27ra$^{-/-}$ and Il27ra$^{+/-}$ mice for total period of 5.5 months prior to tumor collection. Efficiency of NK depletion was confirmed by FACS analysis of blood, non-tumor and tumor tissues (see, FIGS. 12A and 12B). The depletion of NK cells enhanced tumor growth in Il27ra$^{-/-}$ mice and eliminated the differences between Il27ra$^{-/-}$ and Il27ra$^{+/-}$ cohorts (see, FIGS. 6A and 6B), suggesting that NK cells is a key functional immune population regulated by IL-27R in the context of HCC tumor progression.

Figure 6A:
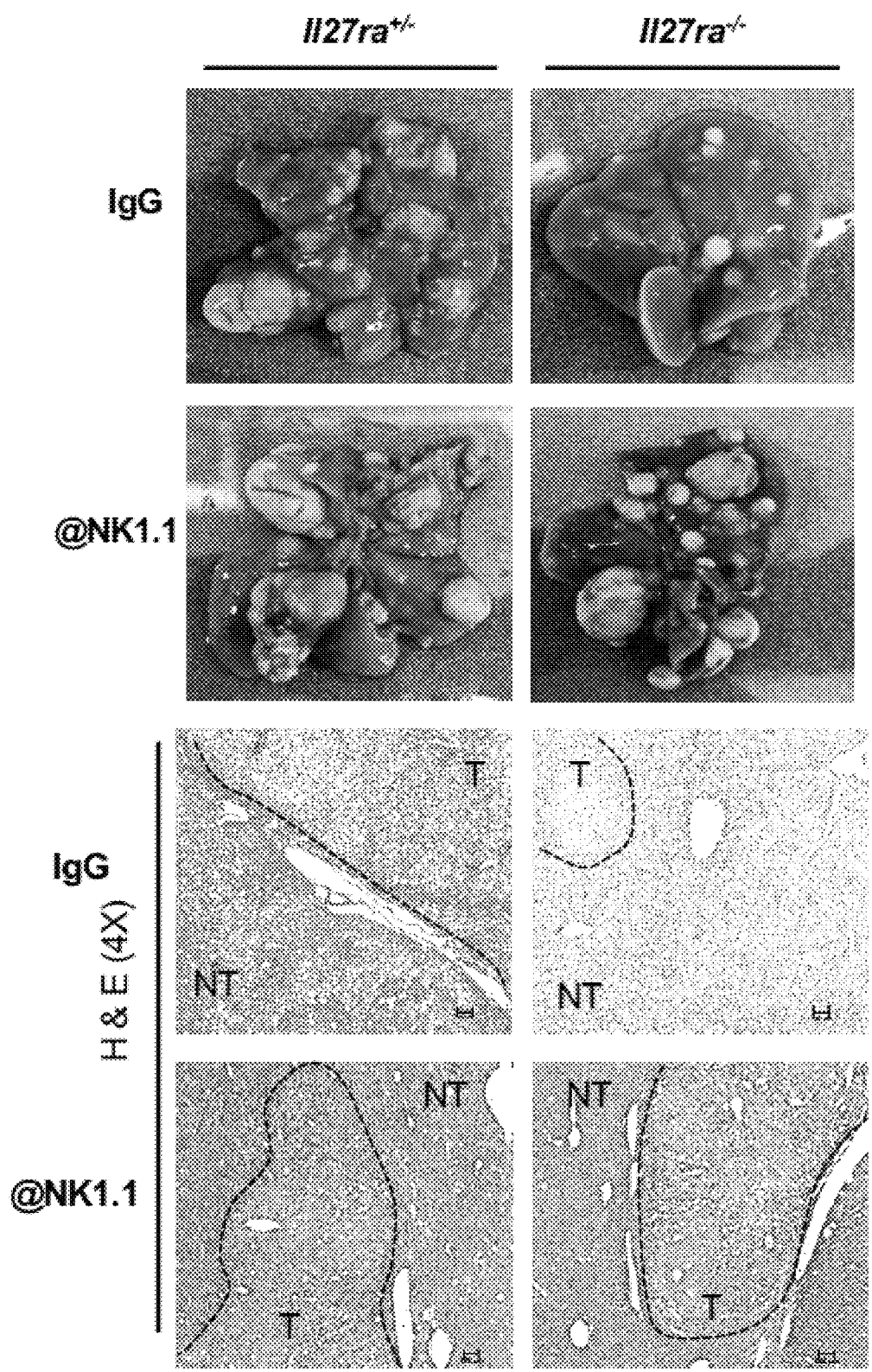
Figure 6B:
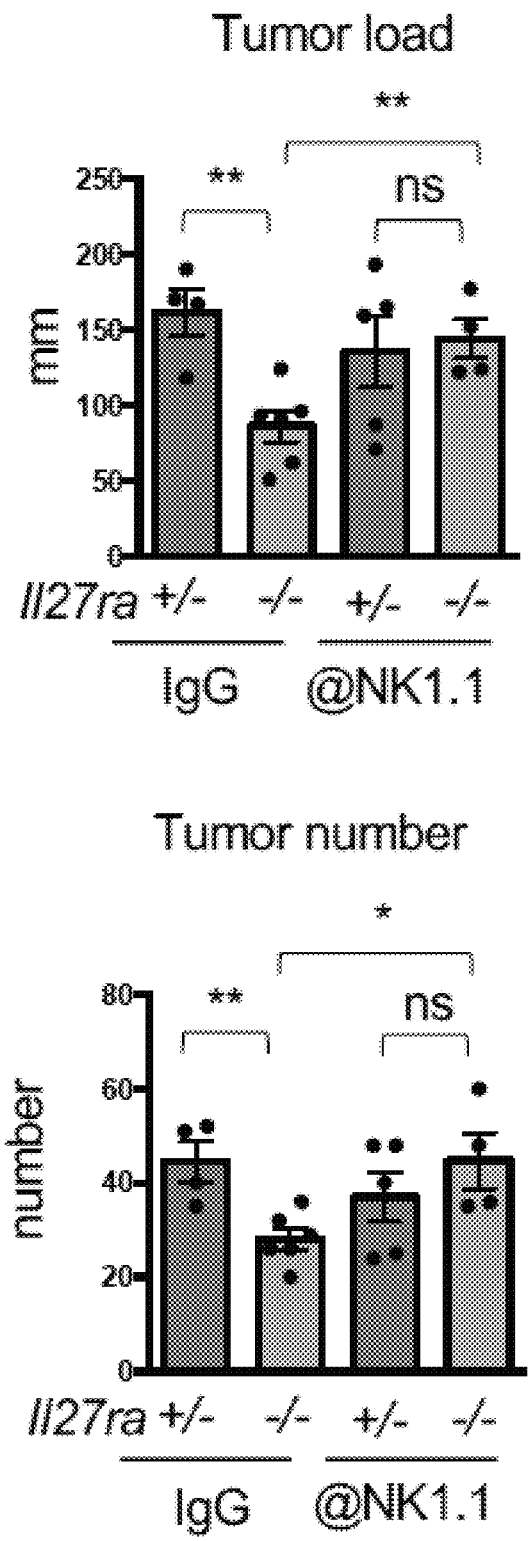
Figure 6C:
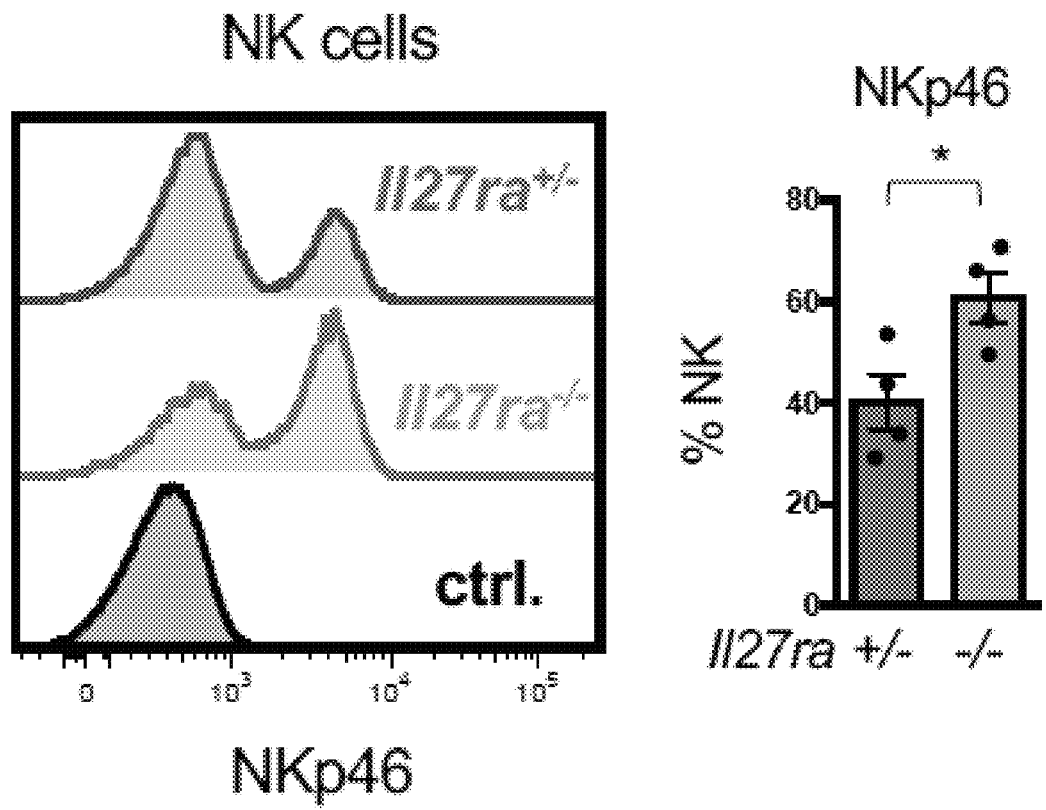
Figure 6D:
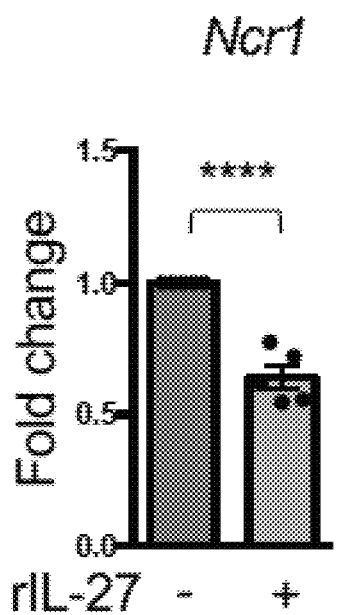
Figure 6E:
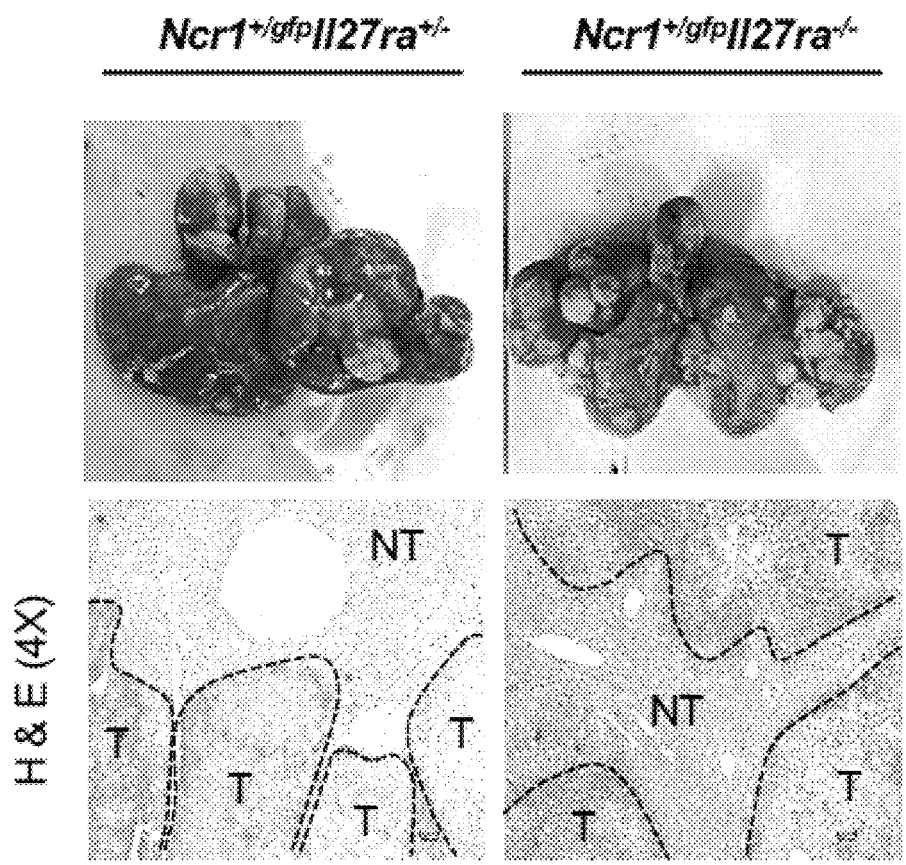
Figure 6F:
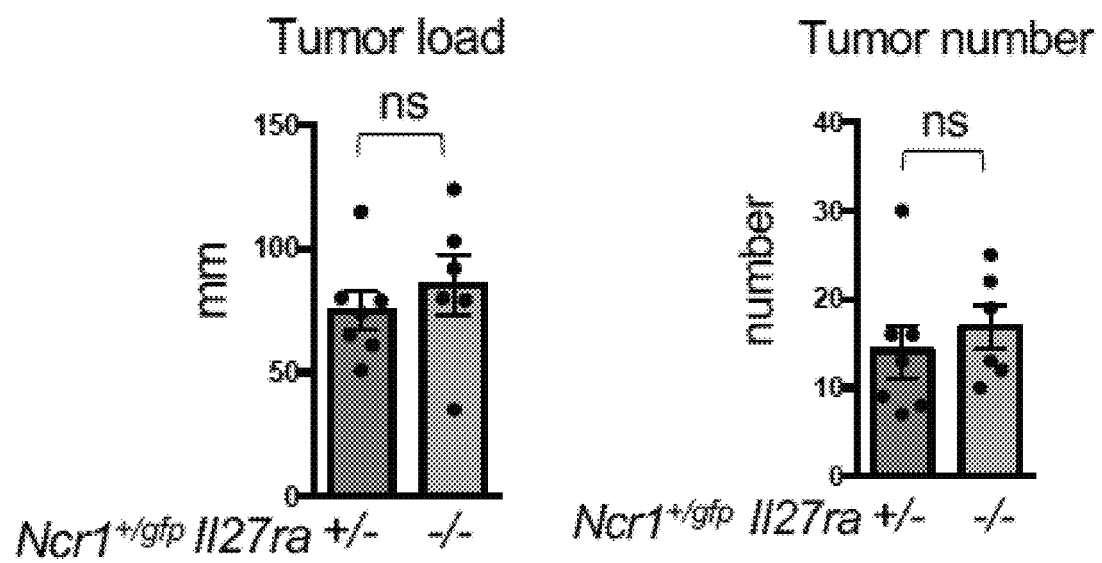

NKp46 is a natural cytotoxicity receptor expressed by NK cells (Barrow et al., Front Immunol., 2019, 10, 909). The analysis of NKp46 expression on liver NK cells revealed enrichment of NKp46+NK cells in Il27ra$^{-/-}$ mice compared to Il27ra$^{+/-}$ controls (see, FIG. 6C). Moreover, in vitro stimulation of sorted NK cells with rIL-27 suppressed NKp46 (Ncr1) expression, suggesting that IL-27R signaling could directly regulate this cytotoxicity receptor expression and therefore impact functional activity of NK cells (see, FIG. 6D). We therefore took an advantage of NKp46-GFP reporter strain (Ncr1$^{gfp/gfp}$), where Ncr1 gene is replaced by gene expressing green fluorescent protein (GFP), marking NK cells (Gazit et al., Nat. Immunol., 2006, 7, 517-23). Importantly, heterozygous or homozygous disruption of NKp46 in these mice affects expression levels of NKp46 and cell activation and differentiation (Wang et al., PLoS Biol., 2018, 16, e2004867). Ncr1$^{+/gfp}$Il27ra$^{-/-}$ and Ncr1$^{+/gfp}$Il27ra$^{+/-}$ mice were administered with DEN as previously described and tumor development was analyzed at 10 months of age. Similar to NK cell antibody depletion, reduced NK cell activation capacity in Ncr1$^{+/gfp}$ mice 'cancelled out' anti-tumor effect of IL-27R deficiency and resulted in similar tumor load and number of tumors formed in IL-27R deficient and IL-27R sufficient mice (see, FIGS. 6E and 6F compared to FIGS. 1D and 1E). Importantly, heterozygous Ncr1$^{+/gfp}$ status did not affect tumor development in IL-27R sufficient mice (see, FIGS. 6E and 6F compared to FIGS. 1D and 1E). Therefore, the presence and the activation of NK cells is required for the anti-tumor effect of IL-27R deficiency and IL-27R signaling promotes HCC development by repressing NK cell activity.

Example 8: Pharmacological Inhibition of IL-27 Suppresses Liver Cancer Development In order to test therapeutic potential of IL-27/IL-27R signaling inhibition, we administered IL-27 neutralizing antibodies (SRF381) to MUP-uPA$^+$ mice fed with WD for overall period of 8 months for last 15 weeks of WD feeding. We found a strong reduction of liver cancer development in mice received anti-IL-27 compared to cohort received IgG isotype control (see, FIGS. 7A and 7B). Gene expression analysis revealed upregulation of Gzmb (encoding Granzyme B), Tnfsf10 (encoding TRAIL) and Klrk1 (encoding NKG2D) in non-tumor and tumor tissue from mice received anti-IL-27 antibody (see, FIG. 7C), suggesting that blockade of IL-27/IL-27R signaling may suppress tumor growth via upregulation of cytotoxic mechanisms as well as NK cell activating molecules. Stronger effect was observed in non-tumor tissue, suggesting that IL-27 and its signaling is implicated into the control of immune mechanisms regulating early tumor development which is in line with our data from genetic models.

Overall, our data suggest that IL-27R signaling controls HCC tumor development in vivo as a new immunological checkpoint regulating NK cell activation and cytotoxicity. Particularly, we found that IL-27R signaling suppresses NK cell accumulation and activation by controlling the expression of activating and inhibitory receptors on NK cells, as well as MHC I and stress-induced ligands on cancer cells. Pharmacological inhibition of IL-27 significantly suppress liver cancer tumor development and growth implying that IL-27 can serve as a promising therapeutic target for the patients with this devastating disease.

Example 9: Discussion

IL-27 and its receptor signaling have been implicated in the regulation of inflammation in various acute and chronic inflammatory diseases (Koltsova et al., Circulation Res., 2012, 111, 1274-1285; Villarino et al., Immunity, 2003, 19, 645-655; Peshkova et alk., Nat. Commun., 2019, 10, 5046; Yoshida et al., Immunity, 2001, 15, 569-578; and Fitzgerald et al., J. Immunol., 2007, 179, 3268-3275). Meanwhile, the role of IL-27 in cancer development has not been extensively investigated, especially in faithful in vivo models. Various immune cells have been implicated in the control of tumor initiation and progression. The accumulation of polarized and inflammatory myeloid cells, Tregs, and the exclusion or exhaustion of conventional CD4 and CD8 T cells are associated with tumor progression (Greten et al., Immunity, 2019, 51, 27-41). Similarly, chronic inflammation particularly manifested in elevated production of pro-tumorigenic cytokines and growth factors, is an underlying factor and a potent driver of cancer progression, including HCC (Ringelhan et al., Nat. Immunol., 2018, 19, 222-232). Hence, cytokines like IL-6, TNF or IL-17A were shown to be essential for HCC tumorigenesis in a variety of animal models (Park et al., Cell, 2010, 140, 197-208; and Nakagawa et al., Cancer Cell, 2014, 26, 331-343), and elevated levels of IL-6 were identified as a key biomarker of liver disease-to-HCC progression (Wong et al., Int. J. Cancer, 2009, 124, 2766-2770). While IL-27 was originally described as a pro-inflammatory cytokine, subsequent studies demonstrated its largely anti-inflammatory role, placing IL-27 into the clan of immunoregulatory cytokines (Carl et al., Int. J. Clin. Exp. Pathol., 2008, 1, 117-123). We and others previously have shown that inactivation of IL-27 in chronic inflammatory diseases such as atherosclerosis results in enhanced inflammation and production of IL-6, IL-17A and other cytokines (Koltsova et al., Circulation Res., 2012, 111, 1274-1285; Hirase et al., Amer. J. Physiol. Heart Circ. Physiol., 2013, 305, H420-9; and Peshkova et al., Sci. Rep., 2017, 7, 2255). Our initial hypotheses for this study therefore were that IL-27 would play an anti-inflammatory role in HCC, thereby reducing expression of key inflammatory tumor promoters, and that IL-27R signaling inactivation will result in heightened HCC development.

Here using two different in vivo models of HCC, one carcinogen-induced and injury-promoted and another NASH-driven, we surprisingly found that genetic inactivation of IL-27R suppresses HCC. Furthermore, through TCGA database analysis we found that elevated mRNA expression of IL-27R positively correlates with poor survival since the initial treatment alone and with more advanced stages of HCC development.

The emerging mechanism of immune-regulatory and pro-tumorigenic mechanism relies on the ability of IL-27R signaling to inhibit anti-cancer immune responses, particularly controlling NK cell accumulation and activation. Indeed, the experiment where NK cells were depleted during HCC development demonstrated that the effect of IL-27R signaling on HCC chiefly depends on NK cells. Liver microenvironment is uniquely enriched for NK cells, where they also exert immune surveillance (Jenne et al., Nat. Immunol., 2013, 14, 996-1006). NK cells are potent killers of senescent, infected or cancerous cells and participate in regulation of immune responses via the production of inflammatory cytokines in the normal liver (Jenne et al., Nat. Immunol., 2013, 14, 996-1006). During HCC development, the number and activation of liver NK cells gradually reduces due to the chronic exposure to yet unidentified, presumably tumor-derived stimuli and reduction in expression of NK cell attracting chemokines (Cai et al., Clin. Immunol., 2008, 129, 428-437). As obesity-induced non-alcohol steatohepatitis (NASH) is one of the major drivers of HCC, it is important to note that NK cell number and functions are also reduced in fatty liver disease (Michelet et al., Nat. Immunol., 2018, 19, 1330-1340).

We found that genetic ablation of IL-27R promoted the accumulation of NK cells in the tumor tissues, which was associated with NK-specific upregulation of CXCR6 in the tumor. Moreover, intra-tumoral NK cells exhibited heightened expression of cytotoxic molecules, implicating IL-27R signaling as a repressor of the NK-cell cytotoxic program. The activation of NK cells against target cells is dependent on the balance between activating and inhibitory receptors (Long et al., Annu. Rev. Immunol., 2013, 31, 227-258). We observed that NK cells isolated from tumors in the absence of competent IL-27R signaling exhibit upregulation of the NKG2D and the NKG2A activating receptors, which can "educate" hepatic NK cells, and downregulation of Ly-49C inhibitory receptor, which is more associated with education of peripheral NK cells. IL-27R signaling has been previously implicated in the regulation of NK cell function (Pflanz et al., Immunity, 2002, 16, 779-790; and Kumar et alk., Sci. Rep., 2019, 9, 4984). For example, IL-27 together with IL-12 and IL-2 has been shown to promote NK cell activity (Pflanz et al., Immunity, 2002, 16, 779-790). However, our data demonstrate that in vitro stimulation of NK cells with rIL-27 downregulates gene expression of cytotoxic molecules such as granule components (Gzmb, Prf1), FasL (Faslg) and IFN-γ (Ifng), as well as NKG2D (Klrk1) activating receptor. This together with in vivo observations of heightened cytotoxicity of NK cells in R27ra$^{-/-}$ HCC tumors suggest a direct suppressive function of IL-27R on NK cells.

Expression of so called 'stress ligands' on the surface of stressed or cancerous target cells as well as lack of MHC I expression is a second signal required to enable NK cell cytotoxicity (Raulet et al., Annu. Rev. Immunol., 2013, 31, 413-441; and Shifrin et al., Semin. Immunol., 2014, 26, 138-144). Our data revealed elevated expression of NK cell-stimulating stress ligands (Raet1a, H60b) and reduction in the Tap1 MHC I-processing molecule and surface MHC I expression in HCC tumors of Il27ra$^{-/-}$ mice. Moreover, the direct stimulation of HCC cells with rIL-27 suppressed Raet1a and H60b expression, implicating IL-27R signaling in the previously unknown control of HCC biology.

Apart from direct regulation of NK cells, IL-27 could also be implicated in the regulation of other cell types, which in turn could mediate NK cell accumulation and activation. For instance, other immune cell subsets in the liver microenvironment could regulate NK cell function via cell contact interactions (PD-1, MHC I, 2B4-CD48) or via production of chemokines and cytokines affecting NK cell recruitment (CXCL9, CXCL10), their differentiation and/or maturation (IL-15, IL-12, IL-18) (Han et al., Int. Immunopharmacol., 2019, 73, 10-16). In fact, we found that acute DEN administration triggered heightened mRNA expression of Cxcl9 and Cxcl10 chemokines and increased expression of the NK cell effector molecules perforin, granzyme B, TRAIL, and IFN-γ in the livers of IL-27R deficient mice 48 hours after DEN treatment. These observations are consistent with the scenario that IL-27R signaling represses the NK-mediated arm of cancer immunosurveillance, thereby enhancing HCC tumor initiation and progression.

With global obesity and type II diabetes epidemics, NASH-driven HCC is set to surpass all other forms of HCC in incidence (El-Serag, Gastroenterology, 2012, 142, 1264-1273; and Wallace et al., Expert Rev. Gastroenterol. Hepatol., 2015, 9, 765-779). The MUP-uPA and Western Diet HCC models faithfully resembles human HCC driven by fatty liver disease and liver fibrosis, respectively. We found that IL-27R deficiency not only suppresses tumor development in this model, but also strongly reduces the underlying fibrosis. Similar to observations in the DEN model, MUP-uPA$^+$Il27ra$^{-/-}$ mice also showed enhanced NK cell activation, implying existence of a common mechanism regulated by IL-27R signaling. Interestingly, stellate cells and fibroblasts constituting fibrotic mass in NASH and HCC are often senescent (Papatheodoridi et al., Hepatology, 2020, 71, 363-374) and NK cells have can be senolytic (Ruscetti et al., Science, 2018, 362, 1416-1422).

While several models of liver cancer are available, each of them has their advances and limitations (Febbraio et al., Cell. Metab., 2019, 29, 18-26). Our work, however, demonstrates that ablation of IL-27R limits liver cancer development in two different models of HCC: carcinogen-induced and injury-promoted HCC (DEN) and NASH-driven HCC (MUP-uPA+WD). This, along with human data on poor survival and advanced tumor stages in Il27ra$^{hi}$ HCC patients, implies that the IL-27 pathway plays a tumor-promoting role in HCC that is generalizable across different models and types of HCC with different drivers. An essential component of this mechanism is mediated through IL-27 dependent suppression of intra-tumoral NK cell function and increased innate resistance to tumors.

Taken together, our data uncover the important role of IL-27R-mediated regulation of NK cells in liver cancer development, where it directly and indirectly controls NK cell accumulation and activation. In vivo neutralization of IL-27 strongly suppress liver cancer development suggesting that inhibition of IL-27 or its receptor signaling could represent a novel preventive or therapeutic target in HCC.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of treating non-alcoholic steatohepatitis (NASH) in a subject, the method comprising administering to the subject an antibody, or an antigen-binding fragment thereof, that binds IL-27.

2. The method of claim 1, wherein the antibody is administered in combination with one or more additional therapeutic agents or procedures, wherein the one or more additional therapeutic agents or procedures is selected from the group consisting of: a chemotherapy, a targeted anti-cancer therapy, an oncolytic drug, a cytotoxic agent, an immune-based therapy, a cytokine, a surgical procedure, a radiation procedure, an activator of a costimulatory molecule, an inhibitor of an inhibitory molecule, a vaccine, or a cellular immunotherapy, or any combination thereof.

3. The method of claim 1, wherein the subject has liver fibrosis.

4. The method of claim 1, wherein the antigen-binding fragment comprises scFv.

5. The method of claim 1, wherein the antibody is a humanized antibody.

6. A method of treating non-alcoholic steatohepatitis (NASH) in a subject, comprising inhibiting IL-27R signaling in the subject by administering to the subject an antibody, or an antigen-binding fragment thereof, that binds IL-27R.

7. The method of claim 6, wherein the antibody is conjugated to an effector moiety.

* * * * *